United States Patent
Hadcock

(10) Patent No.: US 12,220,414 B2
(45) Date of Patent: Feb. 11, 2025

(54) USE OF sGC STIMULATORS FOR THE TREATMENT OF MITOCHONDRIAL DISORDERS

(71) Applicant: Tisento Therapeutics Inc., Cambridge, MA (US)

(72) Inventor: John R. Hadcock, Cambridge, MA (US)

(73) Assignee: Tisento Therapeutics Inc., Cambridge, MA (US)

( * ) Notice: Subject to any disclaimer, the term of this patent is extended or adjusted under 35 U.S.C. 154(b) by 687 days.

(21) Appl. No.: 17/258,913

(22) PCT Filed: Jul. 11, 2019

(86) PCT No.: PCT/US2019/041437
§ 371 (c)(1),
(2) Date: Jan. 8, 2021

(87) PCT Pub. No.: WO2020/014504
PCT Pub. Date: Jan. 16, 2020

(65) Prior Publication Data
US 2021/0177846 A1  Jun. 17, 2021

Related U.S. Application Data

(60) Provisional application No. 62/697,671, filed on Jul. 13, 2018, provisional application No. 62/696,582, filed on Jul. 11, 2018.

(51) Int. Cl.
| | | |
|---|---|---|
| *A61K 31/506* | (2006.01) | |
| *A61K 31/197* | (2006.01) | |
| *A61K 31/401* | (2006.01) | |
| *A61K 31/5377* | (2006.01) | |
| *A61P 25/28* | (2006.01) | |

(52) U.S. Cl.
CPC .......... *A61K 31/506* (2013.01); *A61K 31/197* (2013.01); *A61K 31/401* (2013.01); *A61K 31/5377* (2013.01); *A61P 25/28* (2018.01)

(58) Field of Classification Search
CPC .. A61K 31/506; A61K 31/197; A61K 31/401; A61K 31/5377; A61P 25/28
See application file for complete search history.

(56) References Cited

U.S. PATENT DOCUMENTS

| | | | | |
|---|---|---|---|---|
| 9,061,030 B2* | 6/2015 | Kim | .................... | A61K 31/497 |
| 10,858,363 B2* | 12/2020 | Rennie | .................... | A61P 3/10 |
| 11,466,015 B2* | 10/2022 | Nti-Addae | .............. | A61P 25/00 |
| 2005/0256186 A1* | 11/2005 | Morishige | ............... | A61P 25/08 |
| | | | | 514/474 |
| 2016/0256460 A1 | 9/2016 | Fluge et al. | | |
| 2018/0065971 A1 | 3/2018 | Rennie et al. | | |
| 2022/0009937 A1* | 1/2022 | Rennie | ................... | A61P 33/12 |

FOREIGN PATENT DOCUMENTS

| | | | |
|---|---|---|---|
| CN | 105813637 A | 7/2016 | |
| JP | 2007-508247 A | 4/2007 | |
| WO | 2005/030147 A2 | 4/2005 | |
| WO | 2015/089182 A1 | 6/2015 | |
| WO | 2017/011611 A1 | 1/2017 | |
| WO | WO-2017106175 A2 * | 6/2017 | .......... A61K 31/197 |
| WO | WO-2017116776 A1 * | 7/2017 | ......... A61K 31/4422 |
| WO | 2017/136309 A1 | 8/2017 | |
| WO | WO-2018045276 A1 * | 3/2018 | .......... A61K 31/437 |
| WO | 2018/089328 A1 | 5/2018 | |
| WO | WO-2018089330 A2 * | 5/2018 | ............. A61P 21/00 |
| WO | 2020/014504 A1 | 1/2020 | |

OTHER PUBLICATIONS

L. Roberts, et al. Acidic triazoles as soluble guanylate cyclase stimulators, Bioorganic & Medicinal Chemistry Letters, 2011, vol. 21, Issue 21, pp. 6515-6518, doi.org/10.1016/j.bmcl.2011.08.071. (Year: 2011).*
Drogalis-Kim et al., Right sided heart failure and pulmonary hypertension: New insights into disease mechanisms and treatment modalities. Progress in Pediatric Cardiology. Dec. 2016;43:71-80.
Rhodes et al., Therapeutic targets in pulmonary arterial hypertension. Pharmacol Ther. Jan. 2009;121(1):69-88.
International Search Report and Written Opinion for Application No. PCT/US2019/041437, dated Dec. 2, 2019, 14 pages.
Bentlage et al., Relationship of genotype to phenotype in fibroblast-derived transmitochondrial cell lines carrying the 3243 mutation associated with the MELAS encephalomyopathy: shift towards mutant genotype and role of mtDNA copy number. Hum Mol Genet. Feb. 1996;5(2):197-205.
Choi et al., Mutational analysis of whole mitochondrial DNA in patients with MELAS and MERRF diseases. Exp Mol Med. Jun. 30, 2010;42(6):446-55.

* cited by examiner

*Primary Examiner* — Medhanit W Bahta
*Assistant Examiner* — Manahil Mirghani Ali Abdalhameed
(74) *Attorney, Agent, or Firm* — McCarter & English, LLP; Xin Zhang; James M. Alburger

(57) ABSTRACT

The present disclosure relates to methods, uses, pharmaceutical compositions comprising an sGC stimulator or a pharmaceutically acceptable salt thereof, alone or in combination with one or more additional therapeutic agents, for the treatment of a mitochondrial disorder.

4 Claims, 10 Drawing Sheets

Statistical analysis was based on two-tailed unparied t-test compared to obese group, ##p<0.01

Statistical analysis was based on one-way ANOVA followed by Dunnett's multiple comparisons test compared to obese group, *p<0.05; **p<0.01

Statistical analysis was based on one-way ANOVA followed by Dunnett's multiple comparisons test compared to group obese control, p<0.01, **p<0.0001

Statistical analysis was based on two-tailed unparied t-test compared to obese group, ##p<0.01, ###p<0.001

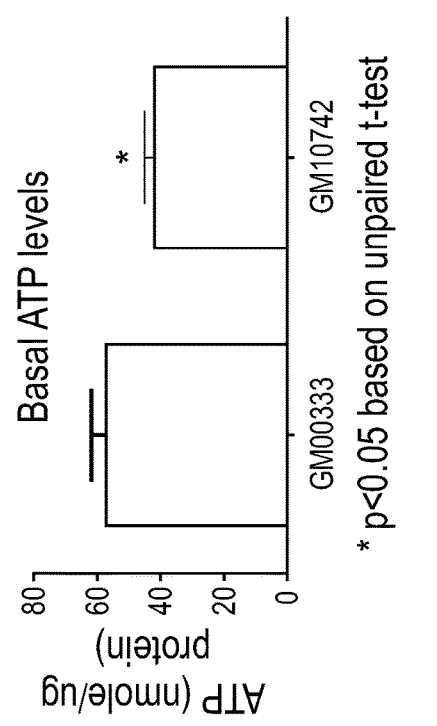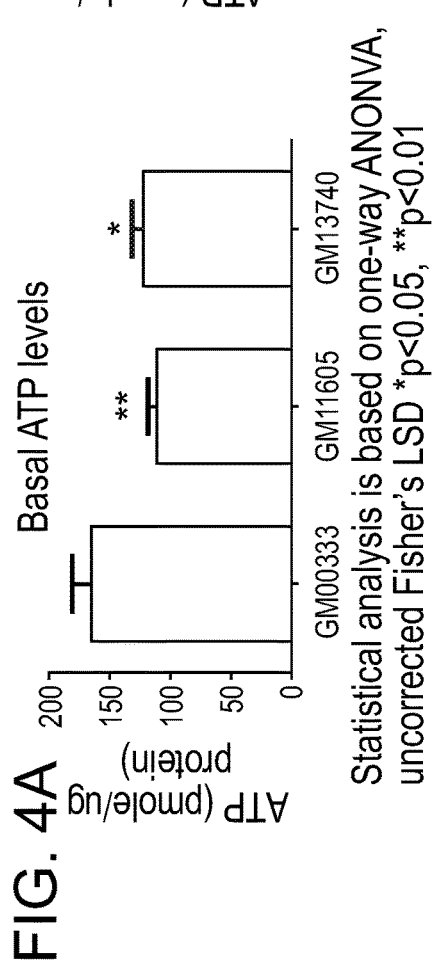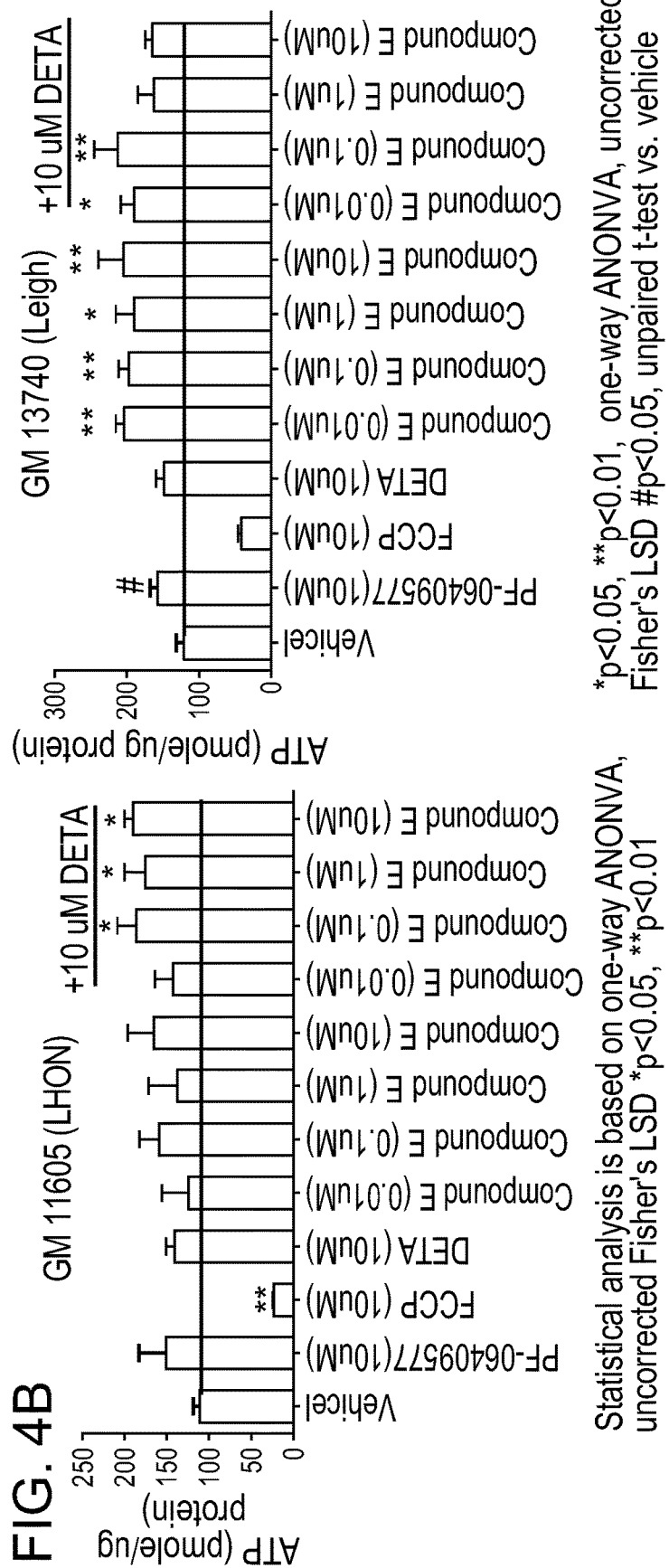
FIG. 4A
FIG. 4B

Statistical analysis is based on one-way ANONVA, uncorrected Fisher's LSD against vehicle, p<0.01, *p<0.001, ****p<0.0001

Statistical analysis is based on one-way ANONVA, uncorrected Fisher's LSD against vehicle, ***p<0.001

Statistical analysis is based on one-way ANONVA, uncorrected Fisher's LSD against vehicle, *p<0.05, p<0.01, *p<0.001

Statistical analysis is based on one-way ANONVA, uncorrected Fisher's LSD against vehicle, ***p<0.05

USE OF sGC STIMULATORS FOR THE TREATMENT OF MITOCHONDRIAL DISORDERS

RELATED APPLICATIONS

This application is a 35 U.S.C. § 371 national stage filing of International Application No. PCT/US2019/041437, filed on Jul. 11, 2019, which in turn claims the benefit of the filing date, under 35 U.S.C. § 119(e), of U.S. Provisional Application No. 62/696,582, filed on Jul. 11, 2018, and U.S. Provisional Application No. 62/697,671, filed on Jul. 13, 2018. The entire contents of each of the above-referenced applications are incorporated herein by reference.

BACKGROUND

Mitochondria are organelles that generate energy for the cell through oxidative phosphorylation to produce adenosine trisphosphate (ATP), which is required normal cellular function. Accordingly, proper mitochondrial function is critical for maintaining health and life.

Mitochondrial disorders are a group of disorders caused by dysfunctional mitochondria. Mitochondrial disorders may be caused by mutations (acquired or inherited), in mitochondrial DNA or in nuclear genes that code for mitochondrial components. They may also be the result of acquired mitochondrial disorder due to adverse effects of drugs, infections, or other environmental causes. These disorders can be present at birth or develop later in life.

In addition to reduced ATP production in mitochondrial disorder, lactic acidosis due to reduced pyruvate conversion to acetyl CoA, reduced nitric oxide (NO) synthesis leading to NO deficiency, increased cellular damage due to elevated reactive oxygen species and reduced vascular reactivity are also observed. They cause debilitating physical, developmental, and cognitive disabilities with symptoms including poor growth; loss of muscle coordination; muscle weakness and pain; seizures; vision and/or hearing loss; gastrointestinal issues; learning disabilities; and organ failure. Life expectancy is greatly reduced. It is estimated that 1 in 4,000 people has mitochondrial disorder. Mitochondrial disorders are usually progressive and there are no cures or approved therapies.

There is a need to develop methods of treating mitochondrial disorders.

SUMMARY

In one aspect, the invention provides a method of treating a mitochondrial disorder, comprising administering a therapeutically effective amount of an sGC stimulator, or pharmaceutically acceptable salt thereof, alone or in combination with a therapeutically effective amount of one or more additional therapeutic agents to a patient in need thereof.

In another aspect, the invention provides pharmaceutical compositions comprising an sGC stimulator or a pharmaceutically acceptable salt thereof, for use in the treatment of a mitochondrial disorder in a patient in need thereof.

In another aspect, the invention provides pharmaceutical compositions comprising an sGC stimulator, or a pharmaceutically acceptable salt thereof, in combination with one or more additional therapeutic agents, for use in the treatment of a mitochondrial disorder in a patient in need thereof.

BRIEF DESCRIPTION OF THE DRAWINGS

FIGS. 4A, 4B, 4C and 4D are plots of showing that the ATP level in LHON patient cells, GM11605 and GM 10742, and Leigh patient cells GM13740 were significantly lower than in healthy cells, GM 00333 (A); Stimulation of GM11605 and GM13740 with Compound E (alone or in combination with DETA) significantly increase the ATP level (B); Stimulation of GM11605 and GM13740 with Compound B (alone or in combination with DETA) increase ATP level (C). Compound B was also tested in another LHON patient cells, GM10742, similar result was observed as in GM 11605 (data not shown); Stimulation of GM13740 cells with Compound D (alone or in combination with DETA) increased ATP levels significantly (D).

DETAILED DESCRIPTION

Figure 1A:
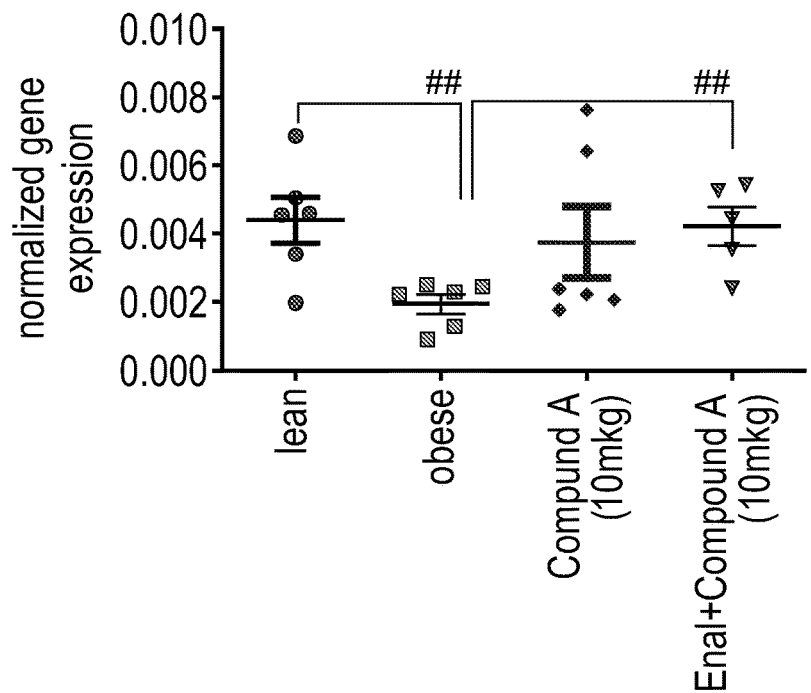
FIGS. 1A, 1B and 1C are plots of the gene expression level of PGC1α in the (A) white adipose tissue (WAT) of ZSF1 Rats, (B) liver tissue of ZSF1 Rats, and (C) hypothalamus of diet-induced obese (DIO) mice.

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls. The compounds described herein may be defined by their chemical structures and/or chemical names. Where a compound is referred to by both a chemical structure and a chemical name, and the chemical structure and chemical name conflict, the chemical structure is determinative of the compound's identity.

It has been recently found that mitochondrial biogenesis and function are enhanced by nitric oxide (NO). In cells, NO is synthesized from arginine and oxygen by various nitric oxide synthase (NOS) enzymes and by sequential reduction of inorganic nitrate. Soluble guanylate cyclase (sGC) is the primary receptor or target for NO in vivo. sGC can be activated via both NO-dependent and NO-independent mechanisms. In response to this activation, sGC converts guanosine triphosphate (GTP) into the secondary messenger cyclic guanosine monophosphate (cGMP). The increased level of cGMP, in turn, modulates the activity of downstream effectors including protein kinases, phosphodiesterases (PDEs) and ion channels.

NO-independent, heme-dependent, sGC stimulators have several important differentiating characteristics, when compared to other types of sGC modulators, including crucial dependency on the presence of the reduced prosthetic heme moiety for their activity, strong synergistic enzyme activation when combined with NO and stimulation of the synthesis of cGMP by direct stimulation of sGC, independent of NO.

Therapeutic Methods

In one aspect, the invention provides a method of treating a mitochondrial disorder, comprising administering a therapeutically effective amount of an sGC stimulator, or pharmaceutically acceptable salt thereof, alone or in combination with a therapeutically effective amount of one or more additional therapeutic agents to a patient in need thereof.

In another aspect, the invention provides pharmaceutical compositions comprising an sGC stimulator or a pharmaceutically acceptable salt thereof, for use in the treatment of a mitochondrial disorder in a patient in need thereof.

In another aspect, the invention provides pharmaceutical compositions comprising an sGC stimulator, or a pharmaceutically acceptable salt thereof, in combination with one or more additional therapeutic agents, for use in the treatment of a mitochondrial disorder in a patient in need thereof.

The term "disorder", as used herein refers to any deviation from or interruption of the normal structure or function of any body part, organ, or system that is manifested by a characteristic set of symptoms and signs and whose etiology, pathology, and prognosis may be known or unknown. The term disorder encompasses other related terms such as disease and condition (or medical condition) as well as syndromes, which are defined as a combination of symptoms resulting from a single cause or so commonly occurring together as to constitute a distinct clinical picture. In some embodiments, the term disorder refers to a mitochondrial disorder.

"Mitochondrial disorders" refer to a group of conditions that affect the mitochondria (the structures in each cell of the body that are responsible for making energy). The disorder can present at any age with almost any affected organ, including the brain, muscles, heart, liver, nerves, eyes, ears and kidneys. Some disorders affect only one organ or tissue, many involve multiple organ systems including the brain, muscles, heart, liver, nerves, eyes, ears and/or kidneys.

In some embodiments, the mitochondrial disorder is a mitochondrial disease, which results from mutations in mitochondrial genes or proteins encoded by either mitochondrial or nuclear DNA, mitochondrial DNA deletions or mitochondrial DNA depletions, leading to dysfunction of the mitochondria resulting in an ATP deficit and overproduction of reactive oxygen species (ROS) (Renkema G H et al 2017 human genetics; Chinnery P F and Hudson G, 2013 british medical bulletin; Iizuka 2005, Pitkanen 1996, Esposito 1999). Mitochondrial diseases manifest primarily due to a chronic loss of cellular ATP that results in a variety of clinical phenotypes and syntomatology (Chinnery P F and Hudson G, 2013 british medical bulletin). Accordingly, ATP deficits have been described in multiple mitochondrial diseases such as MERFF (Chang J C et al 2013), KSS (Mahato B et al 2011), MELAS (Seo K S et al 2018; Uittenbogaard M et al 2019), Leber's hereditary optic neuropathy (LHON) (Van Bergen N J et al 2015; Zhang J et al 2016 and Uittenbogaard M et al 2019), Complex II deficiency (Mbaya E et al 2010), Complex III deficiency (Tegelberg, S et al 2017), mitochondrial encephalomyoptahy (Gai, X et al 2013, americal journal of human genetics), Barth syndrome (Dudek, J et al 2013 stem cell research), NARP (Rak, M et al 2007, JBC), Leigh syndrome and Complex I deficiency (Moran, M et al 2010 Biochimica et Biophysica Acta; Barca, E et al 2018 Human molec genetics). Increasing ATP levels is believed to improve disease symptomatology across these disorders (Webb M et al 2019). Treatment of mitochondrial disease patient cells deficient in ATP with an sGC stimulator (alone or in combination of DETA) increases ATP levels across different mitochondrial disease patient cells (FIG. 4A-D).

Figure 5A:
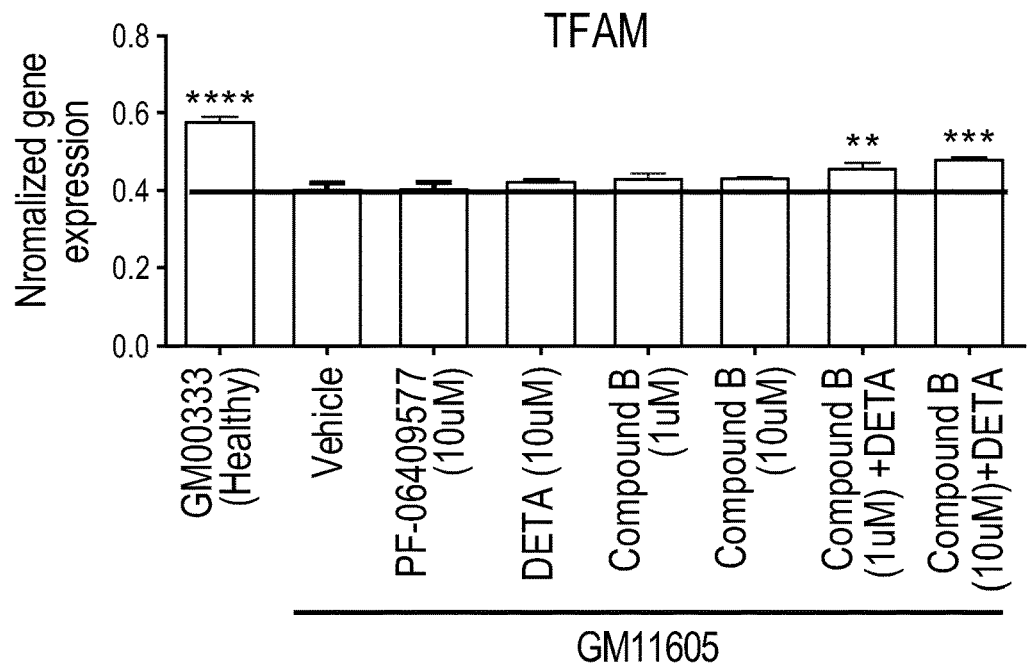
FIGS. 5A and 5B are plots showing the effects of Compound B on expression levels of (A) TFAM and (B) DDAH2 genes in LHON patient cells, GM11605.
Figure 5B:
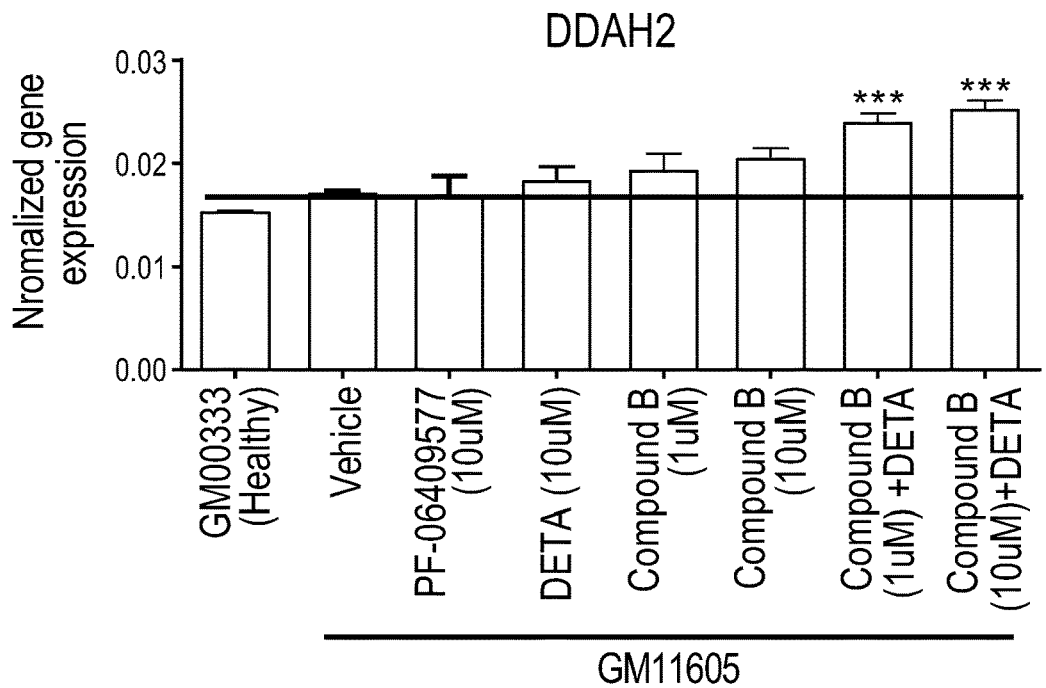
Figure 6A:
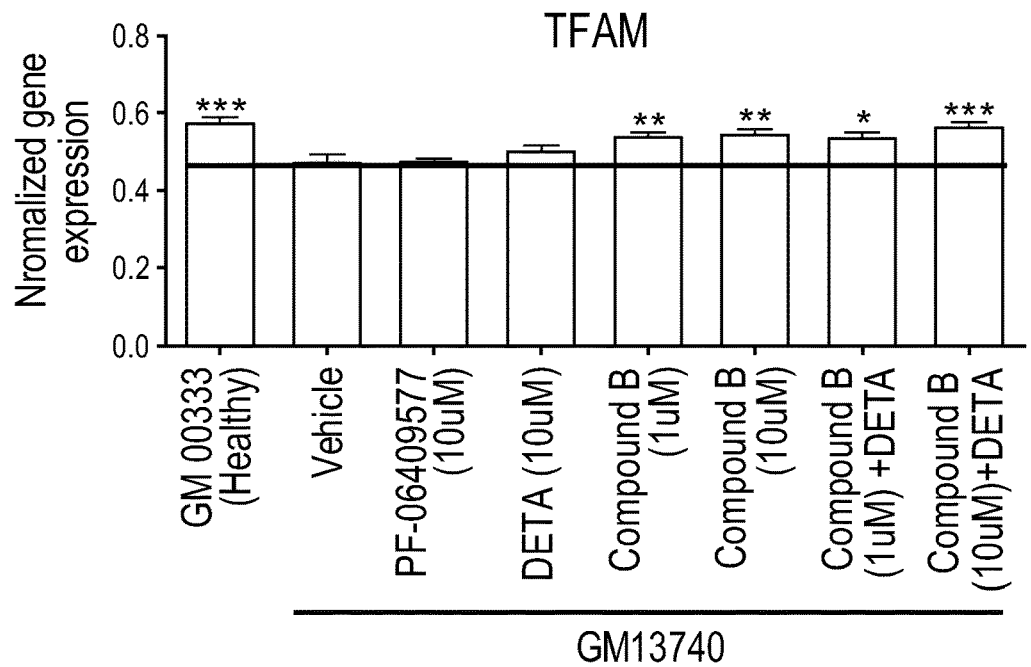
FIGS. 6A and 6B are plots showing the effects of Compound B on expression levels of (A) TFAM and (B) DDAH2 genes Leigh patient cells, GM13740.
Figure 6B:
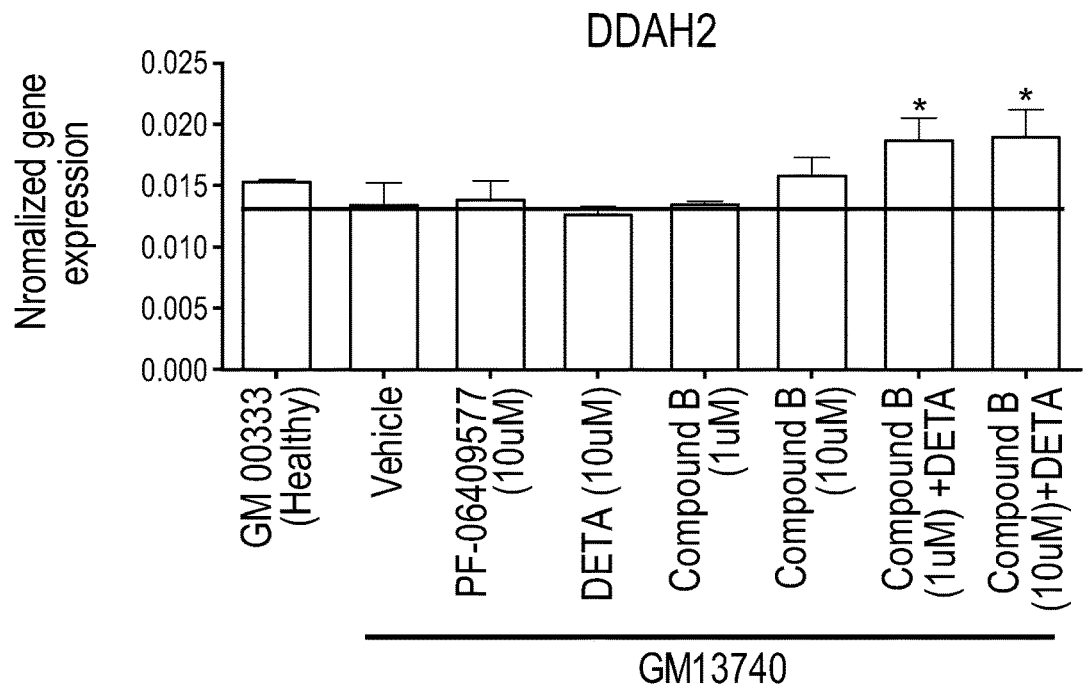

In addition to the ATP crisis, mitochondrial respiratory chain dysfunction also causes excessive ROS production and increased oxidative stress, leading to cellular damage (Iizuka et al 2005, Pitkanen et al 1996, Esposito et al 1999, Blankenberg, F G 2012 Molecular genetics and metabolism, Turrens J F et al 1997). Glutathione (GSH) plays a critical role in protecting cells from oxidative stress (Forman et al 2008 PMID 18796312) and the decrease of GSH or GSH:GSSG (reduced glutathione:oxidized glutathione) ratio is indicative of oxidative stress (Enns eta al 2017, J, Clin Medicine). Low levels of iGSH, which are indicative of systemic oxidative stress, were found in blood cells of patients with a variety of mitochondrial diseases such as: 4tRNALeu3243AG, 4 complex I deficiency, 2 complex IV deficiency, 2 combined complex I/III deficiency, 1 combined complex I/IV deficiency (tRNALeu3243AT), 1 combined complex II/III deficiency, 1 complex III deficiency, 1 mtDNA deletion syndrome, 1 mtDNA depletion syndrome (TK2 deficiency), and 3 with undefined disease but with clinical features including Leigh syndrome or multiorgan system involvement, and biochemical findings consistent with mitochondrial disease (Atkuri, K R et al 2009). Therefore, oxidative stress is involved in various mitochondrial diseases and therapies that are protective against oxidative stress would be desirable for mitochondrial disease patients (Webb M et al 2019). Level of TFAM mRNA, which encodes a protein that protects the mtDNA from oxidative stress by binding to it in a non-sequence specific manner (Kanki et al., 2004) is increased by sGC stimulator treatment (FIGS. 5A and 6A). Additionally, treatment of mitochondrial disease patient cells with an sGC stimulator increases the levels of DDAH2 mRNA. Upregulation of the DDAH pathway is expected to reduce ADMA levels in mitochondrial disease patients and decrease the deleterious effects of oxidative stress in these patients ((FIGS. 5B and 6B).

As described above, mitochondrial genetic disorders can be caused by mutations in either the mitochondrial DNA or nuclear DNA that lead to dysfunction of the mitochondria and inadequate production of cellular ATP. Those caused by mutations in mitochondrial DNA are transmitted by maternal inheritance, while those caused by mutations in nuclear DNA may follow an autosomal dominant, autosomal recessive, or X-linked pattern of inheritance. (See: rarediseases-.info.nih.gov/diseases/7048/mitochondrial-genetic-disorders, last accessed Jul. 10, 2018, the teaching of which are incorporated herein by reference.)

Specific mitochondrial disease which may be treated and/or prevented by administering an sGC stimulator of the invention (e.g., a sGC stimulator or a pharmaceutically acceptable salt thereof), include but are not limited to:

Alpers Disease, Autosomal Dominant Optic Atrophy (ADOA), Barth Syndrome/LIC (Lethal Infantile Cardiomyopathy), Beta-oxidation defects, Systemic Primary Carnitine Deficiency, Long Chain Fatty Acid Transport Deficiency, Carnitine Palmitoyl Transferase Deficiency, Carnitine/Acylcarnitine Translocase Deficiency, Carnitine Palmitoyl Transferase I (CPT I) Deficiency, Carnitine Palmitoyl Transferase II (CPT II) Deficiency, Very Long-Chain Acyl-CoA Dehydrogenase Deficiency (VLCAD), Long-Chain Acyl-CoA Dehydrogenase Deficiency (LCAD), Long-Chain 3-Hydroxyacyl-CoA Dehydrogenase deficiency (LCHAD), Multiple Acyl-CoA Dehydrogenase Deficiency (MAD/Glutaric acidurioa Type II), Mitochondrial Trifunctional Protein Deficiency, Medium-Chain Acyl-CoA Dehydrogenase (MCAD) Deficiency, Short-Chain Acyl-CoA Dehydrogenase Deficiency (SCAD), Glutaric Aciduria Type II, (SCHAD) Deficiency, Short/Medium-Chain 3-Hydroxyacyl-CoA Dehydrogenase (S/MCHAD), Medium-Chain 3-Ketoacyl-CoA Thiolase Deficiency, 2,4-Dienoyl-CoA Reductase Deficiency, Mitochondrial Enoyl CoA Reductase Protein Associated Neurodegeneration (MEPAN), Carnitine Deficiency, Creatine Deficiency Syndromes, Co-Enzyme Q10 Deficiency, Complex I, II, III, IV, V Deficiency, Chronic Progressive External Ophthalmoplegia (CPEO), Friedreich's Ataxia, Kearns-Sayre syndrome, Leukodystrophy, Leigh Disease or Syndrome, LHON, LHON Plus, Luft Disease, MELAS (Mitochondrial myopathy, encephalomyopathy, lactic acidosis, stroke-like symptoms), Myoclonic Epilepsy with Ragged Red Fibers (MERRF), Mitochondrial Recessive Ataxia Syndrome (MIRAS), Mitochondrial Cytopathy, Mitochondrial DNA Depletion, Mitochondrial Encephalopathy, Mitochondrial Myopathy, Multiple Mitochondrial Dysfunction Syndrome, MNGIE (Myoneurogenic gastrointestinal encephalopathy), NARP (Neuropathy, ataxia, retinitis pigmentosa, and ptosis), Pearson Syndrome, Pyruvate Carboxylase Deficiency, Pyruvate Dehydrogenase Deficiency or Pyruvate Dehydrogenase Complex Deficiency (PDCD/PDH), and POLG Mutations.

In one embodiment, the mitochondrial disease is selected from Alpers, Carnitine-acyl-carnitine deficiency, Carnitine deficiency, Complex I, II, III, IV deficiency, CPEO, CPT II deficiency, Creatine deficiency syndrome, KSS, LCHAD, Leigh syndrome, Leukodystrophy, LHON, MELAS, MEPAN, MERRF, MIRAS, Mitochondrial DNA depletion, MNGIE, NARP, Pearson syndrome, and POLG mutations.

In some embodiments of the above methods and uses, the sGC stimulator is administered before a symptom of mitochondrial dysfunction or disorder (or disease) fully develops in said patient. In other embodiments of the above methods and uses, the sGC stimulator is administered after one or more symptoms of mitochondrial disorder (or disease) develops in said patient.

In another aspect, the invention also provides a method of treating a mitochondrial disorder (or disease) in a subject in need thereof, comprising administering, alone or in combination therapy, a therapeutically effective amount of a sGC stimulator, or a pharmaceutically acceptable salt thereof to the subject.

As used herein, in some embodiments, the term a "patient in need thereof" is used to refer to a patient suffering from one of the mitochondrial disorders (or diseases) described above.

In some embodiments, the "patient in need thereof" is a patient with mitochondrial disorder (or disease) or who has been diagnosed with it or who is genetically predisposed to the development of said disorder. In other embodiments a patient in need thereof is a person that has been genetically tested and found to have a mutation in a gene that predisposes him or her to the development of said disorder (or disease), even though he or she may not show any physical symptoms of the disorder (or disease) yet. In still other embodiments, a "patient in need thereof" displays symptoms of the disorder (or disease) even though a formal diagnosis has not been made yet. The most common signs and symptoms of mitochondrial disorder (or disease) include: poor growth, loss of muscle coordination, muscle weakness, fatigue, exercise intolerance, lactic acidosis, seizures, cognitive impairment, mental fatigue, autism, problems with vision and/or hearing, developmental delay, learning disabilities, heart, liver, and/or kidney disease, gastrointestinal disorders, diabetes, increased risk of infection, thyroid and/or adrenal abnormalities, autonomic dysfunction, and dementia.

In some embodiments, mitochondrial disorder is mitochondrial dysfunction caused by a non-mitochondrial disease. In some embodiments, the patient in need thereof is a patient with mitochondrial dysfunction who is suffering from a non-mitochondrial disease. In some embodiments, the patient in need thereof is a patient having mitochondrial dysfunction caused by a non-mitochondrial disease. In certain embodiments, the non-mitochondrial disease is a disease that can result in mitochondrial dysfunction in some patients suffering from such disease. In certain embodiments, the non-mitochondrial disease is selected from, for example, ALS, Duchenne muscular dystrophy, chronic fatigue syndrome, cardiomyopathies, sarcopenia, cachexia, ataxia disorders, aging and senescence, sickle cell disease, Alzheimer's disease, Parkinson disease, Huntington's disease, cancer, Multiple Sclerosis, hippocampal sclerosis/epilepsy, epilepsy, Glaucoma, Harding's syndrome, diabetes (type 1 and type II), diabetes mellitus and deafness (DAD), dementia, bipolar disorder, schizophrenia, anxiety disorders, cardiovascular diseases, galactosialidosis, migraine headaches, stroke, neuropathic pain, transient schemic attack, coronary artery disease, fibromyalgia, retinitis pigmentosa, hepatitis C, primary biliary cirrohosis, and X-adrenoleukodystrophy. (See Experimental and Molecular Pathology Volume 83, Issue 1, August 2007, Pages 84-92, the teachings of which are hereby incorporated by reference.)

As such, one aspect of this invention is treating a patient having ALS, Duchenne muscular dystrophy, chronic fatigue syndrome, cardiomyopathies, sarcopenia, cachexia, ataxia disorders, aging and senescence, sickle cell disease, Alzheimer's disease, Parkinson disease, Huntington's disease, cancer, Multiple Sclerosis, hippocampal sclerosis/epilepsy, epilepsy, Glaucoma, Harding's syndrome, diabetes (type I and type II), diabetes mellitus and deafness (DAD), dementia, bipolar disorder, schizophrenia, anxiety disorders, cardiovascular diseases, galactosialidosis, migraine headaches, stroke, neuropathic pain, transient schemic attack, coronary artery disease, fibromyalgia, retinitis pigmentosa, hepatitis C, primary biliary cirrohosis, and X-adrenoleukodystrophy, wherein the patient is suffering from mitochondrial dysfunction comprising administering a therapeutically effective amount of an sGC stimulator, or pharmaceutically acceptable salt thereof, alone or in combination with a therapeutically effective amount of one or more additional therapeutic agents to a patient in need thereof.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically effective amount of the compound to be administered will be governed by such considerations, and is the minimum amount necessary to ameliorate, cure or treat the disorder or one or more of its symptoms, or to prevent or substantially lessen the chances of acquiring a disorder or a symptom or to reduce the severity of the disorder or one or more of its symptoms before it is acquired or before the symptoms develop further or fully develop. In some embodiments of the above methods, uses and compositions, the patient in need thereof is an adult. In other embodiments the patient is a child. In still other embodiments the patient in need thereof is an infant.

In some embodiments of the above methods, uses and compositions, the administration of an sGC stimulator or pharmaceutically acceptable salt thereof, alone or in combination with another therapeutic agent, results in an improvement of a measurable physical or physiological parameter or both.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a companion animal or pet (e.g., a dog, cat, mice, rats, hamsters, gerbils, guinea pig or rabbit). In some embodiments, the subject is a human.

The invention also provides a method for treating one of the above mitochondrial disorders in a subject, comprising administering a therapeutically effective amount of a sGC stimulator, or a pharmaceutically acceptable salt thereof, to the subject in need of the treatment. Alternatively, the invention provides the use of a sGC stimulator, or a pharmaceutically acceptable salt thereof, in the treatment of one of these mitochondrial disorders in a subject in need of the treatment. Also included in the invention is the use of a sGC stimulator, or a pharmaceutically acceptable salt thereof, for the manufacture of medicament for treating one of the above mitochondrial disorders in a subject in need of the treatment. The invention further provides a method of making or manufacturing a medicament useful for treating one of these mitochondrial disorders comprising using a sGC stimulator, or a pharmaceutically acceptable salt thereof.

The compounds and pharmaceutical compositions described herein can be used alone or in combination therapy for the treatment of a mitochondrial disorder mediated, regulated or influenced by sGC, cGMP and/or NO.

In other embodiments, the invention provides a method of increasing mitochondrial function in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, cerebrospinal fluid (CSF), or other body fluids or extracts thereof.

"Treat", "treating" or "treatment" with regard to a disorder, refers to alleviating or abrogating the cause and/or the effects of the disorder. In one embodiment, the terms "treat", "treatment" and "treating" refer to the reduction or amelioration of the progression, severity and/or duration of disorder, or the amelioration of one or more symptoms of the disorder (i.e., "managing" without "curing" the disorder). In specific embodiments, the terms "treat"; "treatment" and "treating" refer to the amelioration of at least one measurable physical parameter of a disorder. In other embodiments the terms "treat", "treatment" and "treating" refer to the inhibition of the progression of a disorder either physically by, e.g., stabilization of a discernible symptom or physiologically by, e.g., stabilization of a physiological parameter, or both. In some embodiments, the terms "treat," "treatment" and "treating" refer to delaying the onset of a symptom or set of symptoms or clinical manifestations or to delaying the onset of a loss in certain physical function.

In some embodiments, treatment results in amelioration of at least one measurable physical parameter of a mitochondrial disorder. In other embodiments, treatment results in the reduction, inhibition or slowing down of the progression of a mitochondrial disorder either physically by, e.g., stabilization of a measurable symptom or set of symptoms, or physiologically by, e.g., stabilization of a measurable parameter, or both. Measurable physical parameters in the brain of the patient with a mitochondrial disorder include developmental delays, frequency and severity of headache, migraines, seizures, dementia, autistic features, atypical cerebral palsy, neuro-psychiatric disturbances, mental retardation, brain lesions, brain neuromatalobite changes (for example NAA, amino acids and lactate), stroke-like episode frequency or severity, cerebral blood flow, cerebrovascular reactivity, oxygen extraction fraction, cognition, and brain fatigue. Measurable physical parameters in the nervous system of the patient with a mitochondrial disorder include weakness (may be intermittent), fainting, absent reflexes, neuropathic pain, dysautonomia, temperature instability. Measurable physical parameters in the muscles of the patient with a mitochondrial disorder include fatigue, endurance capacity, weakness, motor coordination, ataxia, irritable bowel syndrome, gastroesophogeal reflux, cramping, diarrhea or constipation, hypotonia, gastrointestinal problems, pseudo-obstruction, and dysmotility. Measurable physical parameters in the kidneys of the patient with a mitochondrial disorder include renal tubular acidosis or wasting. Measurable physical parameters in the heart of the patient with a mitochondrial disorder include cardiac conduction defects (heart blocks), and cardiomyopathy. Measurable physical parameters in the liver of the patient with a mitochondrial disorder include hypoglycemia (low blood sugar) and liver failure. Measurable physical parameters in the plasma of the patient with a mitochondrial disorder include nitric oxide and lactate levels. Measurable physical parameters in the CSF of the patient with a mitochondrial disorder include lactate and amino acid levels. A skilled person would be able to use routine means (e.g., including, but not limited to laboratory tests, physical exams, cognitive tests) to determine improvement in the measurable physical parameter or set of physical parameters.

In other embodiments, treatment results in the reduction, inhibition or slowing down of the progression of a mitochondrial disease by at least one measurable parameter (for example, a physical or a physiological parameter). Measurable parameters include, but are not limited to Reduction of lactate in one or more of the plasma, blood, brain, and CSF; Normalization of the levels of ADMA in plasma and CSF; Increase NAA levels in the brain; Reduction in pyruvate in the CSF; Increase in 5-methyltetrahydrofolate in the CSF; Decrease the severity and/or frequency of stroke-like episodes (SLE) and/or epilepsy; Reduction of the the severity and frequency myoclonus and epileptic events; Improvement in the resolution of MRI abnormalities in patients that have had a SLE or seizure; Reduction of the extent, severity and progression of brain lesions; Reduction of mental fatigue and improvement or preservation of cognitive function; Reduction of the frequency and severity of headaches/migraines and seizures; Normalization of cerebral blood flow, oxygen extraction fraction, cerebrovascular reactivity and peripheral vascular reactivity; Improvement of motor function or reduction of motor abnormalities such as muscle weakness, muscle fatigue, ataxia, spasticity or myoclonous; Improvement or reduction of the loss of visual acuity; and Improvement in the quality of life of the patient. In a specific embodiment, the treatment is in a patient having a mitochondrial disease selected from Alpers, Carnitine-acyl-carnitine deficiency, Carnitine deficiency, Complex I, II, III, IV deficiency, CPEO, CPT II deficiency, Creatine deficiency syndrome, KSS, LCHAD, Leigh syndrome, Leukodystrophy, LHON, MELAS, MEPAN, MERRF, MIRAS, Mitochondrial DNA depletion, MNGIE, NARP, Pearson syndrome, and POLG mutations.

sGC Stimulators

The compounds of the invention are defined herein by their chemical structures and/or chemical names. Where a compound is referred to by both a chemical structure and a chemical name, and the chemical structure and chemical name conflict, the chemical structure is determinative of the compound's identity.

Compounds herein disclosed may be optionally substituted with one or more substituents, such as illustrated generally below, or as exemplified by particular classes, subclasses and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position unless otherwise specified. As will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal to or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, relevant knowledge of the art.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like. To be perfectly clear, the term "aliphatic chain" may be used interchangeably with the term "aliphatic" or "aliphatic group".

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" refers to a linear or branched-chain monovalent hydrocarbon radical with at least one site of unsaturation, i.e., a carbon-carbon, sp$^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "cycloaliphatic" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_3$-$C_{12}$ hydrocarbon or a bicyclic $C_7$-$C_{12}$ hydrocarbon. In some embodiments, any individual ring in a bicyclic or tricyclic ring system has 3-7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

"Cycloalkyl", as used herein, refers to a ring system in which is completely saturated and which has a single point of attachment to the rest of the molecule. Unless otherwise specified, a cycloalkyl group may be monocyclic, bicyclic, tricyclic, fused, spiro or bridged. In one embodiment, the term "cycloalkyl" refers to a monocyclic $C_3$-$C_{12}$ saturated hydrocarbon or a bicyclic $C_7$-$C_{12}$ saturated hydrocarbon. In some embodiments, any individual ring in a bicyclic or tricyclic ring system has 3-7 members. Suitable cycloalkyl groups include, but are not limited to cyclopropyl, cyclobutyl, cyclopentyl, cyclohexyl, cycloheptyl, cycloheptenyl, norbornyl, cyclooctyl, cyclononyl, cyclodecyl, cycloundecyl, cyclododecyl, and the like.

Heterocycle" (or "heterocyclyl" or "heterocyclic), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3-18 ring members in which one or more ring members is a heteroatom independently selected from oxygen, sulfur or nitrogen, and each ring in the system contains 3 to 7 ring members. In other embodiments, a heterocycle may be a monocycle having 3-7 ring members (2-6 carbon atoms and 1-4 heteroatoms) or a bicycle having 7-10 ring members (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo [2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is on the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl.

The term "aralkyl" refers to a radical having an aryl ring substituted with an alkylene group, wherein the open end of the alkylene group allows the aralkyl radical to bond to another part of the compound. The alkylene group is a bivalent, straight-chain or branched, saturated hydrocarbon group. As used herein, the term "$C_{7-12}$ aralkyl" means an aralkyl radical wherein the total number of carbon atoms in the aryl ring and the alkylene group combined is 7 to 12. Examples of "aralkyl" include, but not limited to, a phenyl ring substituted by a $C_{1-6}$ alkylene group, e.g., benzyl and phenylethyl, and a naphthyl group substituted by a $C_{1-2}$ alkylene group.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6, 5 heteroaromatic system, as used herein, for example, is a six membered heteroaromatic ring fused to a second five membered ring wherein the radical or point of attachment is on the six-membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2, 5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tri-cyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to an atom or a chain of atoms connecting two different parts of a molecule. The two atoms that are connected through the bridge (usually but not always, two tertiary carbon atoms) are referred to as "bridgeheads". In addition to the bridge, the two bridgeheads are connected by at least two individual atoms or chains of atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxatricyclo[3.3.1.03,7]nonyl. "Spiro" bicyclic ring systems share only one ring atom (usually a quaternary carbon atom) between the two rings.

The term "ring atom" refers to an atom such as C, N, O or S that is part of the ring of an aromatic ring, a cycloaliphatic ring, a heterocyclic or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or NR$^+$ (as in N-substituted pyrrolidinyl).

As used herein, the terms "alkoxy" or "alkylthio" refer to an alkyl group, as previously defined, attached to the molecule, or to another chain or ring, through an oxygen ("alkoxy" i.e., —O-alkyl) or a sulfur ("alkylthio" i.e., —S-alkyl) atom.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1-3}$ haloalkyl could be —CFHCH$_2$CHF$_2$ and a $C_{1-2}$haloalkoxy could be —OC(Br)HCHF$_2$. This term includes perfluorinated alkyl groups, such as —CF$_3$ and —CF$_2$CF$_3$.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a $C_{1-3}$ cyanoalkyl could be —C(CN)$_2$CH$_2$CH$_3$ and a $C_{1-2}$ cyanoalkenyl could be =CHC(CN)H$_2$.

As used herein, an "oxo" refers to =O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g., —CH$_2$—C(O)—CH$_3$.

In some embodiments of the above methods, uses and pharmaceutical compositions, the sGC stimulator is one selected from those described in patent application publications
WO2013101830 (e.g., any one of compounds 1 to 122), WO2012064559 (e.g., any one of compounds I-1 to I-68), WO2012003405 (e.g., any one of compounds I-1 to I-312), WO2011115804 (e.g., any one of compounds I-1 to I-63), WO2014047111 (e.g., any one of compounds I-1 to I-5), WO2014047325 (e.g., any one of compounds I-1 to I-10); WO2014144100 (e.g., any one of compounds I-1 to I-634); WO2015089182 (e.g., any one of compounds I-1 to I-72), WO2016044447 (e.g., any one of compounds 1 to 217), WO2016044446 (e.g., any one of compounds I-1 to I-94), WO2016044445 (e.g., any one of compound I-1 to I-39), WO2016044441 (e.g., any one of compound I-1 to I-20), WO2018/009596 (e.g., any one of compound I-1 to I-5), WO2018045276 (e.g., any one of compound I-1 to I-72), WO2018/089328 (e.g., any one of compound I-1 to I-16), WO 2018/089330 (e.g., any one of compound I-1 to I-135), WO2019/126354 (e.g., any one of compound I-1 to I-16), or is a pharmaceutically acceptable salt thereof.

In other embodiments of the above methods, uses and pharmaceutical compositions, the sGC stimulator is a compound described in one or more of the following publications:
WO2012165399 and WO2014084312.

In other embodiments of the above methods, uses and pharmaceutical compositions, the sGC stimulator is a compound described in one or more of the following publications:
WO9816507, WO9823619, WO9816223, WO2003004503, WO2003095451, WO2004009589, WO2004009590, WO2007124854, WO 2008031513, WO2007128454, WO2008061657, WO2010078900, WO2010079120, WO 2011147809, WO 2011147810, WO2013104598, WO2012004259, WO2012059549, WO2012143510, WO2012004258, WO2012152629, WO2012152630, WO2012010577, WO2012028647, WO2013104597, WO2013131923, WO2013104703, WO2013004785, WO2013030288, WO2014068095, WO2014068099, WO2009025888, WO2014068104, WO2014131741, WO2014131760, WO2011064156, WO2011073118, WO1998023619, WO2000006567, WO2000006569, WO2000021954, WO2000066582, WO2001083490, WO2001083490, WO2002042300, WO2002042301, WO2002042302, WO2002092596, WO2003097063, WO2004031186, WO2004031187, WO2014195333, WO2015018814, WO2015082411, WO2015124544, WO0006568, WO2001017998, WO2001047494, WO2002036120, WO2011064171, WO2014128109, WO2012010578, WO2013076168, WO2015124544, WO2015150366, WO2015150364, WO2015150363, WO2015150362, WO2015140199, WO2015150350, and WO2015140254.

In other embodiments of the above methods, uses and pharmaceutical compositions, the sGC stimulator is a compound described in one or more of the following publications:

WO2009032249, WO2015088885, WO2015088886, WO2010065275, WO2009094242, WO2010099054, WO2010065275, WO2011119518, WO2011149921, and WO2012058132.

In other embodiments of the above methods, uses and pharmaceutical compositions, the sGC stimulator is a compound described in WO2013086935.

In some further embodiments of the above methods, uses and pharmaceutical compositions, the sGC stimulator is a compound described in one or more of the following publications: WO2000006568, WO2001017998, WO2001047494 and WO2002036120.

In some further embodiments of the above methods, uses, and pharmaceutical compositions, the sGC stimulator is a compound described in one or more of the following publications: US20110131411, WO2011064156 and WO2011073118.

In some further embodiments of the above methods, uses and pharmaceutical compositions, the sGC stimulator is a compound described in one or more of the following publications: US20140315926, WO2013076168 WO2003095451, WO2011064171, WO2013086935 and WO2014128109.

Some further embodiments of the above methods, uses and pharmaceutical compositions, the sGC stimulator is a compound described in one or more of the following publications: WO2011147809, WO2011147810WO2012010578, WO2012059549 and WO2013076168.

In some embodiments of the above methods, uses and pharmaceutical compositions, the sGC stimulator is a compound according to Formula IA, or pharmaceutically acceptable salts thereof,

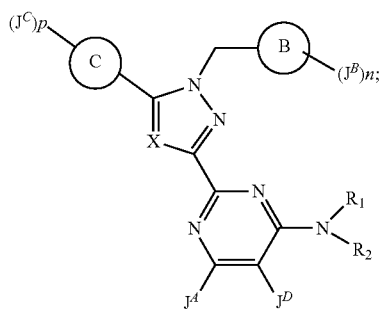

Formula IA wherein:
X is selected from N, CH, C($C_{1-4}$ alkyl), C($C_{1-4}$ haloalkyl), CCl and CF;
ring B is a phenyl or a 6-membered heteroaryl ring containing 1 or 2 ring nitrogen atoms, or ring B is a thiophene;
n is 0 or an integer selected from 1 to 3;
each $J^B$ is independently halogen, —CN, a $C_{1-6}$ aliphatic, —$OR^B$ or a $C_{3-8}$ cycloaliphatic ring; wherein each of said $C_{1-6}$ aliphatic and each of said $C_{3-8}$ cycloaliphatic group is optionally substituted with up to 3 instances of halogen;
each $R^B$ is independently hydrogen, a $C_{1-6}$ aliphatic or a $C_{3-8}$ cycloaliphatic ring; wherein each of said $R^B$ that is a $C_{1-6}$ aliphatic and each of said $R^B$ that is a $C_{3-8}$ cycloaliphatic ring is optionally substituted with up to 3 instances of halogen;
$J^A$ is hydrogen, halogen, methyl, methoxy, trifluoromethyl, trifluoromethoxy or —$NR^aR^b$, wherein $R^a$ and $R^b$ are each independently selected from hydrogen, $C_{1-6}$ alkyl or a 3-6 cycloalkyl ring;
$J^D$ is hydrogen, halogen, —CN, —$CF_3$, methoxy, trifluoromethoxy, nitro, amino or methyl;
$R^1$ and $R^2$, together with the nitrogen atom to which they are attached, form a 4 to 8-membered heterocyclic ring or 5 or 6-membered heteroaryl ring; wherein said 4 to 8-membered heterocyclic ring or said 5 or 6-membered heteroaryl ring optionally contains in addition to the nitrogen atom to which $R^1$ and $R^2$ are attached, up to 3 ring heteroatoms independently selected from N, O or S, and is optionally substituted by up to 5 instances of $R^5$; or
alternatively, $R^1$ and $R^2$ are each independently selected from the group consisting of hydrogen, $C_{1-6}$ alkyl, a $C_{3-8}$ cycloalkyl ring, a 4 to 8-membered heterocyclic ring, a 5 or 6-membered heteroaryl and a $C_{1-6}$ alkyl-$R^Y$; wherein each of said 4 to 8-membered heterocyclic ring and each of said 5 or 6-membered heteroaryl ring contains up to 3 ring heteroatoms independently selected from N, O and S; and wherein each of said $C_{1-6}$ alkyl, each of said $C_{3-8}$ cycloalkyl ring, each of said 4 to 8-membered heterocyclic ring group, each of said 5 or 6-membered heteroaryl and each of said $C_{1-6}$ alkyl portion of each said $C_{1-6}$ alkyl-$R^Y$ is optionally and independently substituted with up to 5 instances of $R^{5a}$; provided that $R^1$ and $R^2$ are not simultaneously hydrogen; and provided than when X is one of CH, C($C_{1-4}$ alkyl), C($C_{1-4}$ haloalkyl), CCl or CF, neither of $R^1$ and $R^2$ is a pyridine or a pyrimidine; or
alternatively, $J^D$ and one of $R^1$ or $R^2$ can form a 5-6 membered heterocyclic ring containing up to two heteroatoms selected from O, N and S and optionally substituted with up to 3 instances of oxo or —(Y)—$R^9$ wherein Y is either absent or is a linkage in the form of a $C_{1-6}$ alkyl chain optionally substituted by up to 6 instances of fluoro;
each $R^9$ is independently selected from the group consisting of hydrogen, fluoro, —CN, —$OR^{10}$, —$SR^{10}$, —$COR^{10}$, —$OC(O)R^{10}$, —$C(O)OR^{10}$, —$C(O)N(R^{10})_2$, —$C(O)N(R^{10})SO_2R^o$, —$N(R^{10})C(O)R^{10}$, —$N(R^{10})C(O)OR^{10}$, —$N(R^{10})C(O)N(R^{10})_2$, —$N(R^{10})_2$, —$SO_2R^{10}$, —$SO_2N(R^{10})_2$, —$SO_2N(R^{10})COOR^{10}$, —$SO_2N(R^{10})C(O)R^{10}$, —$N(R^{10})SO_2R^{10}$, —(C=O)$NHOR^{10}$, a $C_{3-6}$ cycloalkyl ring, a 4-8-membered heterocyclic ring and a 5-6 membered heteroaryl ring; wherein each said 4 to 8-membered heterocyclic ring and each said 5 to 6-membered heteroaromatic ring contains up to 4 ring heteroatoms independently selected from N, O or S; and wherein each said $C_{3-6}$ cycloalkyl ring, each said 4 to 8-membered heterocyclic ring and each said 5 to 6-membered heteroaromatic ring is optionally substituted with up to 3 instances of $R^{11}$;
each $R^{11}$ is independently selected from the group consisting of halogen, $C_{1-6}$ alkyl, —CN, —$OR^{12}$, —$SR^{12}$, —$COR^{12}$, —$OC(O)R^{12}$, —$C(O)OR^{12}$, —$C(O)N(R^{12})_2$, —$C(O)N(R^{12})SO_2R^{12}$, —$N(R^{12})C(O)R^{12}$, —$N(R^{12})C(O)OR^{12}$, —$N(R^{12})C(O)N(R^{12})_2$, —$N(R^{12})_2$, —$SO_2R^{12}$, —$SO_2N(R^{12})_2$, —$SO_2N(R^{12})COOR^{12}$, —$SO_2N(R^{12})C(O)R^{12}$, —$N(R^{12})SO_2R^{12}$ and —N=$OR^{12}$; wherein each of said $C_{1-6}$ alkyl is optionally and independently substituted by up to 3 instances of fluoro, —OH, —O($C_{1-4}$ alkyl), phenyl or —O($C_{1-4}$ fluoroalkyl)

wherein each $R^{10}$ is independently selected from the group consisting of hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each 5 or 6-membered heteroaryl ring and each said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$(fluoroalkyl), —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo; and wherein each $R^{12}$ is independently selected from the group consisting of hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each 5 or 6-membered heteroaryl ring and each said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$(fluoroalkyl), —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo;

$R^Y$ is selected from the group consisting of a $C_{3-8}$ cycloalkyl ring, a 4 to 8-membered heterocyclic ring, phenyl, and a 5 to 6-membered heteroaromatic ring; wherein each of said 4 to 8-membered heterocyclic ring and each of said 5 to 6-membered heteroaromatic ring contains up to 4 ring heteroatoms independently selected from N, O and S; and wherein each of said $C_{3-8}$ cycloalkyl ring, each of said 4 to 8-membered heterocyclic ring, each of said phenyl, and each of said 5 to 6-membered heteroaromatic ring is optionally substituted with up to 5 instances of $R^{5c}$;

each $R^{5c}$ is independently selected from the group consisting of halogen, —CN, $C_{1-6}$ alkyl, —$OR^{6b}$, —$SR^{6b}$, —$COR^{6b}$, —OC(O)$R^{6b}$, —C(O)$OR^{6b}$, —C(O)N($R^{6b}$)$_2$, —C(O)N($R^{6b}$)$SO_2R^{6b}$, —N($R^{6b}$)C(O)$R^{6b}$, —N($R^{6b}$)C(O)$OR^{6b}$, —N($R^{6b}$)C(O)N($R^{6b}$)$_2$, —N($R^{6b}$)$_2$, —$SO_2R^{6b}$, —$SO_2$N($R^{6b}$)$_2$, —$SO_2$N($R^{6b}$)COO$R^{6b}$, —$SO_2$N($R^{6b}$)C(O)$R^{6b}$, —N($R^{6b}$)$SO_2R^{6b}$, —(C=O)NHO$R^{6b}$, a $C_{3-8}$ cycloalkyl ring, a 4 to 7-membered heterocyclic ring, a 5 or 6-membered heteroaryl ring, phenyl, benzyl, an oxo group, and a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O and S; and wherein said bicyclic group is optionally and independently substituted by up to six instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{6b}$ is independently selected from the group consisting of hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each 5 or 6-membered heteroaryl ring and each of said 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; or two instances of $R^{5c}$ attached to the same or different ring atoms of $R^Y$, together with said ring atom or atoms, may form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O and S; and wherein said $C_{3-8}$ cycloalkyl ring, 4 to 6-membered heterocyclic ring, phenyl or a 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR"(CO)CO($C_{1-4}$ alkyl), —OH or halogen; wherein R" is hydrogen or a $C_{1-2}$ alkyl;

each $R^{5a}$ is independently selected from the group consisting of halogen, —CN, $C_{1-6}$ alkyl, —$OR^{6a}$, —$SR^{6a}$, —$COR^{6a}$, —OC(O)$R^{6a}$, —C(O)$OR^{6a}$, —C(O)N($R^{6a}$)$_2$, —C(O)N($R^{6a}$)$SO_2R^{6a}$—N($R^{6a}$)C(O)$R^{6a}$—N($R^{6a}$)C(O)$OR^{6a}$, —N($R^{6a}$)C(O)N($R^{6a}$)$_2$, —N($R^{6a}$)$_2$, —$SO_2R^{6a}$, —$SO_2$N($R^{6a}$)$_2$, —$SO_2$N($R^{6a}$)COO$R^{6a}$, —$SO_2$N($R^{6a}$)C(O)$R^{6a}$, —N($R^{6a}$)$SO_2R^{6a}$, —(C=O)NHO$R^{6a}$, a $C_{3-8}$ cycloalkyl ring, a 4 to 7-membered heterocyclic ring, a 5 or 6-membered heteroaryl ring, phenyl, benzyl, an oxo group and a bicyclic group; wherein each 5 or 6-membered heteroaryl ring and each of said 4 to 7-membered heterocyclic ring contains up to 4 ring heteroatoms independently selected from N, O and S, wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O and S; and wherein said bicyclic group is optionally and independently substituted by up to six instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{6a}$ is independently selected from the group consisting of hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —C(O)$NH_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S; or when one of $R^1$ or $R^2$ is the $C_{3-8}$ cycloalkyl ring, 4 to 8-membered heterocyclic ring or 5 or 6-membered heteroaryl substituted with up to 5 instances of $R^{5a}$, two of the instances of $R^{5a}$ attached to the same or different ring atoms of said $R^1$ or $R^2$, together with said atom or atoms, may optionally form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O and S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)CO($C_{1-4}$ alkyl), —NR'(CO)CO($C_{1-4}$ alkyl) or halogen; wherein R' is hydrogen or a $C_{1-2}$ alkyl;

each $R^5$ is independently selected from the group consisting of halogen, —CN, $C_{1-6}$ alkyl, —$OR^6$, —$SR^6$, —$COR^6$, —OC(O)$R^6$, —C(O)$OR^6$, —C(O)N($R^6$)$_2$, —C(O)N($R^6$)$SO_2R^6$, —N($R^6$)C(O)$R^6$, —N($R^6$)C(O)$OR^6$, —N($R^6$)C(O)N($R^6$)$_2$, —N($R^6$)$_2$, —$SO_2R^6$, —$SO_2$N($R^6$)$_2$, —$SO_2$N($R^6$)$COOR^6$, —$SO_2$N($R^6$)C(O)$R^6$, —N($R^6$)$SO_2R^6$, —(C═O)$NHOR^6$, a $C_{3-8}$ cycloalkyl ring, a 4 to 7-membered heterocyclic ring, a 5 or 6-membered heteroaryl ring, phenyl, benzyl, an oxo group and a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said $C_{3-8}$ cycloalkyl ring, each of said 4 to 7-membered heterocyclic ring, each of said 5 or 6-membered heteroaryl ring, each said benzyl or each said phenyl group is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O and S; and wherein said bicyclic group is optionally and independently substituted by up to six instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^6$ is independently selected from the group consisting of hydrogen, a $C_{1-6}$ alkyl, phenyl, benzyl, a $C_{3-8}$ cycloalkyl ring or a 4 to 7-membered heterocyclic ring, and a 5 or 6-membered heteroaryl ring; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —$NH_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; or when $R^1$ and $R^2$ attached to the nitrogen atom form the 4 to 8-membered heterocyclic ring or 5 or 6-membered heteroaryl ring substituted with up to 5 instances of $R^5$, two of the instances of $R^5$ attached to the same or different atoms of said ring, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O and S; and wherein said $C_{3-8}$ cycloalkyl ring, said 4 to 6-membered heterocyclic ring, said phenyl or said 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen; wherein R is hydrogen or a $C_{1-2}$ alkyl;

p is an integer selected from 0, 1 or 2;

ring C is a monocyclic 5-membered heteroaryl ring containing up to 4 ring heteroatoms selected from N, O or S; wherein said monocyclic 5-membered heteroaryl ring is not a 1,3,5-triazinyl ring;

each $J^C$ is independently halogen or a $C_{1-4}$ aliphatic optionally and independently substituted by up to 3 instances of $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen.

In other embodiments of the above methods, uses and compositions, the sGC stimulator is a compound having Formula IB, or a pharmaceutically acceptable salt thereof, Formula IB

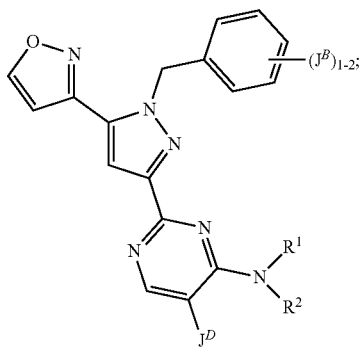

wherein $J^D$ is hydrogen or halogen; $J^B$ is halogen and
$R^1$ and $R^2$, together with the nitrogen atom to which they are attached, form a 4 to 8-membered heterocyclic ring or 5-membered heteroaryl ring; wherein said 4 to 8-membered heterocyclic ring or said 5-membered heteroaryl ring optionally contains, in addition to the nitrogen atom to which $R^1$ and $R^2$ are attached, up to 3 ring heteroatoms independently selected from N, O and S, and is optionally substituted by up to 5 instances of $R^{5e}$;
each $R^{5e}$ is independently selected from the group consisting of halogen, —CN, $C_{1-6}$ alkyl, —($C_{1-4}$ alkyl)-$R^6$, a $C_{3-8}$ cycloalkyl ring, $C_{1-4}$ cyanoalkyl, —$OR^6$, —$SR^6$, —$OCOR^6$, —$COR^6$, —$C(O)OR^6$, —$C(O)N(R^6)_2$, —$N(R^6)C(O)R^6$, —$N(R^6)_2$, —$SO_2R^6$, —$SO_2OH$, —$SO_2NHOH$, —$SO_2N(R^6)COR^6$, —$SO_2N(R^6)_2$, —$N(R^6)SO_2R^6$, benzyl, phenyl and an oxo group; wherein each said phenyl ring and each said benzyl group, is optionally and independently substituted with up to 3 instances of halogen, —OH, —$NH_2$, —NH($C_{1-4}$ alkyl), —$N(C_{1-4}$ alkyl$)_2$, —CN, $C_{1-4}$ alkyl, $C_{1-4}$ haloalkyl, —$O(C_{1-4}$ alkyl) or —$O(C_{1-4}$ haloalkyl); and wherein each said $C_{1-6}$ alkyl, each $C_{1-4}$ alkyl portion of said —($C_{1-4}$ alkyl)-$R^6$ moiety, and each said $C_{3-8}$ cycloalkyl ring is optionally and independently substituted with up to 3 instances of halogen; wherein
each $R^6$ is independently selected from the group consisting of hydrogen, a $C_{1-6}$ alkyl, a $C_{2-4}$ alkenyl, phenyl, benzyl, and a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;
two of the instances of $R^{5e}$ attached to the same or different atoms of said ring formed by $R^1$, $R^2$ and the nitrogen to which $R^1$ and $R^2$ are attached, together with said atom or atoms, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —$C(O)O(C_{1-4}$ alkyl), —$C(O)OH$, —$C(O)NH_2$, —$NR(CO)O(C_{1-4}$ alkyl), —OH or halogen; wherein R is hydrogen or a $C_{1-2}$ alkyl;
alternatively, $R^1$ and $R^2$ are each independently selected from the group consisting of hydrogen, $C_{1-6}$ alkyl, a $C_{3-8}$ cycloalkyl ring, a 4 to 10-membered heterocyclic ring, a 5 or 6-membered heteroaryl, phenyl and a $C_{1-6}$ alkyl-$R^Y$; wherein each of said 4 to 10-membered heterocyclic ring and each of said 5 or 6-membered heteroaryl ring contains up to 3 ring heteroatoms independently selected from N, O and S; and wherein each of said $C_{1-6}$ alkyl, each of said $C_{1-6}$ alkyl portion of each said $C_{1-6}$ alkyl-$R^Y$ moiety, each of said $C_{3-8}$ cycloalkyl ring, each of said 4 to 10-membered heterocyclic ring group, each of said 5 or 6-membered heteroaryl, each of said phenyl is optionally and independently substituted with up to 5 instances of $R^{5f}$; provided that neither of $R^1$ or $R^2$ are pyridine or pyrimidine;
$R^Y$ is a $C_{3-8}$ cycloalkyl ring, a 4 to 8-membered heterocyclic ring, phenyl, or a 5 to 6-membered heteroaryl ring; wherein each of said 4 to 8-membered heterocyclic ring and each of said 5 to 6-membered heteroaromatic ring contains between 1 and 4 ring heteroatoms independently selected from N, O and S; and wherein each of said $C_{3-8}$ cycloalkyl ring, each of said 4 to 8-membered heterocyclic ring, each of said phenyl, and each of said 5 to 6-membered heteroaryl ring is optionally substituted with up to 5 instances of $R^{5g}$;
each $R^{5f}$ is independently selected from the group consisting of halogen, —CN, $C_{1-6}$ alkyl, —($C_{1-4}$ alkyl)-$R^{6a}$, a $C_{7-12}$ aralkyl, $C_{3-8}$ cycloalkyl ring, $C_{1-4}$ cyanoalkyl, —$OR^{6a}$, —$SR^{6a}$, —$OCOR^{6a}$, —$COR^{6a}$, —$C(O)OR^{6a}$, —$C(O)N(R^{6a})_2$, —$N(R^{6a})C(O)R^{6a}$, —$N(R^{6a})_2$, —$SO_2R^{6a}$, —$SO_2N(R^{6a})_2$, —$N(R^{6a})SO_2R^{6a}$, —$SO_2OH$, —$SO_2NHOH$, —$SO_2N(R^{6a})COR^{6a}$, phenyl and an oxo group; wherein each said phenyl group is optionally and independently substituted with up to 3 instances of halogen, —OH, —$NH_2$, —NH($C_{1-4}$ alkyl), —$N(C_{1-4}$ alkyl$)_2$, —$NO_2$, —CN, $C_{1-4}$ alkyl, $C_{1-4}$ haloalkyl, —$O(C_{1-4}$ alkyl) or —$O(C_{1-4}$ haloalkyl); and wherein each said $C_{7-12}$ aralkyl, each said $C_{1-6}$ alkyl, each said $C_{1-4}$ alkyl portion of each said —($C_{1-4}$ alkyl)-$R^{6a}$ and each said $C_{3-8}$ cycloalkyl group is optionally and independently substituted with up to three instances of halogen;
each $R^{6a}$ is independently hydrogen, a $C_{1-6}$ alkyl, a $C_{2-4}$ alkenyl, phenyl, benzyl, or a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;
when one of $R^1$ or $R^2$ is the $C_{3-8}$ cycloalkyl ring, 4 to 8-membered heterocyclic ring or 5 or 6-membered heteroaryl substituted with up to 5 instances of $R^5$, two of the instances of $R^5$ attached to the same or different ring atoms of said $R^1$ or $R^2$, together with said atom or atoms, form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O and S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)O($C_{1-4}$ alkyl), —NR'(CO)O($C_{1-4}$ alkyl) or halogen; wherein R' is hydrogen or a $C_{1-2}$ alkyl;

each $R^{5g}$ is independently selected from the group consisting of halogen, —CN, $C_{1-6}$ alkyl, —($C_{1-4}$ alkyl)-$R^{6b}$, a benzyl, $C_{3-8}$ cycloalkyl ring, $C_{1-4}$ cyanoalkyl, —$OR^{6b}$, —$SR^{6b}$, —$OCOR^{6b}$, —$COR^{6b}$, —C(O)$OR^{6b}$, —C(O)N($R^{6b})_2$, —N($R^{6b}$)C(O)$R^{6b}$, —N($R^{6b})_2$, —$SO_2R^{6b}$, —$SO_2$N($R^{6b})_2$, —N($R^{6b}$)$SO_2R^{6b}$, —$SO_2$OH, —$SO_2$NHOH, —$SO_2$N($R^{6b}$)$COR^{6b}$, phenyl and an oxo group; wherein each said phenyl and each said benzyl group is optionally and independently substituted with up to 3 instances of halogen, —OH, —$NH_2$, —NH($C_{1-4}$ alkyl), —N($C_{1-4}$ alkyl)$_2$, —$NO_2$, —CN, $C_{1-4}$ alkyl, $C_{1-4}$ haloalkyl, —O($C_{1-4}$ alkyl) or —O($C_{1-4}$ haloalkyl); and wherein each said $C_{1-6}$ alkyl, $C_{1-4}$ alkyl portion of each said ($C_{1-4}$ alkyl)-$R^{6b}$ moiety and each said $C_{3-8}$ cycloalkyl group is optionally and independently substituted with up to 3 instances of halogen;

each $R^{6b}$ is independently selected from the group consisting of hydrogen, a $C_{1-6}$ alkyl, a $C_{2-4}$ alkenyl, phenyl, benzyl, and a $C_{3-8}$ cycloalkyl ring; wherein each said $C_{1-6}$ alkyl, each said $C_{2-4}$ alkenyl, each said phenyl, each said benzyl and each said $C_{3-8}$ cycloalkyl group is optionally and independently substituted with up to 3 instances of halogen;

alternatively, two instances of $R^5$ attached to the same or different ring atoms of $R^Y$, together with said ring atom or atoms, form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)$NH_2$, —NR"(CO)O($C_{1-4}$ alkyl), —OH or halogen; and R" is hydrogen or a $C_{1-2}$ alkyl.

In some embodiments of the above methods, uses and compositions, the sGC stimulator is a compound of Formula IC, or a pharmaceutically acceptable salt thereof:

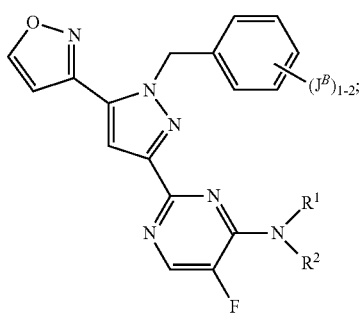

Formula IC wherein $J^B$ is halogen;

$R^1$ is hydrogen or $C_{1-6}$ alkyl;

$R^2$ is a $C_{1-6}$ alkyl group optionally and independently substituted by up to three instances of $R^{5a}$, wherein $R^{5a}$ has been defined in previous paragraphs as part of the description of Formula IA.

In some embodiments of the above methods, uses and compositions, the sGC stimulator is a compound of the following formula:

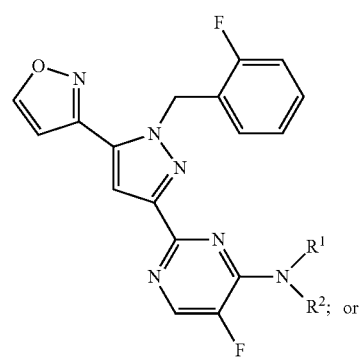

Formula IC-a or

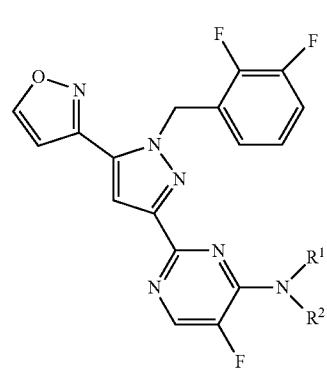

Formula IC-b or a pharmaceutically acceptable salt thereof, wherein the variables are as defined for Formula IC.

In some embodiment, for compounds of Formula IC, Formula IC-a or Formula IC-b, $R^1$ is hydrogen.

In some embodiment, for compounds of Formula IC, Formula IC-a or Formula IC-b, $R^{5a}$ is $C_{1-4}$alkyl, $C_{1-4}$haloalkyl, —OH, or —C(=O)$NH_2$. In some embodiments, for compounds of Formula IC, Formula IC-a or Formula IC-b, $R^{5a}$ is methyl, $CF_3$, —OH or —C(=O)$NH_2$.

In some embodiments of the above methods, uses and compositions, the sGC stimulator is a compound selected from those depicted below, or a pharmaceutically acceptable salt thereof:

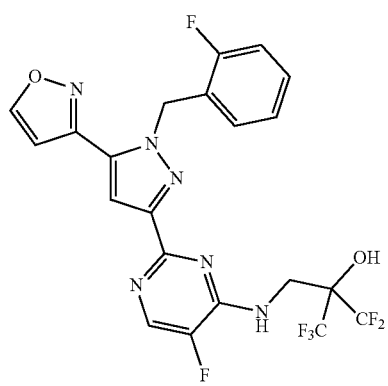
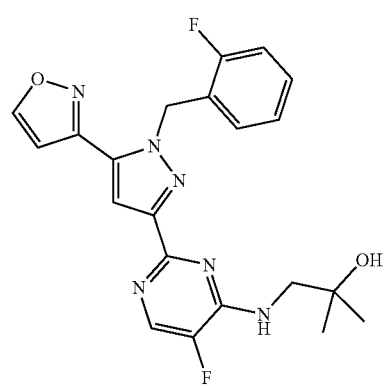
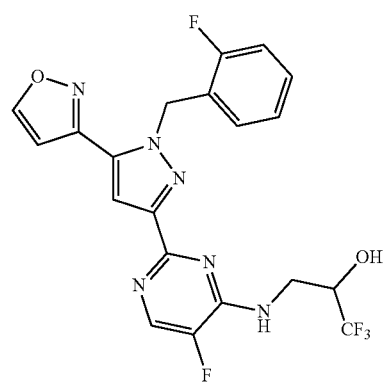
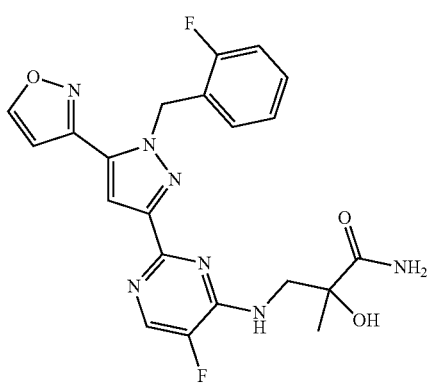
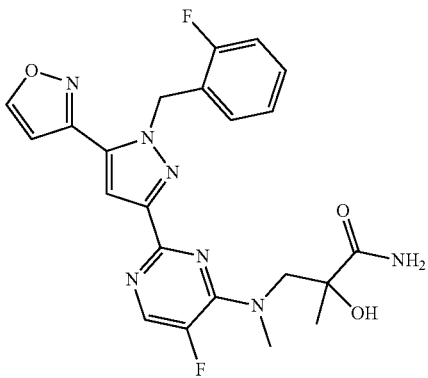
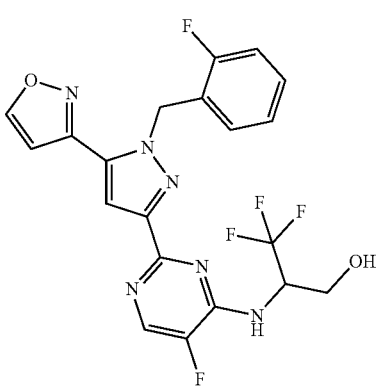
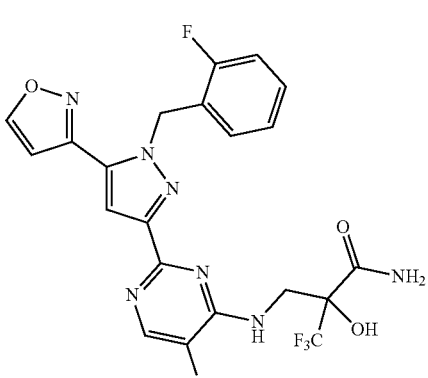
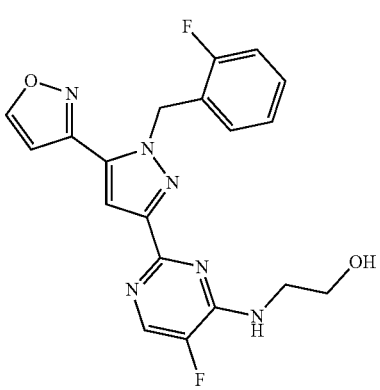

27
-continued
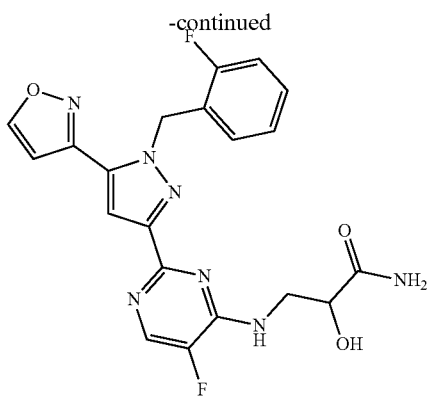
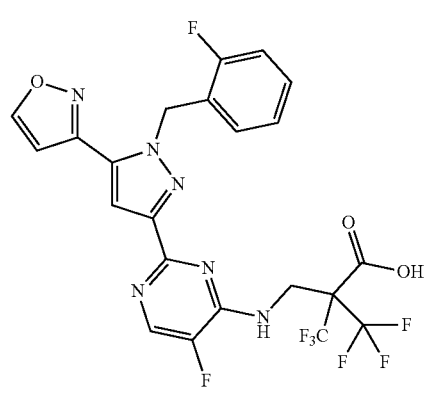
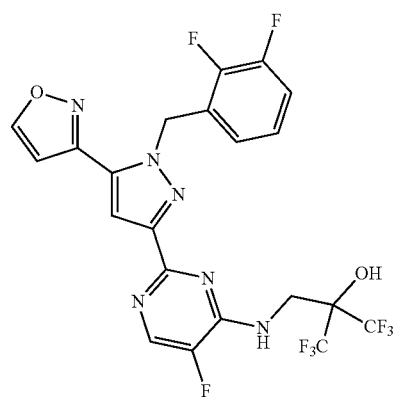
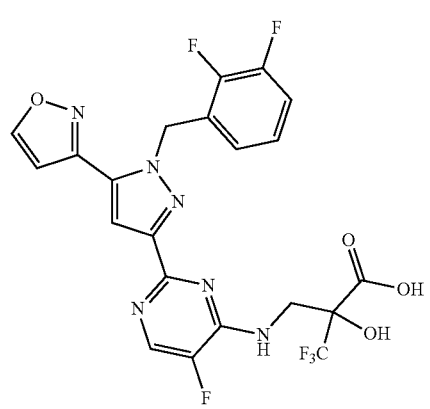
28
-continued
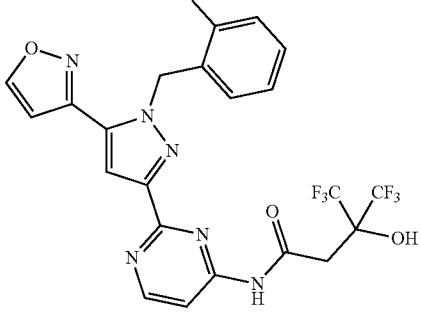
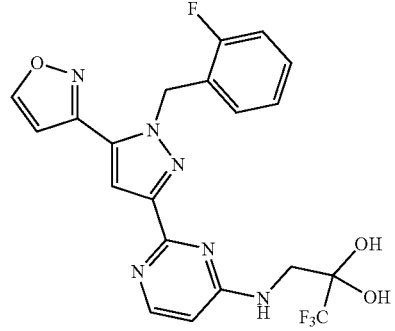
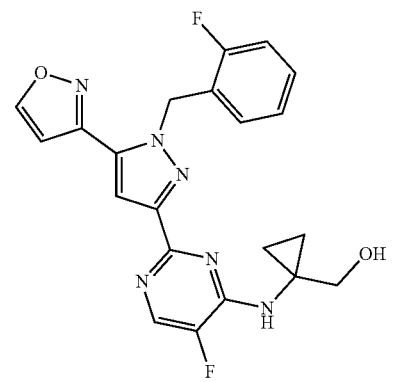
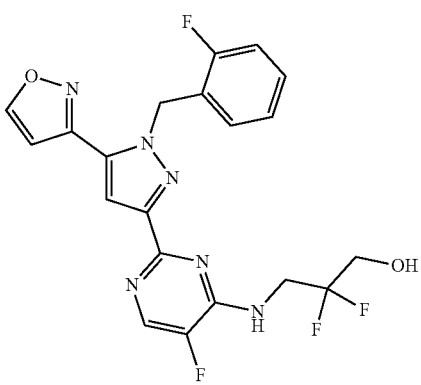

-continued

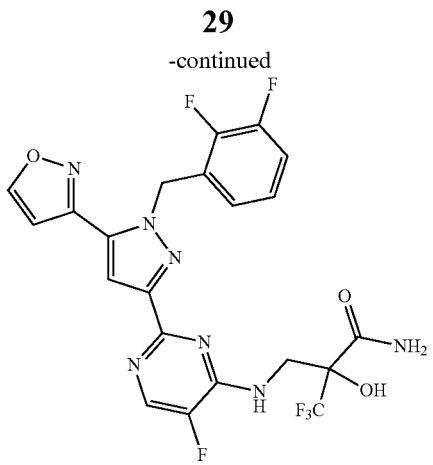

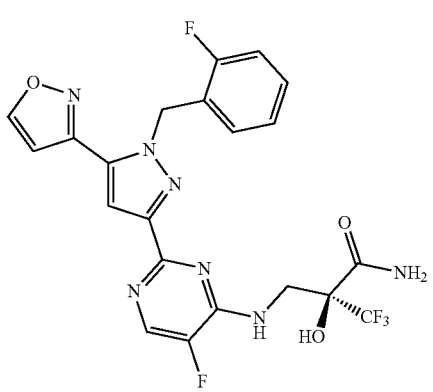

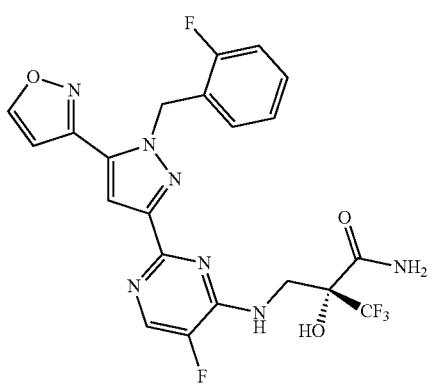

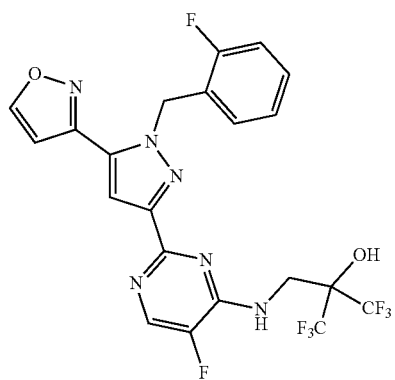

-continued

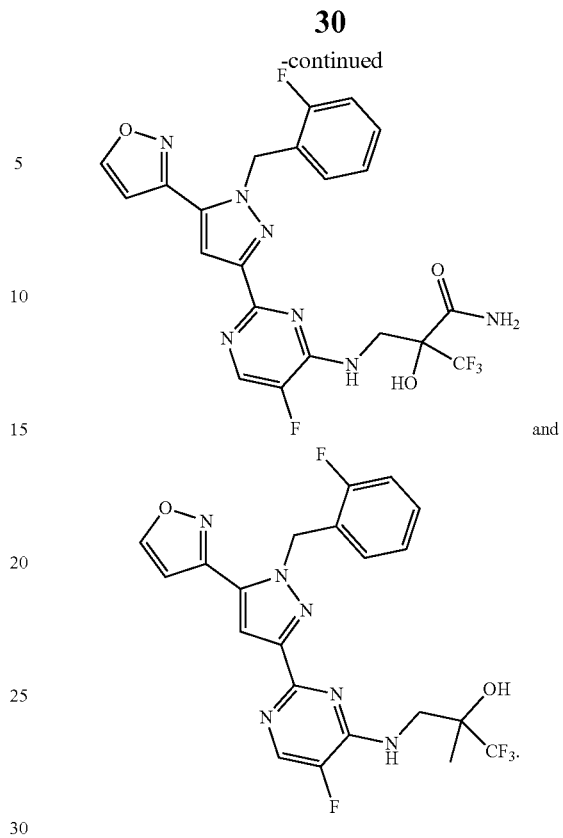

and

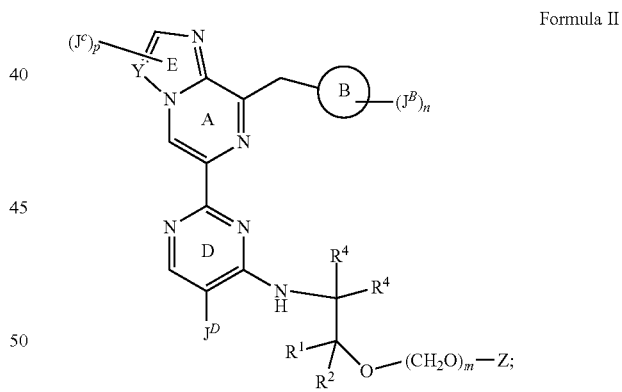

In some embodiments of the above methods, uses and compositions, the sGC stimulator is a compound of the following formula, or a pharmaceutically acceptable salt thereof:

Formula II wherein:
Y is independently N or C;
ring B is a phenyl or a 5 or 6-membered heteroaryl ring, containing 1 or 2 ring heteroatoms independently selected from N, O or S;
n is an integer selected from 0 to 3; and each $J^B$ is independently halogen, —CN, a $C_{1-6}$ aliphatic, —$OR^B$ or a $C_{3-8}$ cycloaliphatic ring;
wherein each $J^B$ that is a $C_{1-6}$ aliphatic and each $J^B$ that is a $C_{3-8}$ cycloaliphatic ring is optionally and independently substituted with up to 3 instances of $R^3$;
each $R^B$ is independently hydrogen, a $C_{1-6}$ aliphatic or a $C_{3-8}$ cycloaliphatic ring; said $R^B$ optionally and independently substituted with up to 3 instances of $R^{3a}$;

each $R^3$ and $R^{3a}$ is, in each instance, independently halogen, —CN, $C_{1-4}$ alkyl, $C_{1-4}$ haloalkyl, —O($C_{1-4}$ alkyl) or —O($C_{1-4}$ haloalkyl);

Z is selected from the group consisting of hydrogen, —P(O)(OH)$_2$, —P(O)(OH)O$^-$M$^+$, —P(O)(O$^-$)$_2$(M$^+$)$_2$, —P(O)(O$^-$)$_2$D$^{2+}$ and —P(O)(O-Benzyl)$_2$; wherein M$^+$ is a pharmaceutically acceptable monovalent cation and D$^{2+}$ is a pharmaceutically acceptable divalent cation;

m is 0 or 1;

$R^1$ is $C_{1-4}$ alkyl, $C_{1-4}$ fluoroalkyl, —C(O)NH$_2$ or hydrogen; and $R^2$ is $C_{1-4}$ alkyl, $C_{1-4}$ fluoroalkyl or hydrogen;

both instances of $R^4$ are simultaneously hydrogen or both instances of $R^4$, together with the carbon atom to which they are attached form a carbonyl group;

$J^D$ is hydrogen, halogen, methoxy or —CN p is 1, 2 or 3; and each $J^C$ is independently hydrogen, halogen, $C_{1-4}$ aliphatic, $C_{1-4}$ alkoxy or —CN; wherein each said $C_{1-4}$ aliphatic and each said $C_{1-4}$ alkoxy is optionally and independently substituted by up to 3 instances of $C_{1-4}$ alkoxy, $C_{1-4}$ haloalkoxy, —OH or halogen.

In some embodiments of the above methods, uses and compositions, the sGC stimulator is a compound of of Formula IIA, or a pharmaceutically acceptable salt thereof:

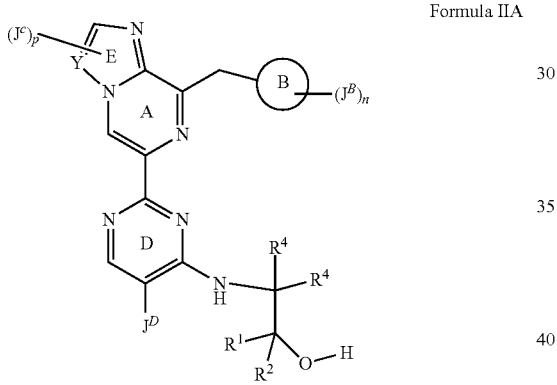

Formula IIA

For Formula IIA, the definitions of all variables are the same as those presented for Formula II.

In some embodiments of the above methods, uses and compositions, the sGC stimulator is a compound of Formula IIIA, Formula IIIB, Formula IVA, Formula IVB, Formula VA, Formula VB, Formula VIA, or Formula VIB, or a pharmaceutically acceptable salt thereof:

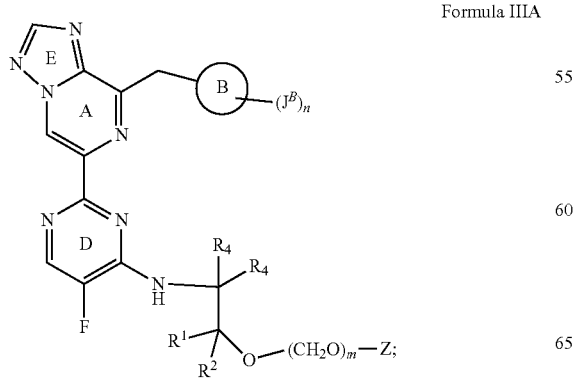

Formula IIIA

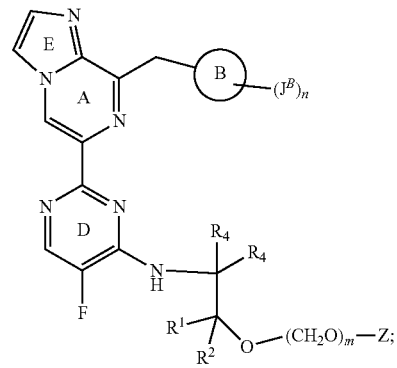

Formula IIIB

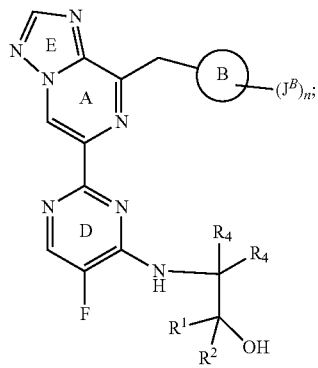

Formula IVA

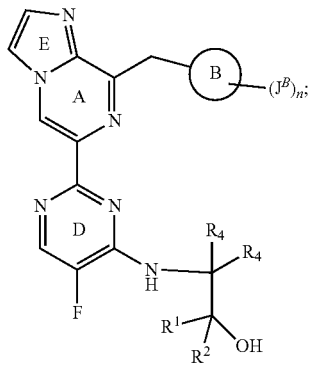

Formula IVB

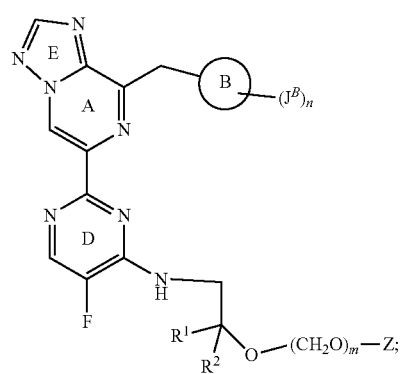

Formula VA

-continued
Formula VIA
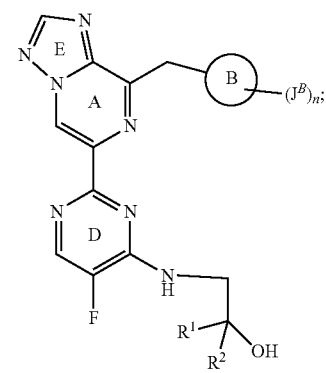
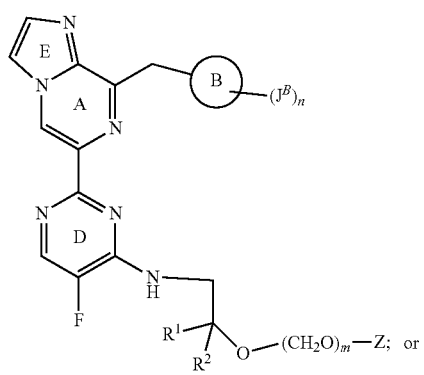
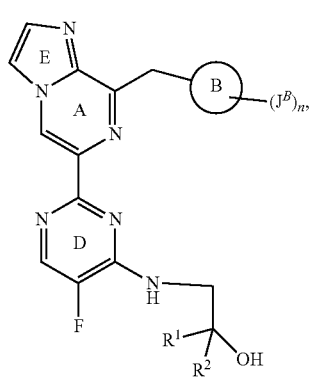
wherein the definitions for the variables are as same as those described for Formula II.
In some embodiments of the above methods, uses and compositions, the sGC stimulator is a compound of Formula II and is selected from those listed in Table below.
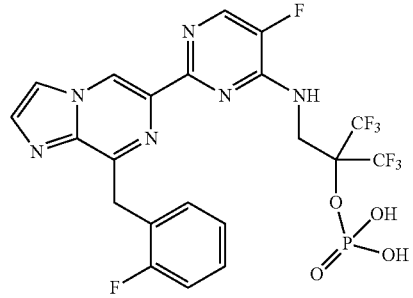 [SMILES: O=P(O)(O)OC(CNc1nc(-c2cn3ccnc3c(Cc3ccccc3F)n2)ncc1F)(C(F)(F)F)C(F)(F)F]
I-1
-continued
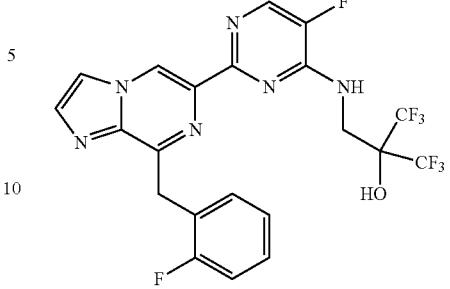
I-2
Formula VB
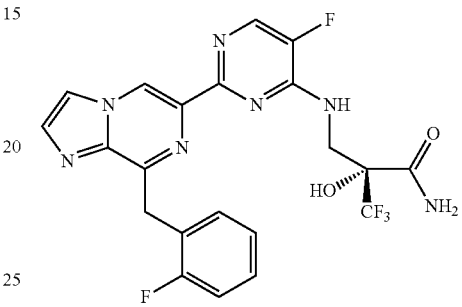
I-3
Formula VIB
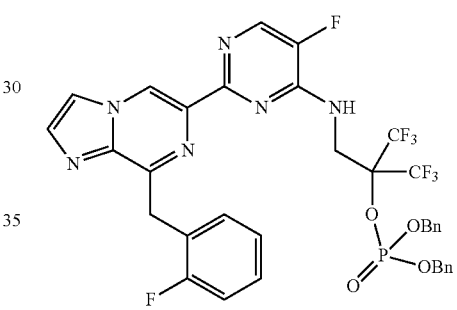
I-4
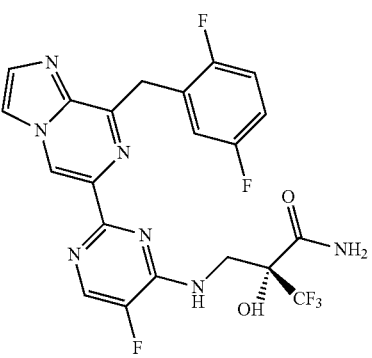 [SMILES: NC(=O)[C@](O)(CNc1nc(-c2cn3ccnc3c(Cc3cc(F)ccc3F)n2)ncc1F)C(F)(F)F]
I-5
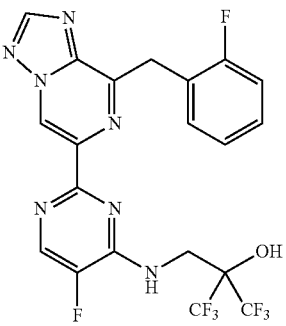 [SMILES: OC(CNc1nc(-c2cn3ncnc3c(Cc3ccccc3F)n2)ncc1F)(C(F)(F)F)C(F)(F)F]
I-6

-continued
I-7
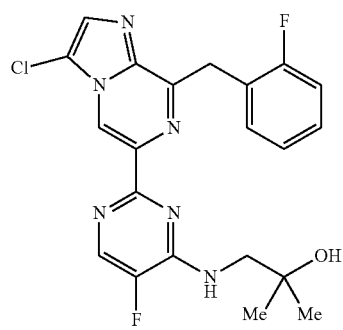 [SMILES: CC(C)(O)CNc1nc(-c2cn3c(Cl)cnc3c(Cc3ccccc3F)n2)ncc1F]
I-8
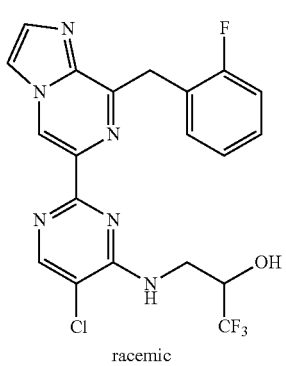 [SMILES: OC(CNc1nc(-c2cn3ccnc3c(Cc3ccccc3F)n2)ncc1Cl)C(F)(F)F]
racemic
I-9
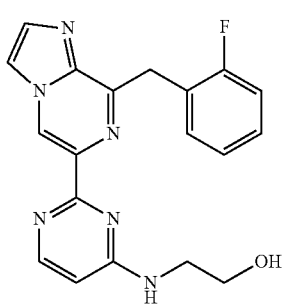 [SMILES: OCCNc1ccnc(-c2cn3ccnc3c(Cc3ccccc3F)n2)n1]
I-10
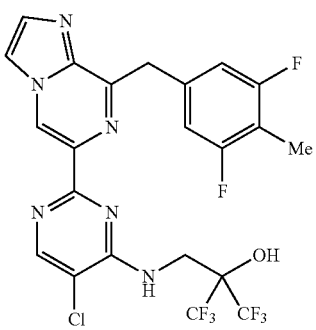 [SMILES: Cc1c(F)cc(Cc2nc(-c3ncc(Cl)c(NCC(O)(C(F)(F)F)C(F)(F)F)n3)cn3ccnc23)cc1F]
-continued
I-11
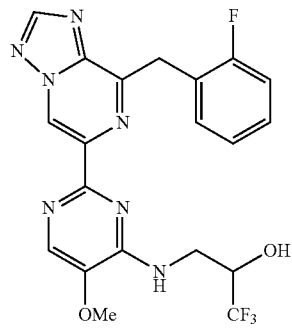
racemic
I-12
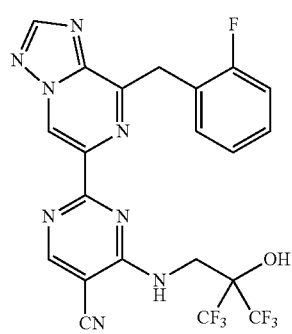 [SMILES: N#Cc1cnc(-c2cn3ncnc3c(Cc3ccccc3F)n2)nc1NCC(O)(C(F)(F)F)C(F)(F)F]
I-13
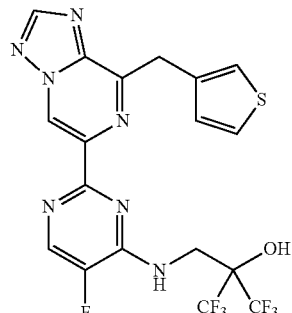
I-14
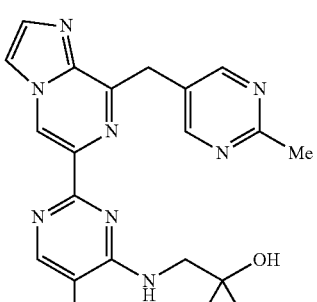
I-15
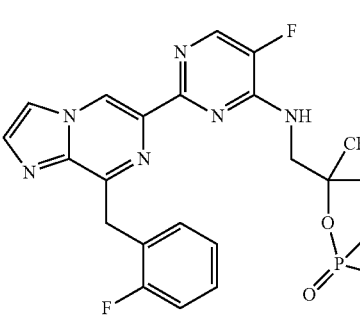

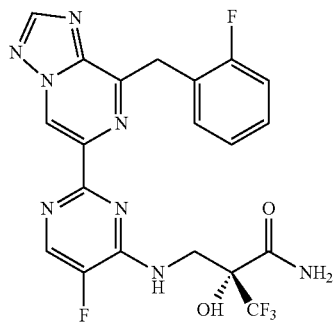 [SMILES: NC(=O)[C@](O)(CNc1nc(-c2cn3ncnc3c(Cc3ccccc3F)n2)ncc1F)C(F)(F)F]

I-16

In some embodiments of the above methods, uses and compositions, the sGC stimulator is a compound of the following formula, or a pharmaceutically acceptable salt thereof:

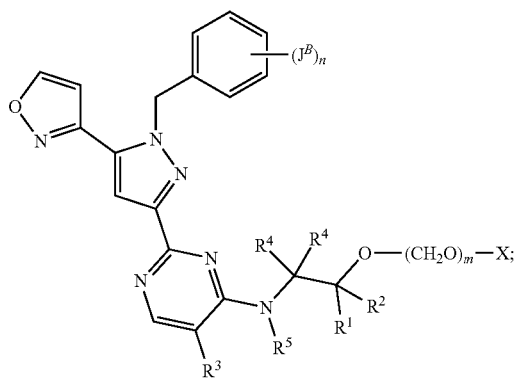

Formula L wherein,
- X is selected from —P(O)(OH)$_2$, —P(O)(OH)O$^-$M$^+$, —P(O)(O$^-$)$_2$(M$^+$)$_2$ or —P(O)(O$^-$)$_2$D$^{2+}$; wherein M$^+$ is a pharmaceutically acceptable monovalent cation and D$^{2+}$ is a pharmaceutically acceptable divalent cation;
- each J$^B$ is independently selected from halogen;
- m is selected from 0 or 1;
- n is selected from 0, 1, 2, 3 or 4;
- R$^1$ is selected from C$_{1-4}$ alkyl, C$_{1-4}$ fluoroalkyl, —C(O)NH$_2$ or hydrogen; and
- R$^2$ is selected from C$_{1-4}$ alkyl, C$_{1-4}$ fluoroalkyl or hydrogen; or, alternatively,
- R$^1$ and R$^2$, together with the carbon atom to which they are attached form an unsubstituted C$_{3-7}$ cycloaliphatic ring or an unsubstituted 3 to 7-membered heterocyclic ring, containing up to 2 heteroatoms independently selected from N, O or S;
- R$^3$ is selected from halogen, hydrogen, —CN or —NH$_2$; and
- both instances of R$^4$ are simultaneously hydrogen or both instances of R$^4$, together with the carbon atom to which they are attached form a carbonyl group; and
- R$^5$ is selected from hydrogen or methyl.

In some embodiments of the above methods, uses and compositions, the sGC stimulator is a compound of of Formula LA or LB or a pharmaceutically acceptable salt thereof:

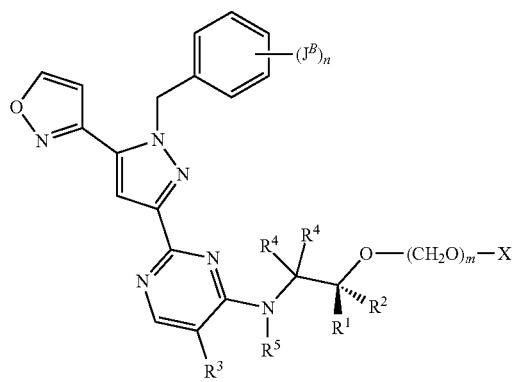

Formula LB

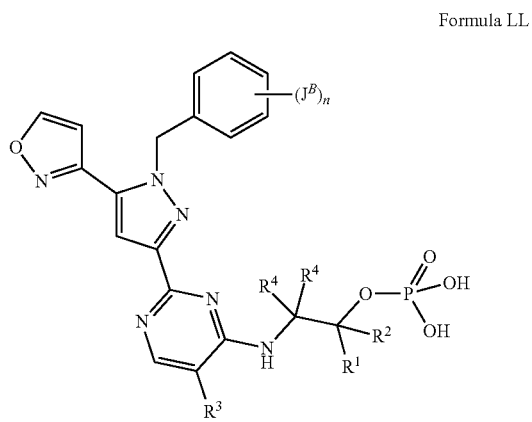

Formula LC wherein R$^1$ and R$^2$ are different, and the values of the variables are as defined for Formula L.

In some embodiments of the above methods, uses and compositions, the sGC stimulator is a compound of of Formula LL, LLA, LLB, LLL, LLLA, or LLLB or a pharmaceutically acceptable salt thereof:

Formula LL

Formula LLA
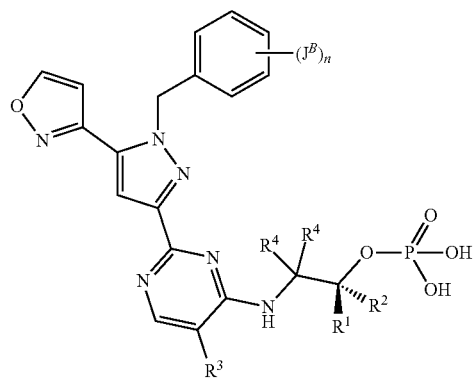
Formula LLB
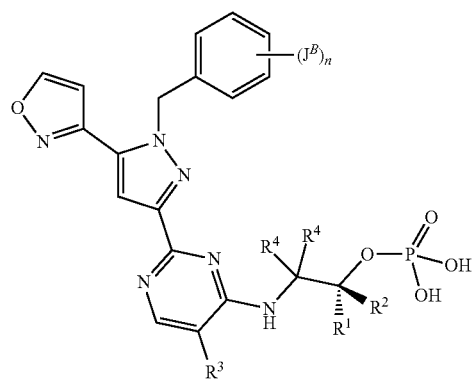
Formula LLL
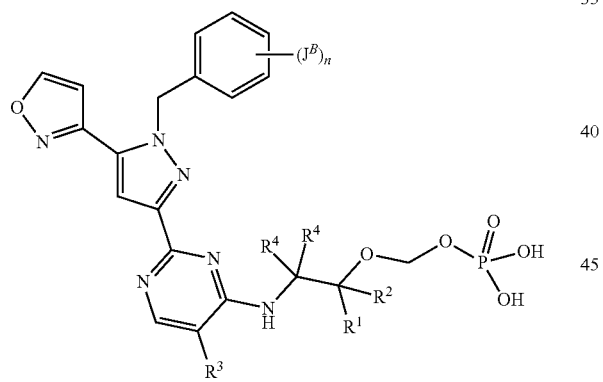
Formula LLLA
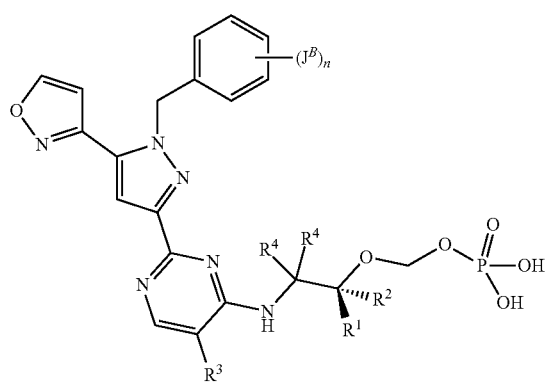
Formula LLLB
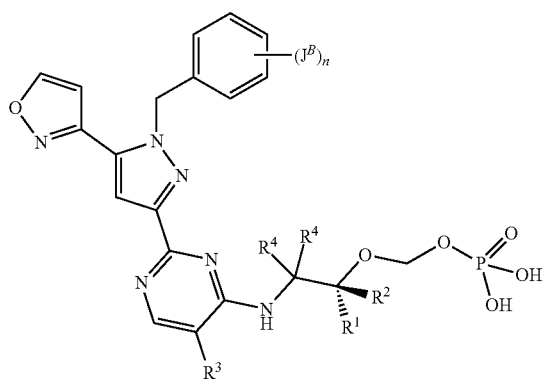
and the values of the variables are as defined for Formula L.
In some embodiments of the above methods, uses and compositions, the sGC stimulator is a compound of Formula II and is selected from those listed in Table below.
I-1
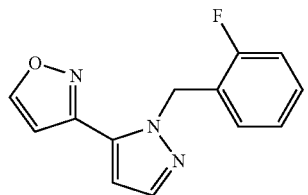
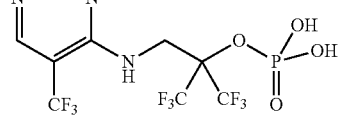
I-2
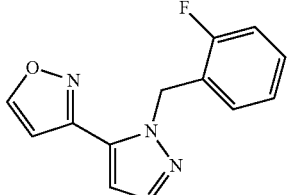
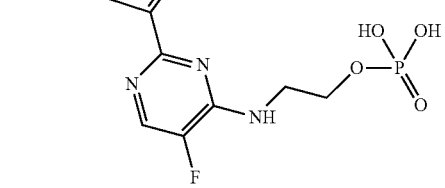

-continued

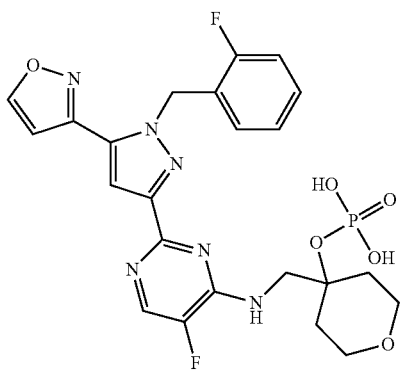 [SMILES: O=P(O)(O)OC1(CNc2nc(-c3cc(-c4ccon4)n(Cc4ccccc4F)n3)ncc2F)CCOCC1]

I-3

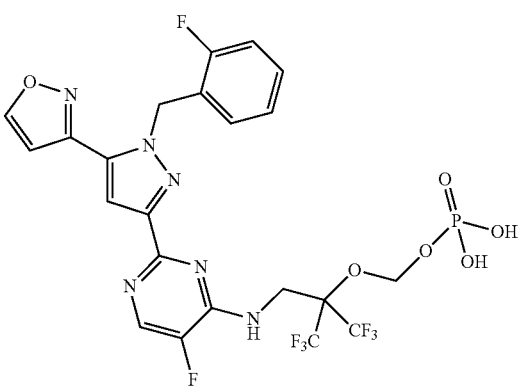 [SMILES: O=P(O)(O)OCOC(CNc1nc(-c2cc(-c3ccon3)n(Cc3ccccc3F)n2)ncc1F)(C(F)(F)F)C(F)(F)F]

I-4

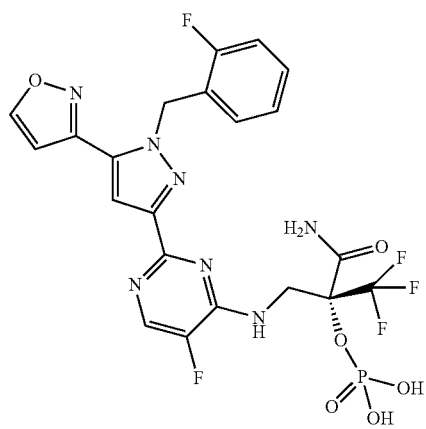 [SMILES: NC(=O)[C@@](CNc1nc(-c2cc(-c3ccon3)n(Cc3ccccc3F)n2)ncc1F)(OP(=O)(O)O)C(F)(F)F]

I-5

In some embodiments of the above methods, uses and compositions, the sGC stimulator is a compound of Formula XZ, or a pharmaceutically acceptable salt thereof:

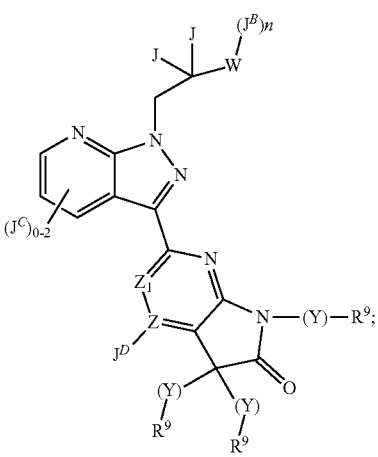

Formula XZ wherein:
W is either
i) absent, and $J^B$ is connected directly to the carbon atom bearing two J groups; each J is independently selected from hydrogen or methyl, n is 1 and $J^B$ is a $C_{2-7}$ alkyl chain optionally substituted by between 2 and 9 instances of fluorine; wherein, optionally, one —CH$_2$— unit of said $C_{2-7}$ alkyl chain can be replaced by —O— or —S—.
ii) a ring B selected from the group consisting of phenyl, a 5 or 6-membered heteroaryl ring, containing 1 or 2 ring heteroatoms independently selected from N, O and S, a $C_{3-7}$ cycloalkyl ring and a 4 to 7-membered heterocyclic compound, containing up to 3 heteroatoms independently selected from O, N and S;
wherein when W is ring B
each J is hydrogen;
n is 0 or an integer selected from 1, 2 or 3;
each $J^B$ is independently selected from the group consisting of halogen, —CN, a $C_{1-6}$ aliphatic, —OR$^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently hydrogen, a $C_{1-6}$ aliphatic or a $C_{3-8}$ cycloaliphatic; wherein each of said $R^B$ that is a $C_{1-6}$ aliphatic and each of said $R^B$ that is a $C_{3-8}$ cycloaliphatic ring is optionally and independently substituted with up to 3 instances of $R^{3a}$;
each $R^3$ is independently halogen, —CN, $C_{1-4}$ alkyl, $C_{1-4}$ haloalkyl, —O($C_{1-4}$ alkyl) or —O($C_{1-4}$ haloalkyl);
each $R^{3a}$ is independently halogen, —CN, $C_{1-4}$ alkyl, $C_{1-4}$ haloalkyl, —O($C_{1-4}$ alkyl) or —O($C_{1-4}$ haloalkyl);
$Z^1$ in ring D is CH or N; Z is C or N; wherein if $Z^1$ is CH, then Z must be C; and if $Z^1$ is N, then Z may be C or N;
each $J^D$ is independently selected from the group consisting of $J^A$-CN, —NO$_2$, —OR$^D$, —SR$^D$, —C(O)R$^D$, C(O)OR$^D$, —OC(O)R$^D$, C(O)N(R$^D$)$_2$, —N(R$^D$)$_2$, —N(R$^d$)C(O)R$^D$, —N(R$^d$)C(O)OR$^D$, —N(R$^d$)C(O)N $(R^D)_2$, —OC(O)N$(R^D)_2$, —SO$_2$R$^D$, —SO$_2$N$(R^D)_2$, —N(R$^d$)SO$_2$R$^D$, N(R$^d$)SO$_2$NR$^D$, N(R$^d$)SO$_2$NHC(O)OR$^D$, N(R$^d$)SO$_2$NHC(O)R$^D$, a C$_{1-6}$ aliphatic, —(C$_{1-6}$ aliphatic)-R$^D$, a C$_{3-8}$ cycloaliphatic ring, a 6 to 10-membered aryl ring, a 4 to 8-membered heterocyclic ring and a 5 to 10-membered heteroaryl ring; wherein each said 4 to 8-membered heterocyclic ring and each said 5 to 10-membered heteroaryl ring contains between 1 and 3 heteroatoms independently selected from O, N and S; and wherein each said C$_{1-6}$ aliphatic, each said C$_{1-6}$ aliphatic portion of the —(C$_{1-6}$ aliphatic)-R$^D$ moiety, each said C$_{3-8}$ cycloaliphatic ring, each said 6 to 10-membered aryl ring, each said 4 to 8-membered heterocyclic ring and each said 5 to 10-membered heteroaryl ring is optionally and independently substituted with up to 5 instances of R$^{5d}$;

J$^4$ is selected from the group consisting of a lone pair on nitrogen, hydrogen, halogen, oxo, methyl, hydroxyl, methoxy, trifluoromethyl, trifluoromethoxy and —NR$^a$R$^b$; wherein R$^a$ and R$^b$ are each independently hydrogen, C$_{1-6}$ alkyl or a 3-6 cycloalkyl ring; or wherein R$^a$ and R$^b$, together with the nitrogen atom to which they are both attached, form a 4-8 membered heterocyclic ring, or a 5-membered heteroaryl ring optionally containing up to two additional heteroatoms selected from N, O and S; wherein each of said 4-8 membered heterocyclic ring and 5-membered heteroaryl ring is optionally and independently substituted by up to 6 instances of fluorine;

each R$^D$ is independently selected from the group consisting of hydrogen, a C$_{1-6}$ aliphatic, —(C$_{1-6}$ aliphatic)-R$^f$, a C$_{3-8}$ cycloaliphatic ring, a 4 to 10-membered heterocyclic ring, phenyl and a 5 to 6-membered heteroaryl ring; wherein each said 4 to 10-membered heterocyclic ring and each said 5 to 6-membered heteroaryl ring contains between 1 and 3 heteroatoms independently selected from O, N and S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 10-membered heterocyclic ring, each said phenyl and each said 5 to 6-membered heteroaryl ring is optionally and independently substituted with up to 5 instances of R$^{5a}$; wherein when any R$^D$ is one of a C$_{1-6}$ aliphatic or a —(C$_{1-6}$ aliphatic)-R$^f$ group, one or two —CH$_2$-units that form said C$_{1-6}$ aliphatic chains may, optionally, be replaced by a group independently —N(R$^d$)—, —CO— or —O—;

each R$^d$ is independently selected from the group consisting of hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl and a 5 to 6-membered heteroaryl ring; wherein each said 4 to 8-membered heterocyclic ring and each said 5 or 6-membered heteroaryl ring contains between 1 and 3 heteroatoms independently selected from O, N and S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 8-membered heterocyclic ring, each said phenyl and each said 5 to 6-membered heteroaryl ring is optionally and independently substituted by up to 5 instances of R$^{5b}$; wherein when any R$^d$ is one of a C$_{1-6}$ aliphatic or a —(C$_{1-6}$ aliphatic)-R$^f$ group, one or two —CH$_2$— units that form said C$_{1-6}$ aliphatic chains may, optionally, be replaced by a group independently selected from —N(R$^{dd}$)—, —CO— or —O—;

each R$^{dd}$ is independently selected from the group consisting of hydrogen, a C$_{1-6}$ aliphatic, —(C$_{1-6}$ aliphatic)-R$^f$, a C$_{3-8}$ cycloaliphatic ring, a 4 to 8-membered heterocyclic ring, phenyl and a 5 to 6-membered heteroaryl ring; wherein each said 4 to 8-membered heterocyclic ring and each said 5 or 6-membered heteroaryl ring contains between 1 and 3 heteroatoms independently selected from O, N and S; and wherein each said C$_{1-6}$ aliphatic, each said C$_{1-6}$ aliphatic portion of the —(C$_{1-6}$ aliphatic)-R$^f$ moiety, each said C$_{3-8}$ cycloaliphatic ring, each said 4 to 8-membered heterocyclic ring, each said phenyl and each said 5 to 6-membered heteroaryl ring is optionally and independently substituted by up to 5 instances of R$^{5b}$;

each R$^f$ is independently selected from the group consisting of a C$_{1-3}$ alkyl, a C$_{3-8}$ cycloaliphatic ring, a 4 to 10-membered heterocyclic ring, phenyl or a 5 to 6-membered heteroaryl ring; wherein each said 4 to 10-membered heterocyclic ring and each said 5 to 6-membered heteroaryl ring contains between 1 and 4 heteroatoms independently selected from O, N and S; and wherein each said C$_{3-8}$ cycloaliphatic ring, each said 4 to 10-membered heterocyclic ring, each said phenyl and each said 5 to 6-membered heteroaryl ring is optionally and independently substituted by up to 5 instances of R$^5$;

when J$^D$ is —C(O)N$(R^D)_2$, —N$(R^D)_2$, —N(R$^d$)C(O)N$(R^D)_2$, —OC(O)N$(R^D)_2$ or —SO$_2$N$(R^D)_2$, the two R$^D$ groups together with the nitrogen atom attached to the two R$^D$ groups may form a 4 to 8-membered heterocyclic ring or a 5-membered heteroaryl ring; wherein each said 4 to 8-membered heterocyclic ring and each said 5-membered heteroaryl ring optionally contains up to 3 additional heteroatoms independently selected from N, O and S, in addition to the nitrogen atom to which the two R$^D$ groups are attached; and wherein each said 4 to 8-membered heterocyclic ring and each said 5-membered heteroaryl ring is optionally and independently substituted by up to 5 instances of R$^5$;

when J$^D$ is —N(R$^d$)C(O)R$^D$, the R$^D$ group together with the carbon atom attached to the R$^D$ group, with the nitrogen atom attached to the R$^d$ group, and with the R$^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O and S, in addition to the nitrogen atom to which the R$^d$ group is attached; and wherein each said 4 to 8-membered heterocyclic ring and each said 5-membered heteroaryl ring is optionally and independently substituted by up to 5 instances of R$^5$;

when J$^D$ is —N(R$^d$)C(O)OR$^D$, the R$^D$ group together with the oxygen atom attached to the R$^D$ group, with the carbon atom of the —C(O)— portion of the —N(R$^d$)C(O)OR$^D$ group, with the nitrogen atom attached to the R$^d$ group, and with said R$^d$ group, may form a 4 to 8-membered heterocyclic ring; wherein said 4 to 8-membered heterocyclic ring optionally contains up to 2 additional heteroatoms independently selected from N, O or S, and is optionally and independently substituted by up to 5 instances of R$^5$;

when J$^D$ is —N(R$^d$)C(O)N$(R^D)_2$, one of the R$^D$ groups attached to the nitrogen atom, together with said nitrogen atom, and with the N atom attached to the R$^d$ group and said R$^d$ group may form a 4 to 8-membered heterocyclic ring; wherein said 4 to 8-membered heterocyclic ring optionally contains up to 2 additional heteroatoms independently selected from N, O and S, and is optionally and independently substituted by up to 5 instances of $R^5$;

when $J^D$ is $N(R^d)SO_2R^D$, the $R^D$ group together with the sulfur atom attached to the $R^D$ group, with the nitrogen atom attached to the $R^d$ group, and with said $R^d$ group may combine to form a 4 to 8-membered heterocyclic ring; wherein said 4 to 8-membered heterocyclic ring optionally contains up to 2 additional heteroatoms independently selected from N, O and S, and is optionally and independently substituted by up to 5 instances of $R^5$;

each $R^5$ is independently selected from the group consisting of halogen, —CN, $C_{1-6}$ alkyl, —($C_{1-6}$ alkyl)-$R^6$, —$OR^6$, —$SR^6$, —$COR^6$, —$OC(O)R^6$, —$C(O)OR^6$, —$C(O)N(R^6)_2$, —$C(O)N(R^6)SO_2R^6$, —$N(R^6)C(O)R^6$, —$N(R^6)C(O)OR^6$, —$N(R^6)C(O)N(R^6)_2$, —$N(R^6)_2$, —$SO_2R^6$, —$SO_2OH$, —$SO_2NHOH$, —$SO_2N(R^6)_2$, —$SO_2N(R^6)COOR^6$, —$SO_2N(R^6)C(O)R^6$, —$N(R^6)SO_2R^6$, —$(C=O)NHOR^6$, a $C_{3-8}$ cycloalkyl ring, a 4 to 7-membered heterocyclic ring, a 5 or 6-membered heteroaryl ring, phenyl, benzyl, an oxo group and a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of the —($C_{1-6}$ alkyl)-$R^6$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —$NH_2$, —$NH(C_{1-4}$ alkyl), —$N(C_{1-4}$ alkyl)$_2$, —CN, —COOH, —$CONH_2$, —$COO(C_{1-4}$ alkyl), —$O(C_{1-4}$ alkyl), —$O(C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O and S; and wherein said bicyclic group is optionally and independently substituted by up to six instances of halogen, $C_{1-4}$ alkyl, —OH, —$NH_2$, —$NH(C_{1-4}$ alkyl), —$N(C_{1-4}$ alkyl)$_2$, —CN, —COOH, —$CONH_2$, —$COO(C_{1-4}$ alkyl), —$O(C_{1-4}$ alkyl), —$O(C_{1-4}$ haloalkyl) or oxo;

two instances of $R^5$, attached to the same or different atoms of $J^D$, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to four ring heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —$C(O)O(C_{1-4}$ alkyl), —$C(O)OH$, —$NR(CO)O(C_{1-4}$ alkyl), —$CONH_2$, —OH or halogen; wherein R is hydrogen or a $C_{1-2}$ alkyl;

each $R^{5a}$ is independently selected from the group consisting of halogen, —CN, $C_{1-6}$ alkyl, —($C_{1-6}$ alkyl)$R^{6a}$, —$OR^{6a}$, —$SR^{6a}$, —$COR^{6a}$, —$OC(O)R^{6a}$, —$C(O)OR^{6a}$, —$C(O)N(R^{6a})_2$, —$C(O)N(R^{6a})SO_2R^{6a}$—$N(R^{6a})C(O)R^{6a}$—$N(R^{6a})C(O)OR^{6a}$, —$N(R^{6a})C(O)N(R^{6a})_2$, —$N(R^{6a})_2$, —$SO_2R^{6a}$, —$SO_2OH$, —$SO_2NHOH$, —$SO_2N(R^{6a})_2$, —$SO_2N(R^{6a})COOR^{6a}$, —$SO_2N(R^{6a})C(O)R^{6a}$, —$N(R^{6a})SO_2R^{6a}$, —$(C=O)NHOR^{6a}$, a $C_{3-8}$ cycloalkyl ring, a 4 to 7-membered heterocyclic ring, a 5 or 6-membered heteroaryl ring, phenyl, benzyl, an oxo group and a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-4}$ alkyl portion of the —($C_{1-6}$ alkyl)$R^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —$NH_2$, —$NH(C_{1-4}$ alkyl), —$N(C_{1-4}$ alkyl)$_2$, —CN, —COOH, —$CONH_2$, —$COO(C_{1-4}$ alkyl), —$O(C_{1-4}$ alkyl), —$O(C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O and S; and wherein said bicyclic group is optionally and independently substituted by up to six instances of halogen, $C_{1-4}$ alkyl, —OH, —$NH_2$, —$NH(C_{1-4}$ alkyl), —$N(C_{1-4}$ alkyl)$_2$, —CN, —COOH, —$CONH_2$, —$COO(C_{1-4}$ alkyl), —$O(C_{1-4}$ alkyl), —$O(C_{1-4}$ haloalkyl) or oxo;

each $R^{5b}$ is independently selected from the group consisting of halogen, —CN, $C_{1-6}$ alkyl, —($C_{1-6}$ alkyl)$R^{6a}$, —$OR^{6a}$, —$SR^{6a}$, —$COR^{6a}$, —$OC(O)R^{6a}$, —$C(O)OR^{6a}$, —$C(O)N(R^{6a})_2$, —$C(O)N(R^{6a})SO_2R^{6a}$—$N(R^{6a})C(O)R^{6a}$—$N(R^{6a})C(O)OR^{6a}$, —$N(R^{6a})C(O)N(R^{6a})_2$, —$N(R^{6a})_2$, —$SO_2R^{6a}$, —$SO_2OH$, —$SO_2NHOH$, —$SO_2N(R^{6a})_2$, —$SO_2N(R^{6a})COOR^{6a}$, —$SO_2N(R^{6a})C(O)R^{6a}$, —$N(R^{6a})SO_2R^{6a}$, —$(C=O)NHOR^{6a}$, a $C_{3-8}$ cycloalkyl ring, a 4 to 7-membered heterocyclic ring, a 5 or 6-membered heteroaryl ring, phenyl, benzyl, an oxo group and a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{1-6}$ alkyl portion of the —($C_{1-6}$ alkyl)$R^{6a}$ moiety, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, $C_{1-4}$ haloalkyl, —OH, —$NH_2$, —$NH(C_{1-4}$ alkyl), —$N(C_{1-4}$ alkyl)$_2$, —CN, —COOH, —$CONH_2$, —$COO(C_{1-4}$ alkyl), —$O(C_{1-4}$ alkyl), —$O(C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O and S; and wherein said bicyclic group is optionally and independently substituted by up to six instances of halogen, $C_{1-4}$ alkyl, —OH, —$NH_2$, —$NH(C_{1-4}$ alkyl), —$N(C_{1-4}$ alkyl)$_2$, —CN, —COOH, —$CONH_2$, —$COO(C_{1-4}$ alkyl), —$O(C_{1-4}$ alkyl), —$O(C_{1-4}$ haloalkyl) or oxo;

two instances of $R^{5a}$ or two instances of $R^{5b}$ attached to the same or different atoms of $R^D$ or $R^d$, respectively, together with said atom or atoms to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —C(O)NH$_2$, —NR(CO)O ($C_{1-4}$ alkyl), —OH or halogen; wherein R is hydrogen or a $C_{1-2}$ alkyl;

each $R^{5c}$ is independently selected from the group consisting of halogen, —CN, $C_{1-6}$ alkyl, —($C_{1-6}$ alkyl)-$R^{6b}$, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, —N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$OH, —SO$_2$NHOH, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6b}$)SO$_2$R$^{6b}$, —(C=O)NHOR$^{6b}$, a $C_{3-8}$ cycloalkyl ring, a 4 to 7-membered heterocyclic ring, a 5 or 6-membered heteroaryl ring, phenyl, benzyl, an oxo group, and a bicyclic group; wherein each of said 5 or 6-membered heteroaryl ring and each of said 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-$R^{6b}$ moiety, each of said $C_{3-8}$ cycloalkyl ring, each of said 4 to 7-membered heterocyclic ring, each of said 5 or 6-membered heteroaryl ring, each of said benzyl and each of said phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo; wherein said bicyclic group contains a first ring and a second ring in a fused or bridged relationship, said first ring is a 4 to 7-membered heterocyclic ring, a 5 or 6-membered heteroaryl ring, phenyl or benzyl, and said second ring is a phenyl ring or a 5 or 6-membered heteroaryl ring containing up to 3 ring heteroatoms selected from N, O and S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5c}$ attached to the same or different atoms of R, together with said atom or atoms to which it is attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —CONH$_2$, —NR(CO)O($C_{1-4}$ alkyl), —OH or halogen; wherein R is hydrogen or a $C_{1-2}$ alkyl;

each $R^{5d}$ is independently selected from the group consisting of halogen, —CN, $C_{1-6}$ alkyl, —($C_{1-6}$ alkyl)-$R^6$, —OR$^6$, —SR$^6$, —COR$^6$, —OC(O)R$^6$, —C(O)OR$^6$, —C(O)N(R$^6$)$_2$, —N(R$^6$)C(O)R$^6$, —N(R$^6$)C(O)OR$^6$, —N(R$^6$)C(O)N(R$^6$)$_2$, —N(R$^6$)$_2$, —SO$_2$R$^6$, —SO$_2$OH, —SO$_2$NHOH, —SO$_2$N(R$^6$)COR$^6$, —SO$_2$N(R$^6$)$_2$, —N(R$^6$)SO$_2$R$^6$, a $C_{7-12}$ aralkyl, a $C_{3-8}$ cycloalkyl ring, a 4 to 7-membered heterocyclic ring, a 5 or 6-membered heteroaryl ring, phenyl and an oxo group; wherein each 5 or 6-membered heteroaryl ring or 4 to 7-membered heterocyclic ring contains up to four ring heteroatoms independently selected from N, O and S, wherein each of said $C_{1-6}$ alkyl, $C_{1-6}$ alkyl portion of the —($C_{1-6}$ alkyl)-$R^6$ moiety, $C_{7-12}$ aralkyl, $C_{3-8}$ cycloalkyl ring, 4 to 7-membered heterocyclic ring, 5 or 6-membered heteroaryl ring or phenyl group is optionally and independently substituted with up to 3 instances of halogen, $C_{1-4}$ alkyl, $C_{1-4}$(haloalkyl), —OH, —NH$_2$, —NH($C_{1-4}$ alkyl), —N($C_{1-4}$ alkyl)$_2$, —CN, —COOH, —CONH$_2$, —COO($C_{1-4}$ alkyl), —O($C_{1-4}$ alkyl), —O($C_{1-4}$ haloalkyl) or oxo;

two instances of $R^{5d}$ attached to the same or different atoms of $J^D$, together with said atom or atoms of $J^D$ to which they are attached, may optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship with respect to each other; wherein said 4 to 6-membered heterocycle or said 5 or 6-membered heteroaryl ring contains up to four ring heteroatoms independently selected from N, O and S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)O($C_{1-4}$ alkyl), —C(O)NH$_2$, —OH or halogen; wherein R is hydrogen or a $C_{1-2}$ alkyl;

each $R^6$ is independently selected from the group consisting of hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6a}$ is independently selected from the group consisting of hydrogen, a $C_{1-6}$ alkyl, phenyl, benzyl, a $C_{3-8}$ cycloalkyl ring, a 4 to 7-membered heterocyclic ring and a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —C(O)N($C_{1-6}$ alkyl)$_2$, —C(O)NH($C_{1-6}$ alkyl), —C(O)N($C_{1-6}$ haloalkyl)$_2$, —C(O)NH($C_{1-6}$ haloalkyl), C(O)N($C_{1-6}$ alkyl)($C_{1-6}$ haloalkyl), —COO($C_{1-6}$ alkyl), —COO($C_{1-6}$ haloalkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

each $R^{6b}$ is independently hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —C(O)NH$_2$, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S;

two instances of $R^6$ linked to the same nitrogen atom of $R^5$ or $R^{5d}$, together with said nitrogen atom of $R^5$ or $R^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O and S;

two instances of $R^{6a}$ linked to a nitrogen atom of $R^{5a}$ or $R^{5b}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O and S;

two instances of $R^{6b}$ linked to a nitrogen atom of $R^{5c}$, together with said nitrogen, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O and S;

Y is either absent or is a $C_{1-6}$ alkyl chain, optionally substituted by up to 6 instances of fluoro; and wherein in said Y that is a $C_{1-6}$ alkyl chain, up to 3 methylene units of this alkyl chain, can be replaced by a group selected from —O—, —C(O)— and —N(($Y^1$)—$R^{90}$)—, wherein $Y^1$ is either absent or is a $C_{1-6}$ alkyl chain, optionally substituted by up to 6 instances of fluoro; and:

when $Y^1$ is absent, each $R^{90}$ is independently selected from the group consisting of hydrogen, —COR$^{10}$, —C(O)OR$^{10}$, —C(O)N(R$^{10}$)$_2$, —C(O)N(R$^{10}$)SO$_2$R$^{10}$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —(C=O)NHOR$^{10}$ a $C_{3-6}$ cycloalkyl ring, a 4-8-membered heterocyclic ring, a phenyl ring and a 5-6 membered heteroaryl ring; wherein each said 4 to 8-membered heterocyclic ring or 5 to 6-membered heteroaryl ring contains up to 4 ring heteroatoms independently selected from N, O and S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$; and when $Y^1$ is present, each $R^{90}$ is independently selected from the group consisting of hydrogen, halogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring and a 5-6 membered heteroaryl ring; wherein each said 4 to 8-membered heterocyclic ring or 5 to 6-membered heteroaryl ring contains up to 4 ring heteroatoms independently selected from N, O and S; and wherein each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^9$ is independently selected from the group consisting of hydrogen, halogen, a $C_{1-6}$ alkyl, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, —(C=O)NHOR$^{10}$, $C_{3-6}$ cycloalkyl ring, a 4-8-membered heterocyclic ring, a phenyl ring and a 5-6 membered heteroaryl ring; wherein each said 4 to 8-membered heterocyclic ring or 5 to 6-membered heteroaryl ring contains up to 4 ring heteroatoms independently selected from N, O and S; and wherein each of said $C_{1-6}$ alkyl, each of said $C_{3-6}$ cycloalkyl rings, each of said 4 to 8-membered heterocyclic rings, each of said phenyl and each of said 5 to 6-membered heteroaryl rings is optionally and independently substituted with up to 3 instances of $R^{11}$;

each $R^{10}$ is independently selected from the group consisting of hydrogen, a $C_{1-6}$ alkyl, —($C_{1-6}$ alkyl)-R$^{13}$, phenyl, benzyl, a $C_{3-8}$ cycloalkyl ring, a 4 to 7-membered heterocyclic ring and a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, $C_{1-6}$ alkyl portion of said —($C_{1-6}$ alkyl)-R$^{13}$ moiety, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of $R^{11a}$;

each $R^{13}$ is independently a phenyl, a benzyl, a $C_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each said phenyl, each of said benzyl, each said $C_{3-8}$ cycloalkyl group, each said 4 to 7-membered heterocyclic ring and each 5 or 6-membered heteroaryl ring is optionally and independently substituted with up to 3 instances of $R^{11b}$;

each $R^{11}$ is independently selected from the group consisting of halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ and —N(R$^{12}$)SO$_2$R$^{12}$; wherein each of said $C_{1-6}$ alkyl is optionally and independently substituted by up to 6 instances of fluoro and/or 3 instances of $R^{121}$;

each $R^{11a}$ is independently selected from the group consisting of halogen, oxo, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ and —N(R$^{12}$)SO$_2$R$^{12}$; wherein each of said $C_{1-6}$ alkyl is optionally and independently substituted by up to 6 instances of fluoro and/or 3 instances of $R^{121}$; and each $R^{11b}$ is independently selected from the group consisting of halogen, $C_{1-6}$ alkyl, oxo, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ and —N(R$^{12}$)SO$_2$R$^{12}$; wherein each of said $C_{1-6}$ alkyl is optionally and independently substituted by up to 6 instances of fluoro and/or 3 instances of $R^{121}$.

each $R^{12}$ is selected from the group consisting of hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring and 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$(fluoroalkyl), —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ fluoroalkyl) or oxo;

each $R^{121}$ is selected from the group consisting of hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each 5 or 6-membered heteroaryl ring and 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of halogen, $C_{1-4}$ alkyl, $C_{1-4}$(fluoroalkyl), —OH, —NH$_2$, —NH(C$_{1-4}$ alkyl), —N(C$_{1-4}$ alkyl)$_2$, —CN, —COOH, —CONH$_2$, —COO(C$_{1-4}$ alkyl), —O(C$_{1-4}$ alkyl), —O(C$_{1-4}$ fluoroalkyl) or oxo; and each $J^C$ is independently hydrogen or a $C_{1-6}$ alkyl.

In some embodiments of the above methods, uses and compositions, the sGC stimulator is a compound of Formula XY, or a pharmaceutically acceptable salt thereof:

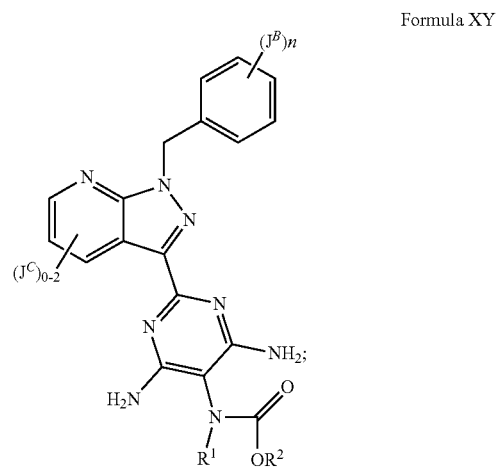

Formula XY n is 0 or an integer selected from 1 to 3;

each $J^B$ is independently halogen, —CN, a $C_{1-6}$ aliphatic, —OR$^B$ or a $C_{3-8}$ cycloaliphatic ring; wherein each of said $C_{1-6}$ aliphatic and each of said $C_{3-8}$ cycloaliphatic group is optionally substituted with up to 3 instances of halogen;

each $R^B$ is independently hydrogen, a $C_{1-6}$ aliphatic or a $C_{3-8}$ cycloaliphatic ring; wherein each of said $R^B$ that is a $C_{1-6}$ aliphatic and each of said $R^B$ that is a $C_{3-8}$ cycloaliphatic ring is optionally substituted with up to 3 instances of halogen; each $J^C$, if present, is independently halogen;

$R^1$ is hydrogen or $C_{1-6}$ alkyl; and $R^2$ is a $C_{1-6}$ alkyl.

In some embodiments of Formula XY, n is 1 or 2. In some embodiments, n is 1.

In some embodiments of Formula XY, each $J^B$ is a halogen. In some of these embodiments, each $J^B$ is fluoro. In some embodiments of Formula XY, n is 1 and $J^B$ is fluoro.

In some embodiments of Formula XY, one or two instances of $J^C$ are present. In other embodiments, only one instance of $J^C$ is present. In some of these embodiments, $J^C$ is fluoro.

In some embodiments of Formula XY, $R^1$ is hydrogen, methyl or ethyl. In other embodiments, $R^1$ is hydrogen. In still other embodiments, $R^1$ is methyl.

In some embodiments of Formula XY, $R^2$ is methyl or ethyl. In still other embodiments, $R^2$ is methyl.

In some embodiments of Formula XY, the compound is
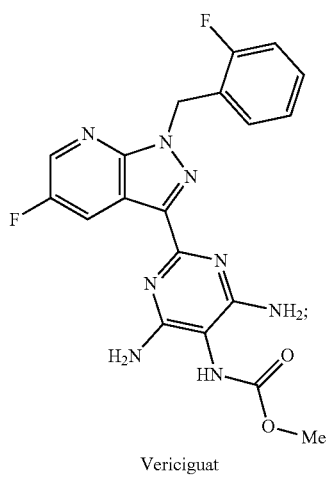
Vericiguat
or
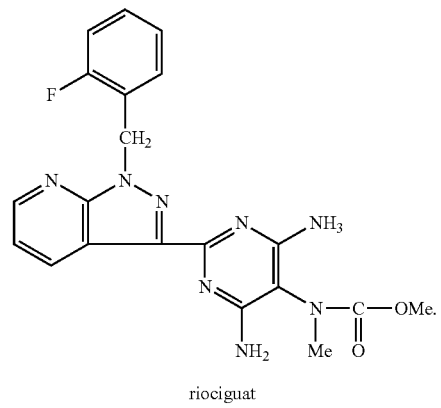
riociguat
In some embodiments, the sGC stimulator is selected from:
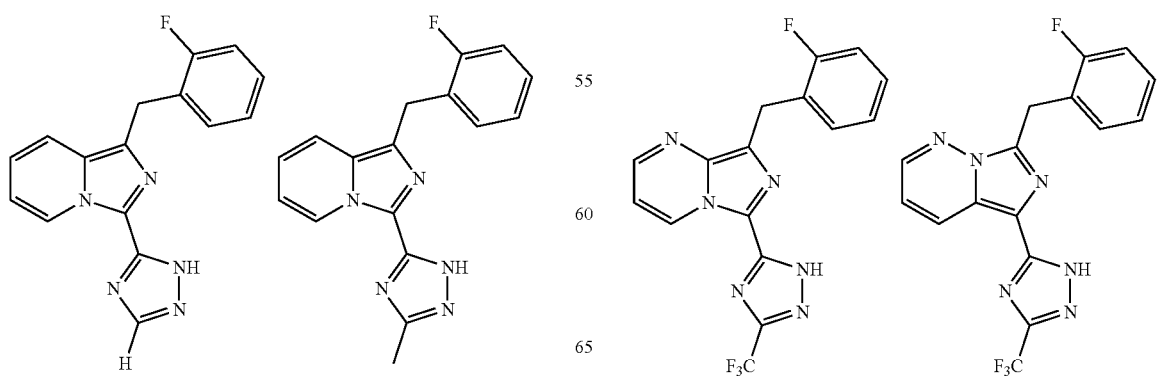
-continued
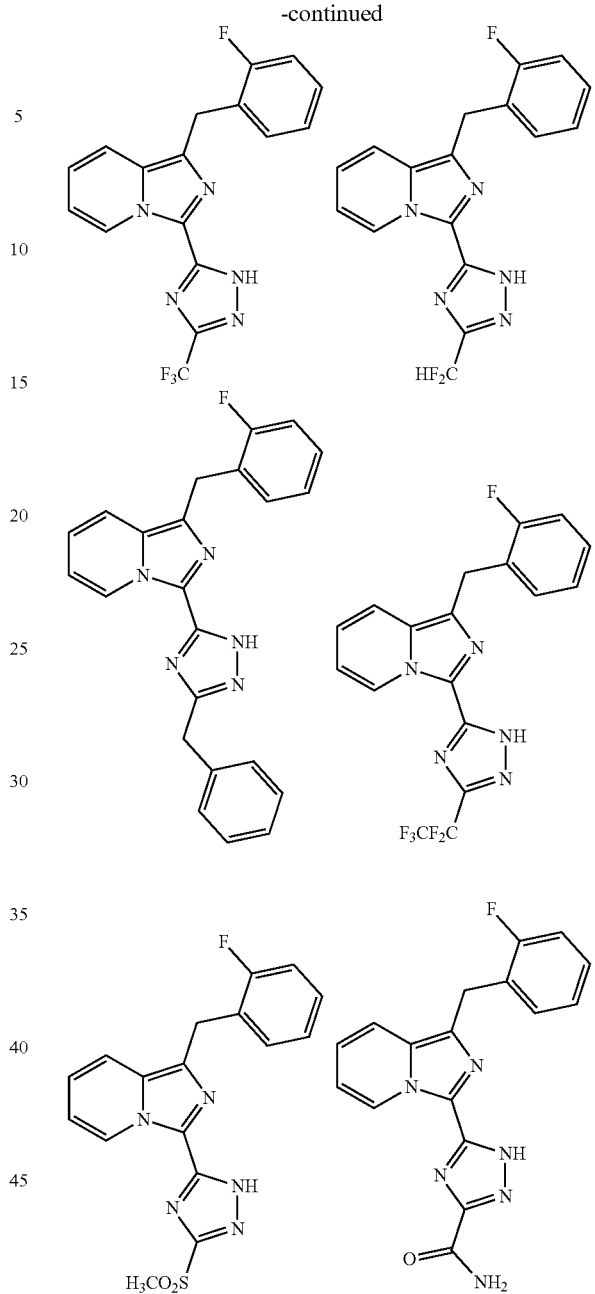

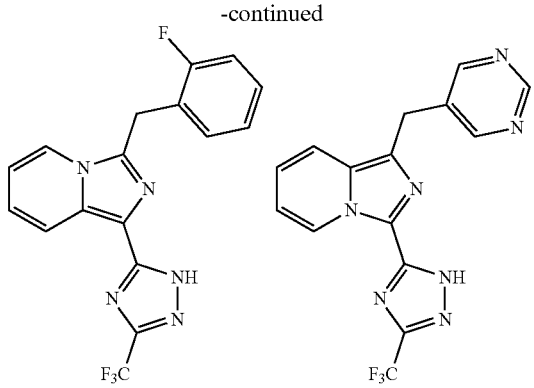
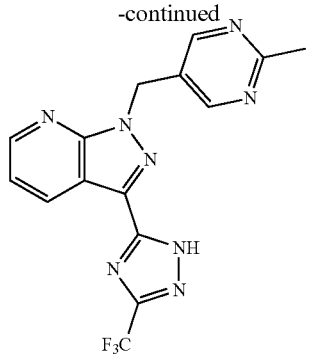
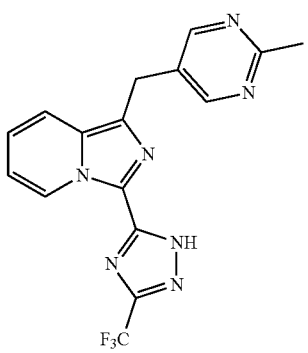
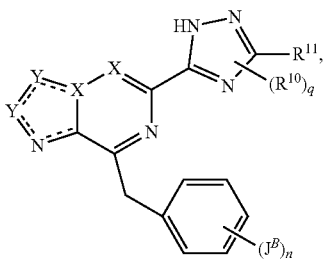
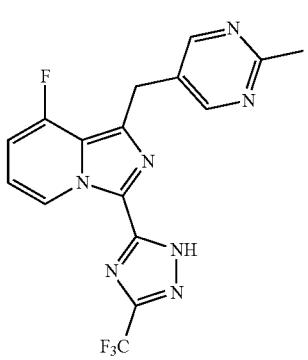
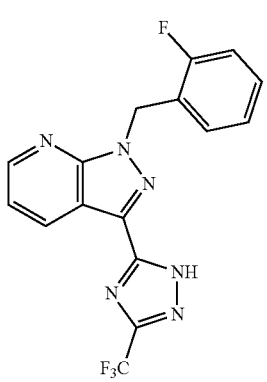

and

In some embodiments, the sGC stimulator is one of Formula A, or a pharmaceutically acceptable salt thereof:

Formula A wherein:

Each Y is independently selected from N, NJ$^c$, CH, or CJ$^c$;

Each X is either N, NJ$^c$, CH, or CJ$^c$;

wherein a maximum of 3 instances of X and Y are simultaneously N or NJ$^c$;

J$^F$ is halo, CN, or C$_{1-3}$alkyl optionally substituted with 1 to 3 halo;

Each J$^B$ is independently selected from halo or C$_{1-4}$alkyl;

n is 0, 1, 2, or 3;

R$^{10}$ is C$_{1-4}$alkyl optionally substituted with 1, 2, or 3 groups independently selected from halo, —C(O)R$^{b2}$, phenyl, and 5- or 6-membered heteroaryl, wherein the phenyl and 5- or 6-membered heteroaryl are optionally substituted with 1, 2, or 3 halo or C$_{1-4}$alkyl, wherein the heteroaryl includes 1, 2, or 3 heteroatoms independently selected from N, O, and S;

q is 0 or 1;

R$^{11}$ is H, halo, —NR$^{a2}$R$^{b2}$, C$_{1-4}$alkyl, 5- to 6-membered heteroaryl, or C$_{3-6}$ cycloalkyl, wherein the C$_{1-4}$alkyl, 5- to 6-membered heteroaryl, and C$_{3-6}$ cycloalkyl are each optionally substituted with 1, 2, or 3 groups independently selected from halo, wherein the heteroaryl includes 1, 2, or 3 heteroatoms independently selected from N, O, and S;

R$^{a2}$ is hydrogen or C$_{1-4}$ alkyl; and R$^{b2}$ is hydrogen or C$_{1-4}$ alkyl.

In some embodiments, the sGC stimulator is one of Formula B, or a pharmaceutically acceptable salt thereof:

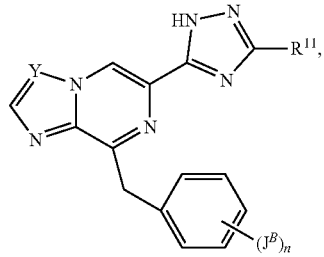

Formula B

Wherein:
Y is N or CH;
Each $J^B$ is independently selected from halo or $C_{1-4}$alkyl;
n is 0, 1, 2, or 3;
$R^{11}$ is H, halo, —$NR^{a2}R^{b2}$, $C_{1-4}$alkyl, 5- to 6-membered heteroaryl, or $C_{3-6}$ cycloalkyl, wherein the $C_{1-4}$alkyl, 5- to 6-membered heteroaryl, and $C_{3-6}$ cycloalkyl are each optionally substituted with 1, 2, or 3 groups independently selected from halo;
$R^{a2}$ is hydrogen or $C_{1-4}$ alkyl; and
$R^{b2}$ is hydrogen or $C_{1-4}$ alkyl.

In some embodiments, the sGC stimulator is one of Formula C, or a pharmaceutically acceptable salt thereof:

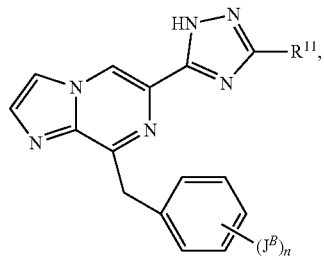

Formula C

Wherein:
Y is N or CH;
Each $J^B$ is independently selected from halo or $C_{1-4}$alkyl;
n is 0, 1, 2, or 3;
$R^{11}$ is H, halo, —$NR^{a2}R^{b2}$, $C_{1-4}$alkyl, 5- to 6-membered heteroaryl, or $C_{3-6}$ cycloalkyl, wherein the $C_{1-4}$alkyl, 5- to 6-membered heteroaryl, and $C_30.6$ cycloalkyl are each optionally substituted with 1, 2, or 3 groups independently selected from halo;
$R^{a2}$ is hydrogen or $C_{1-4}$ alkyl; and
$R^{b2}$ is hydrogen or $C_{1-4}$ alkyl.

In some embodiments of Formulas A, B and C, $R^{11}$ is $C_{1-4}$alkyl optionally substituted with 1, 2, or 3 halo.

In some embodiments, the sGC stimulator is of Formula A, B or C, and is one of the following:

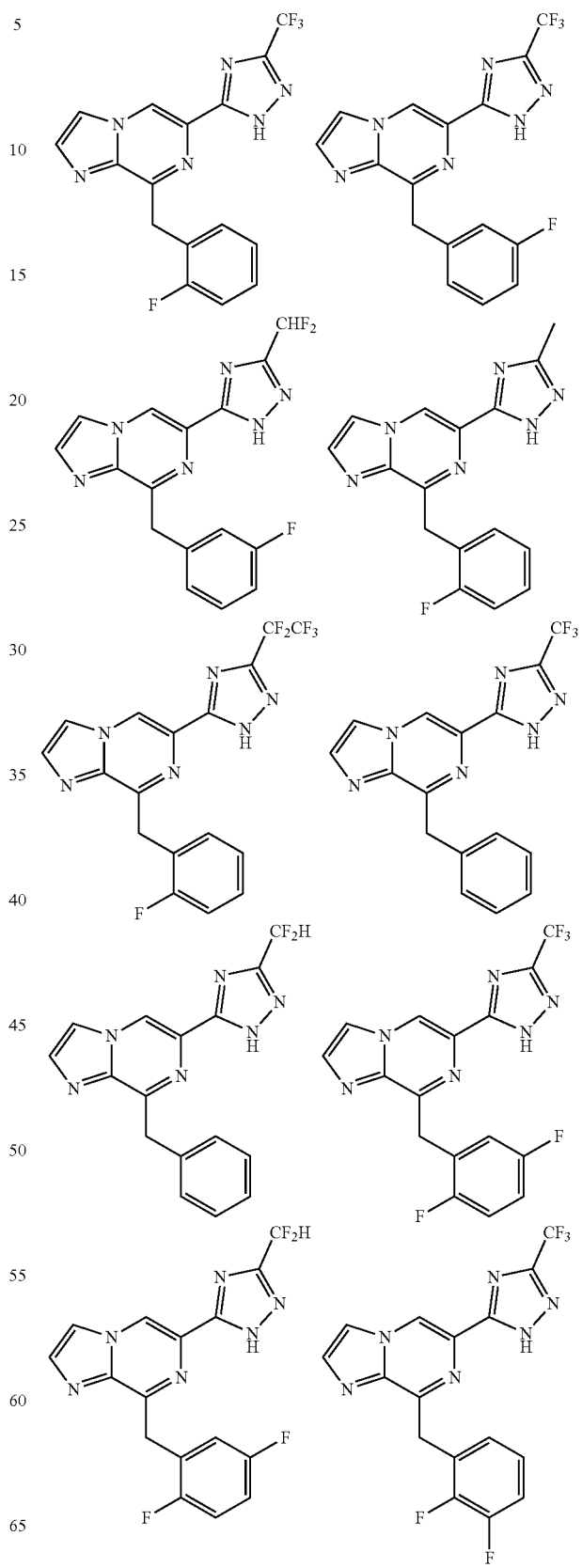

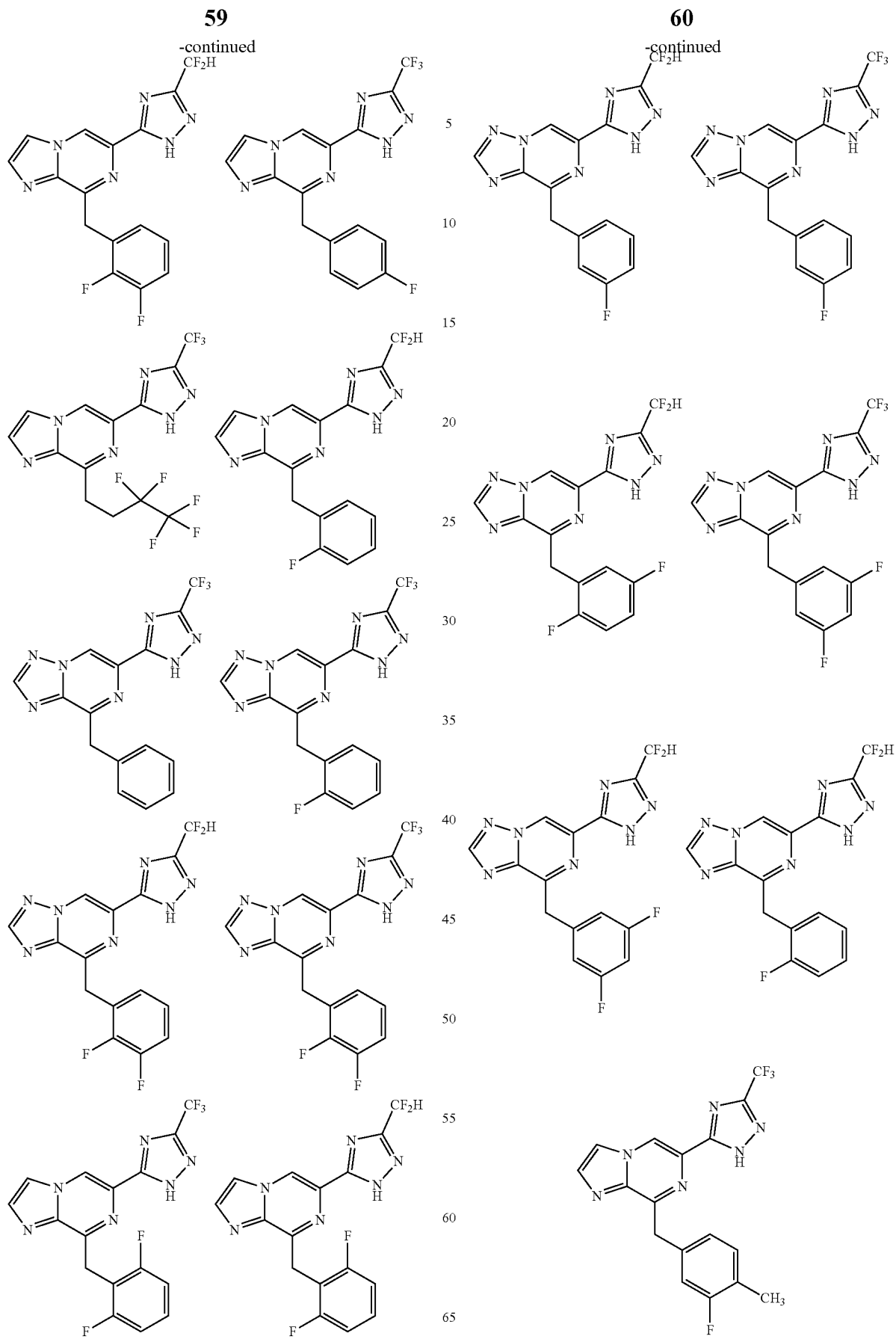

61
-continued
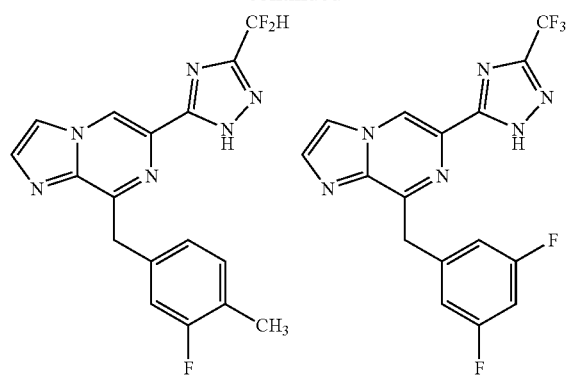
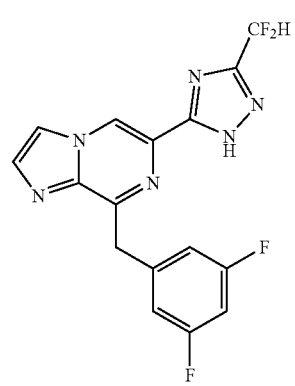
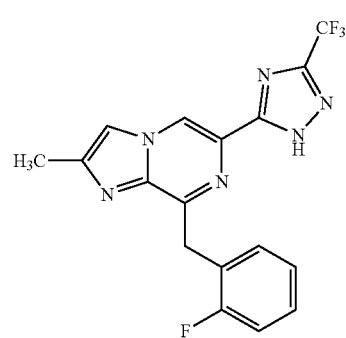
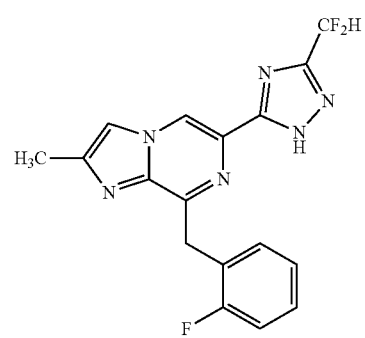
62
-continued
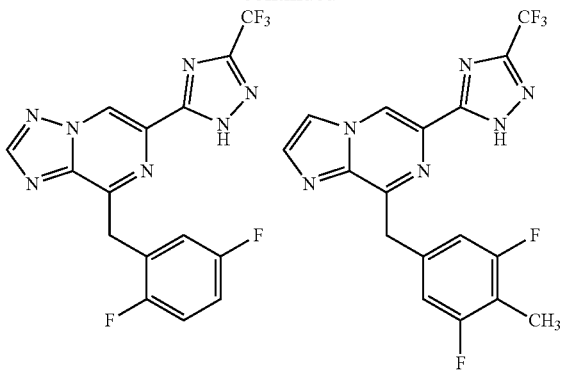
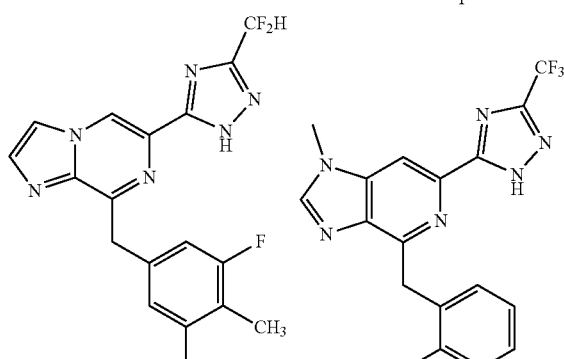
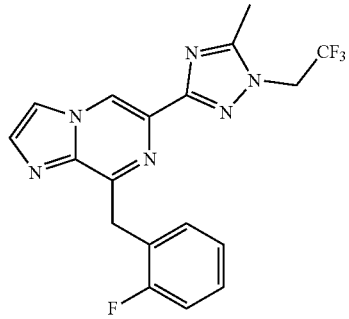
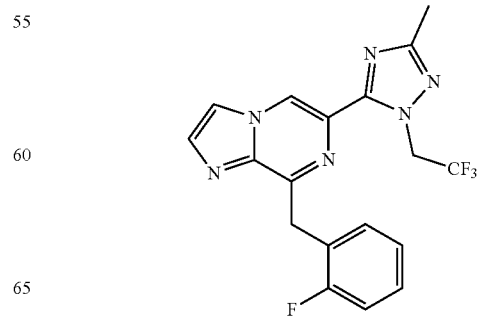

-continued
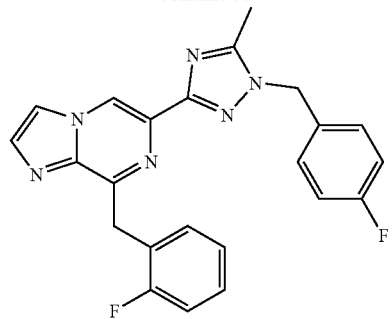
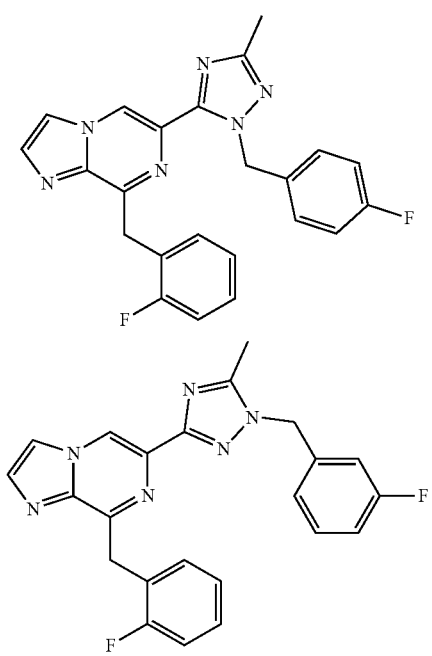
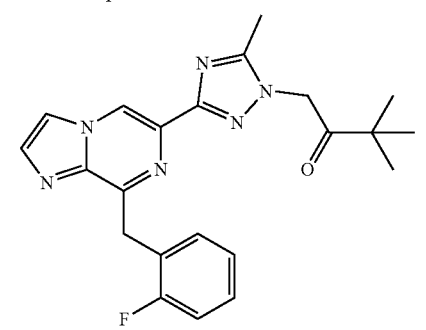
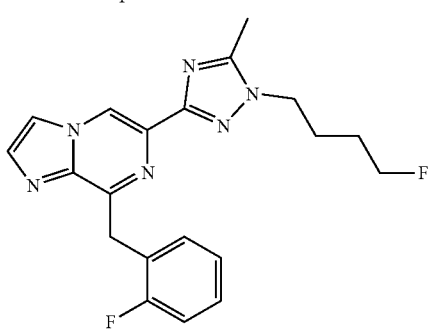
-continued
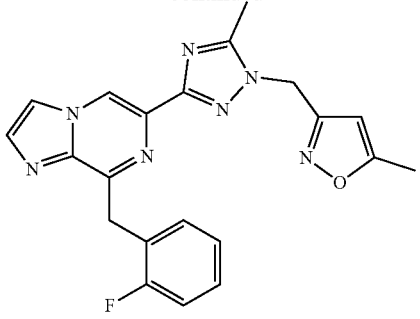
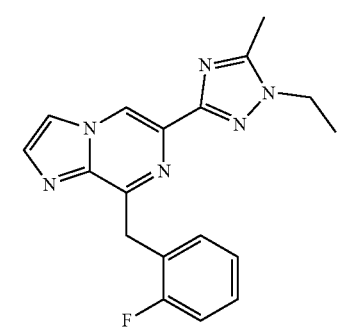
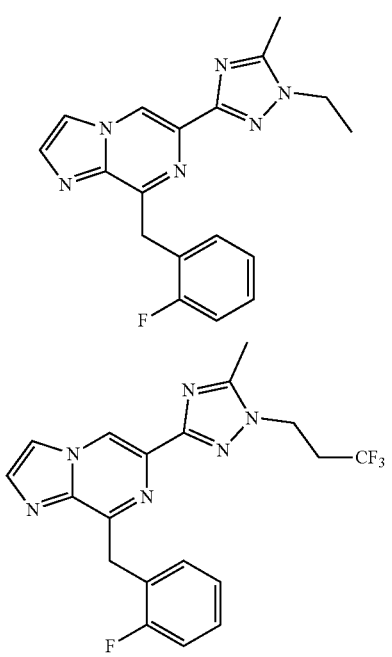
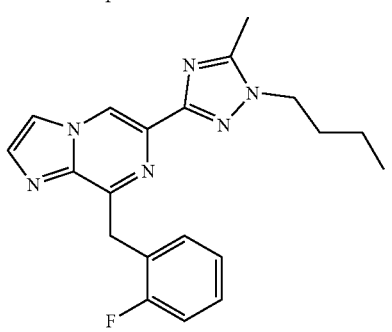
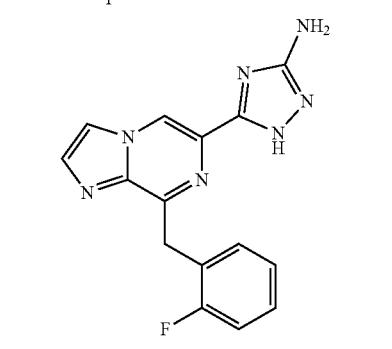

65
-continued
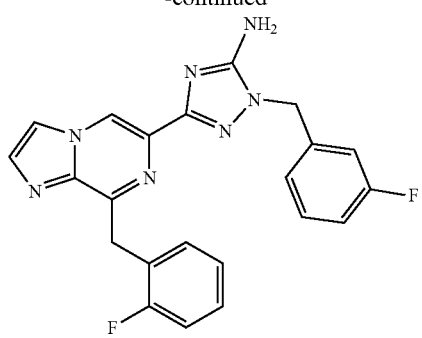
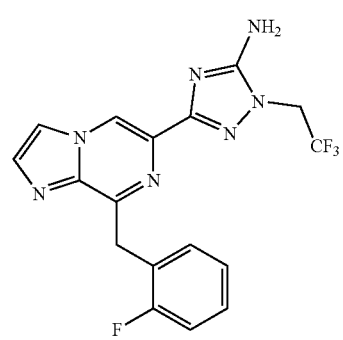
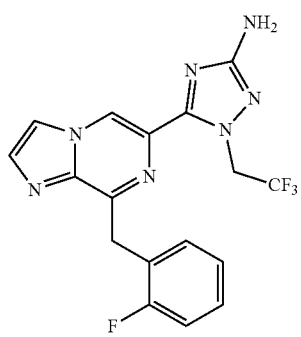
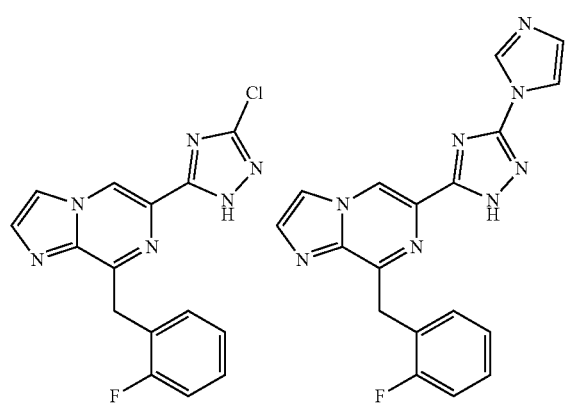
66
-continued
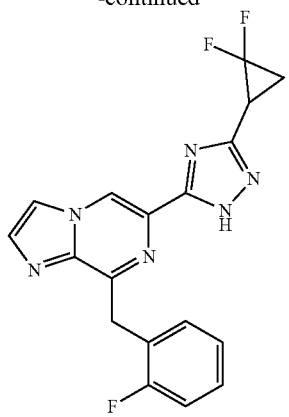
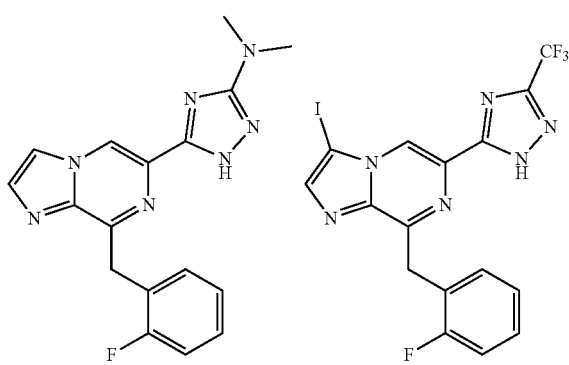
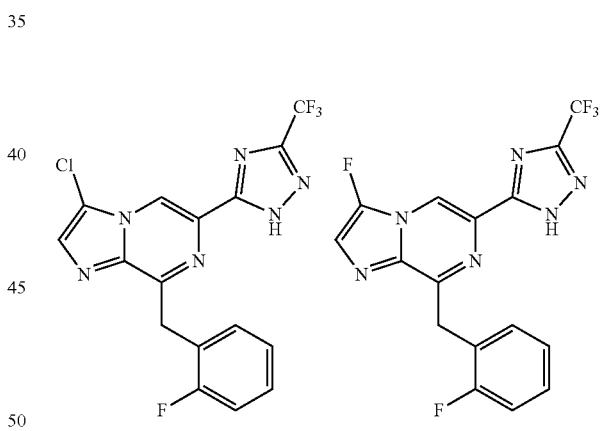
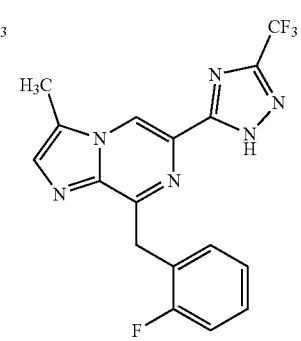

-continued

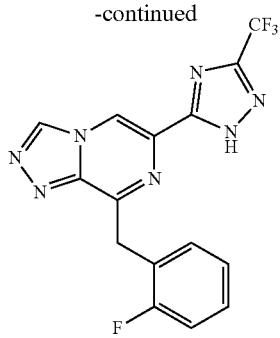

In some embodiments, the compound of Formula A, B or C is either in its neutral form or as a pharmaceutically acceptable salt.

In some embodiments of the above methods, uses and pharmaceutical compositions, the sGC stimulator is a compound depicted below:

riociguat (BAY 63-2521, Adempas®, FDA approved drug, described in DE19834044):

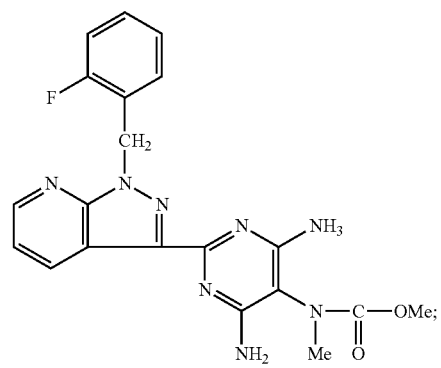 [SMILES: COC(=O)N(C)c1c(N)nc(-c2nn(Cc3ccccc3F)c3ncccc23)nc1N]

neliciguat (BAY 60-4552, described in WO 2003095451):

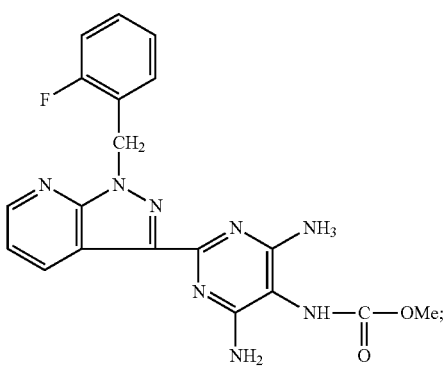 [SMILES: COC(=O)Nc1c(N)nc(-c2nn(Cc3ccccc3F)c3ncccc23)nc1N]

vericiguat (BAY 1021189):

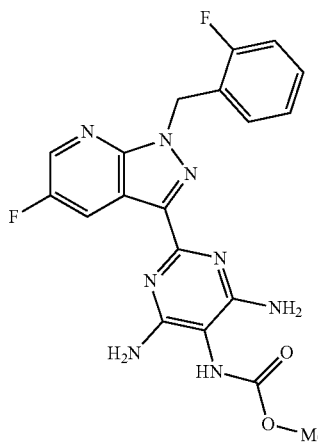

BAY 41-2272 (described in DE19834047 and DE19942809):

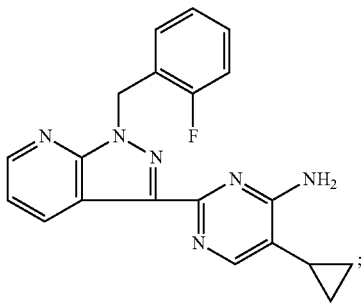 [SMILES: Nc1nc(-c2nn(Cc3ccccc3F)c3ncccc23)ncc1C1CC1]

BAY 41-8543 (described in DE19834044):

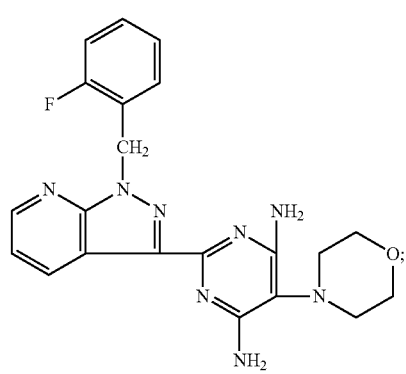 [SMILES: Nc1nc(-c2nn(Cc3ccccc3F)c3ncccc23)nc(N)c1N1CCOCC1]

etriciguat (described in WO 2003086407):

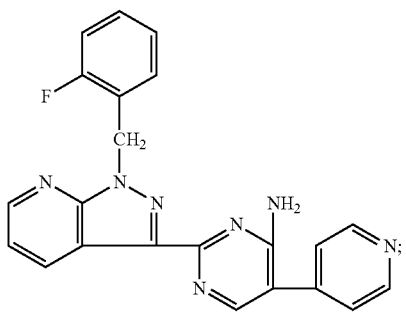 [SMILES: Nc1nc(-c2nn(Cc3ccccc3F)c3ncccc23)ncc1-c1ccncc1]

or
one of the compounds depicted below and described in US20130072492 (WO 2011149921):

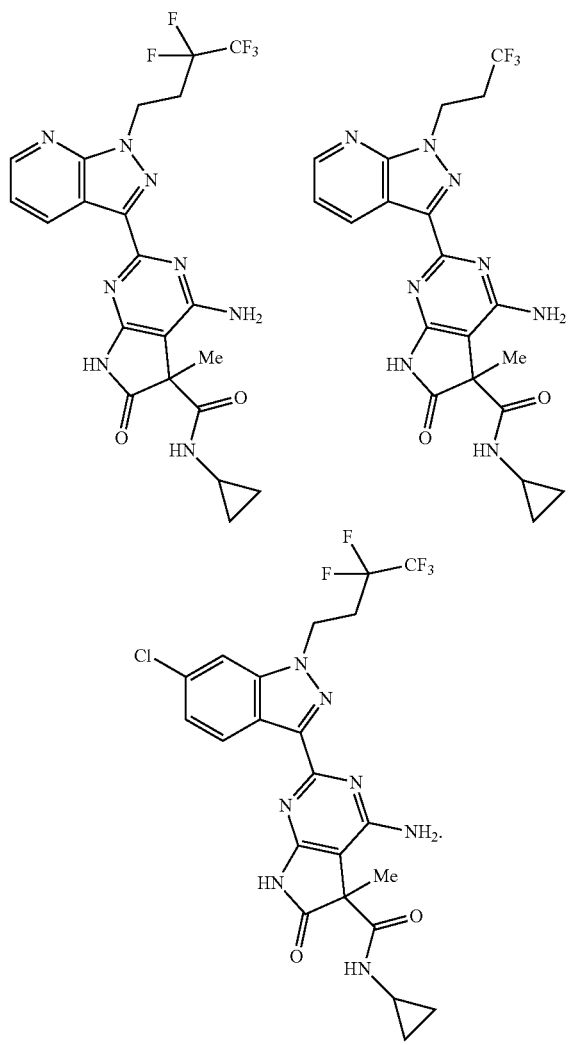

Pharmaceutically Acceptable Salts

In some embodiments of the methods, uses and pharmaceutical compositions, the sGC stimulator may be provided as (i) the compound itself (e.g., as the free base); (ii) a pharmaceutically acceptable salt of the compound; or (iii) part of a pharmaceutical composition. In some embodiments of the above methods, uses and pharmaceutical compositions, the additional therapeutic agent may be provided as (i) the compound itself (e.g., as the free base); (ii) a pharmaceutically acceptable salt of the compound; (iii) or part of a pharmaceutical composition.

A "pharmaceutically acceptable salt" of the compounds described herein include those derived from said compounds when mixed with inorganic or organic acids or bases. In some embodiments, the salts can be prepared in situ during the final isolation and purification of the compounds. In other embodiments the salts can be prepared from the free form of the compound in a separate synthetic step. The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety. The pharmaceutically acceptable salts of a sGC stimulator are those that may be used in medicine. Salts that are not pharmaceutically acceptable may, however, be useful in the preparation of a sGC stimulator or of their pharmaceutically acceptable salts.

When a sGC stimulator is acidic, suitable "pharmaceutically acceptable salts" refers to salts prepared from pharmaceutically acceptable non-toxic bases including inorganic and organic bases. Salts derived from inorganic bases include aluminum, ammonium, calcium, copper, ferric, ferrous, lithium, magnesium, manganic, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines, arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a sGC stimulator is basic, salts may be prepared from pharmaceutically acceptable non-toxic acids, including inorganic and organic acids. Such acids include acetate, acetic, acid citrate, acid phosphate, ascorbate, benzenesulfonic, benzenesulfonate, benzoic, benzoate, bromide, bisulfate, bitartrate, camphorsulfonic, chloride, citrate, citric, ethanesulfonate, ethanesulfonic, formate, fumarate, fumaric, gentisinate, gluconate, gluconic, glucuronate, glutamate, glutamic, hydrobromic, hydrochloric, iodide, isethionic, isonicotinate, lactate, lactic, maleate, maleic, malic, mandelic, methanesulfonic, methanesulfonate, mucic, nitrate, nitric, oleate, oxalate, pamoic, pamoate (i.e., 1,1'-methylene-bis-(2-hydroxy-3-naphthoate)), pantothenic, pantothenate, phosphate, phosphoric, saccharate, salicylate, succinic, succinate, sulfuric, sulfate, tannate, tartrate, tartaric, p-toluenesulfonate, p-toluenesulfonic acid and the like. Particular embodiments include citric, hydrobromic, hydrochloric, maleic, phosphoric, sulfuric and tartaric acids.

In addition to a sGC stimulator, their pharmaceutically acceptable salts may also be employed in compositions to treat or prevent the herein identified disorder.

Pharmaceutical Compositions and Methods of Administration

The compounds herein disclosed, and their pharmaceutically acceptable salts thereof may be formulated as pharmaceutical compositions or "formulations".

A typical formulation is prepared by mixing a sGC stimulator, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a sGC stimulator is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a sGC stimulator or pharmaceutical composition thereof) or aid in the manufacturing of the pharmaceutical product (i.e., medicament).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

The formulations may be prepared using conventional dissolution and mixing procedures. The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically effective amount of the compound to be administered will be governed by such considerations, and is the minimum amount necessary to ameliorate, cure or treat the disorder, or one or more of its symptoms.

The terms "administer", "administering" or "administration" in reference to a compound, composition or dosage form of the invention means introducing the compound into the system of the subject or patient in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g. orally (including, but not limited to solid dosage forms including hard or soft capsules (e.g. gelatin capsules), tablets, pills, powders, sublingual tablets, troches, lozenges, and granules; and liquid dosage forms including, but are not limited to, pharmaceutically acceptable emulsions, microemulsions, aqueous or oil solutions, suspensions, syrups and elixirs, by inhalation (e.g. with an aerosol, gas, inhaler, nebulizer or the like), to the ear (e.g. using ear drops), topically (e.g. using creams, gels, inhalants, liniments, lotions, ointments, patches, pastes, powders, solutions, sprays, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc.), via ear drops, via an implanted reservoir or the like, or parenterally depending on the severity and type of the disorder being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Formulations of a compound intended for oral use may be prepared according to any method known to the art for the manufacture of pharmaceutical compositions.

In solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

The oral compositions (either solid or liquid) can also include excipients and adjuvants such as dispersing or wetting agents, such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate); emulsifying and suspending agents, such as sodium carboxymethylcellulose, croscarmellose, povidone, methylcellulose, hydroxypropyl methylcelluose, sodium alginate, polyvinylpyrrolidone, gum tragacanth and gum acacia; sweetening, flavoring, and perfuming agents; and/or one or more preservatives such as ethyl or n-propyl p-hydroxy-benzoate, one or more coloring agents, one or more flavoring agents and one or more sweetening agents, such as sucrose or saccharin.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical compositions described herein may also be administered topically, especially when the target of treatment includes areas or organs readily accessible by topical application, including disorders of the eye, the ear, the skin, or the lower intestinal tract. Suitable topical formulations are readily prepared for each of these areas or organs. The active component is admixed under sterile conditions with a pharmaceutically acceptable carrier and any needed preservatives or buffers as may be required.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a sGC stimulator may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a sGC stimulator include Tween™-60, Span™-80, cetostearyl alcohol, benzyl alcohol, myristyl alcohol, glyceryl monostearate and sodium lauryl sulfate.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

Sterile injectable forms of the compositions described herein (e.g. for parenteral administration) may be aqueous or oleaginous suspension. These suspensions may be formulated according to techniques known in the art using suitable dispersing or wetting agents and suspending agents (including those described in the preceding paragraph). The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as a vegetable oil, for example *arachis* oil, olive oil, sesame oil or coconut oil, especially in their polyoxyethylated versions, or in mineral oil such as liquid paraffin. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

In another aspect, a sGC stimulator or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert. In the veterinary art and are compatible with the active ingredient. These veterinary compositions may be administered parenterally, orally or by any other desired route.

Combination Therapies

As used herein, the terms "in combination" or "co-administration" can be used interchangeably to refer to the use of more than one therapy (e.g., an sGC stimulator and one or more additional therapeutic agents). The use of the terms does not restrict the order in which therapies (e.g., the sGC stimulator and the additional therapeutic agents) are administered to a subject.

In some embodiments, the sGC stimulator is administered prior to, at the same time or after the initiation of treatment with another therapeutic agent.

In some embodiments of the above methods and uses, the additional therapeutic agent and the sGC stimulator are administered simultaneously. In other embodiments of the above methods and uses, the additional therapeutic agent and the sGC stimulator are administered sequentially or separately.

In some embodiments, the above pharmaceutical compositions comprise (a) an sGC stimulator as discussed above or a pharmaceutically acceptable salt thereof, and (b) a pharmaceutically acceptable carrier, vehicle or adjuvant. In some embodiments, the pharmaceutical composition comprises (a) one or more additional therapeutic agents as discussed above, or a pharmaceutically acceptable salt thereof, and (b) a pharmaceutically acceptable carrier, vehicle or adjuvant. In some embodiments, the pharmaceutical composition comprises (i) an sGC stimulator as discussed above, or a pharmaceutically acceptable salt thereof, (ii) one or more additional therapeutic agents as discussed above, or a pharmaceutically acceptable salt thereof, and (iii) a pharmaceutically acceptable carrier, vehicle or adjuvant.

The sGC stimulators and pharmaceutical compositions described herein can be used in combination therapy with one or more additional therapeutic agents. For combination treatment with more than one active agent, the additional active agents may be in the same dosage form or in separate dosage forms. Wherein the additional active agents are present in separate dosage forms, the active agents may be administered separately or in conjunction with the sGC stimulator. In addition, the administration of one agent may be prior to, concurrent to, or subsequent to the administration of the other agent.

When used in combination therapy with other agents, a "therapeutically effective amount" of the sGC stimulator and of the other agent or agents will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed.

In some embodiments, co-administration or combination therapy encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order.

When co-administration involves the separate administration of a first amount of a sGC stimulator and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a sGC stimulator and the second therapeutic agent can be administered in any order within about 24 hours of each other, within about 16 hours of each other, within about 8 hours of each other, within about 4 hours of each other, within about 1 hour of each other or within about 30 minutes of each other.

Examples of other therapeutic agents that may be combined with a sGC stimulator, or a pharmaceutically acceptable salt thereof, either administered separately or in the same pharmaceutical composition include, but are not limited to:

(1) Endothelium-derived releasing factor (EDRF) or NO gas.
(2) NO donors such as a nitrosothiol, a nitrite, a sydnonimine, a NONOate, a N-nitrosamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitroglycerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; isosorbide (Dilatrate®-SR, Imdur®, Ismo®, Isordil®, Isordil®, Titradose®, Monoket®), 3-morpholinosydnonimine; linsidomine chlorohydrate ("SIN-i"); S-nitroso-N-acetylpenicillamine ("SNAP"); S-nitrosoglutathione (GSNO), sodium nitroprusside, S-nitrosoglutathione mono-ethyl-ester (GSNO-ester), 6-(2-hydroxy-1-methyl-nitrosohydrazino)-N-methyl-1-hexanamine or diethylamine NONOate.
(3) Other substances that enhance cGMP concentrations such as protoporphyrin IX, arachidonic acid and phenyl hydrazine derivatives.
(4) Nitric Oxide Synthase substrates: for example, L-arginine, n-hydroxyguanidine based analogs, such as N[G]-hydroxy-L-arginine (NOHA), 1-(3, 4-dimethoxy-2-chlorobenzylideneamino)-3-hydroxyguanidine, and PR5 (1-(3, 4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine.
(5) Compounds which enhance eNOS transcription.
(6) NO independent heme-independent sGC activators, including, but not limited to:
BAY 58-2667 (described in patent publication DE19943635); HMR-1766 (ataciguat sodium, described in patent publication WO2000002851); S 3448 (2-(4-chloro-phenylsulfonylamino)-4,5-dimethoxy-N-(4-(thiomorpholine-4-sulfonyl)-phenyl)-benzamide (described in patent publications DE19830430 and WO2000002851); and
HMR-1069 (Sanofi-Aventis).
(7) Heme-dependent, NO-independent sGC stimulators including, but not limited to:
YC-1 (see patent publications EP667345 and DE19744026); riociguat (BAY 63-2521, Adempas®, described in DE19834044); neliciguat (BAY 60-4552, described in WO 2003095451); vericiguat (BAY 1021189); BAY 41-2272 (described in DE19834047 and DE19942809); BAY 41-8543 (described in DE19834044); etriciguat (described in WO 2003086407); CFM-1571 (described in patent publication WO2000027394); A-344905, its acrylamide analogue A-350619 and the aminopyrimidine analogue A-778935;
other sGC stimulators described in one of publications US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132) and Tetrahedron Letters (2003), 44(48): 8661-8663; and
IW-1973 and IW1701.
(8) Compounds that inhibit the degradation of cGMP and/or cAMP, such as:
PDE1 inhibitors, PDE2 inhibitors, PDE-3 inhibitors such as, for example, amrinone, milrinone, enoximone, vesnarinone, pimobendan, and olprinone, PDE4 inhibitors, such as, for example, rolumilast, PDE5 inhibitors, such as, for example, sildenafil (Viagra©) and related agents such as avanafil, lodenafil, mirodenafil, sildenafil citrate (Revatio®), tadalafil (Cialis© or Adcirca®), vardenafil (Levitra©) and udenafil; alprostadil; dipyridamole and PF-00489791; PDE6 inhibitors, PDE9 inhibitors, such as, for example, PF-04447943, PDE10 inhibitors such as, for example, PF-02545920 (PF-10), and PDE11 inhibitors.
(9) Calcium channel blockers of the following types:
dihydropyridine calcium channel blockers such as amlodipine (Norvasc®), aranidipine (Sapresta®), azelnidipine (Calblock®), barnidipine (HypoCa®), benidipine (Coniel®), cilnidipine (Atelec®, Cinalong®, Siscard®), clevidipine (Cleviprex®), diltiazem, efonidipine (Landel®), felodipine (Plendil®), lacidipine (Motens®, Lacipil®), lercanidipine (Zanidip®), manidipine (Calslot®, Madipine®), nicardipine (Cardene®, Carden SR®), nifedipine (Procardia®, Adalat®), nilvadipine (Nivadil®), nimodipine (Nimotop®), nisoldipine (Baymycard®, Sular®, Syscor®), nitrendipine (Cardif®, Nitrepin®, Baylotensin®), pranidipine (Acalas®), and isradipine (Lomir®);
phenylalkylamine calcium channel blockers such as verapamil (Calan®, Isoptin®); and gallopamil (Procorum®, D600);
benzothiazepines such asdiltiazem (Cardizem®); and
nonselective calcium channel inhibitors such as mibefradil, bepridil, fluspirilene, and fendiline.
(10) Endothelin receptor antagonists (ERAs) such as the dual (ETA and $ET_B$) endothelin receptor antagonist bosentan (Tracleer®), sitaxentan (Thelin®) or ambrisentan (Letairis®).
(11) Prostacyclin derivatives or analogues, such asprostacyclin (prostaglandin $I_2$), epoprostenol (synthetic prostacyclin, Flolan®), treprostinil (Remodulin®), iloprost (Ilomedin®), iloprost (Ventavis®); and oral and inhaled forms of Remodulin® under development.
(12) Antihyperlipidemics such as the following types:
bile acid sequestrants like cholestyramine, colestipol, colestilan, colesevelam or sevelamer;
statins like atorvastatin, simvastatin, lovastatin, fluvastatin, pitavastatin, rosuvastatin and pravastatin;
cholesterol absorption inhibitors such as ezetimibe;
other lipid lowering agents such as icosapent ethyl ester, omega-3-acid ethyl esters, reducol;

fibric acid derivatives such as clofibrate, bezafibrate, clinofibrate, gemfibrozil, ronifibrate, binifibrate, fenofibrate, ciprofibrate, choline fenofibrate;

nicotinic acid derivatives such as acipimox and niacin;

combinations of statins, niacin and intestinal cholesterol absorption-inhibiting supplements (ezetimibe and others) and fibrates; and antiplatelet therapies such as clopidogrel bisulfate.

(13) Anticoagulants, such as the following types:

coumarines (Vitamin K antagonists) such as warfarin (Coumadin®), cenocoumarol, phenprocoumon and phenindione;

heparin and derivatives such as low molecular weight heparin, fondaparinux and idraparinux;

direct thrombin inhibitors such as argatroban, lepirudin, bivalirudin, dabigatran and ximelagatran (Exanta®); and tissue-plasminogen activators, used to dissolve clots and unblock arteries, such as alteplase.

(14) Antiplatelet drugs such as, for instance, topidogrel, ticlopidine, dipyridamoleand aspirin.

(15) ACE inhibitors, for example the following types:

sulfhydryl-containing agents such as captopril (Capoten®) and zofenopril;

dicarboxylate-containing agents such as enalapril (Vasotec/Renitec®), ramipril (Altace®/Tritace®/Ramace®/Ramiwin®), quinapril (Accupril®), perindopril (Coversyl®/Aceon®), lisinopril (Lisodur®/Lopril®/Novatec®/Prinivil®/Zestril®) and benazepril (Lotensin®);

phosphonate-containing agents such as fosinopril;

naturally occurring ACE inhibitors such as casokinins and lactokinins, which are breakdown products of casein and whey that occur naturally after ingestion of milk products, especially cultured milk;

the lactotripeptides Val-Pro-Pro and Ile-Pro-Pro produced by the probiotic *Lactobacillus helveticus* or derived from casein also having ACE-inhibiting and antihypertensive functions;

other ACE inhibitors such as alacepril, delapril, cilazapril, imidapril, trandolapril, temocapril, moexipril and pirapril.

(16) Supplemental oxygen therapy.

(17) Beta blockers, such as the following types:

non-selective agents such as alprenolol, bucindolol, carteolol, carvedilol, labetalol, nadolol, penbutolol, pindolol, oxprenonol, acebutolol, sotalol, mepindolol, celiprolol, arotinolol, tertatolol, amosulalol, nipradilol, propranolol and timolol;

$\beta_1$-Selective agents such as cebutolol, atenolol, betaxolol, bisoprolol, celiprolol, dobutamine hydrochloride, irsogladine maleate, carvedilol, talinolol, esmolol, metoprolol and nebivolol; and $\beta_2$-Selective agents such as butaxamine.

(18) Antiarrhythmic agents such as the following types:

Type I (sodium channel blockers) such as quinidine, lidocaine, phenytoin, propafenone;

Type III (potassium channel blockers) such as amiodarone, dofetilide and sotalol; and Type V such as adenosine and digoxin.

(19) Diuretics such as thiazide diuretics, for example chlorothiazide, chlorthalidone and hydrochlorothiazide, bendroflumethiazide, cyclopenthiazide, methyclothiazide, polythiazide, quinethazone, xipamide, metolazone, indapamide, cicletanine; loop diuretics, such as furosemide and toresamide; potassium-sparing diuretics such as amiloride, spironolactone, canrenoate potassium, eplerenone and triamterene; combinations of these agents; other diuretics such as acetazolamid and carperitide.

(20) Direct-acting vasodilators such as hydralazine hydrochloride, diazoxide, sodium nitroprusside, cadralazine; other vasodilators such as isosorbide dinitrate and isosorbide 5-mononitrate.

(21) Exogenous vasodilators such as Adenocard® and alpha blockers.

(22) Alpha-1-adrenoceptor antagonists such as prazosin, indoramin, urapidil, bunazosin, terazosin and doxazosin; atrial natriuretic peptide (ANP), ethanol, histamine-inducers, tetrahydrocannabinol (THC) and papaverine.

(23) Bronchodilators of the following types:

short acting $\beta_2$ agonists, such as albutamol or albuterol (Ventolin®) and terbutaline;

long acting $\beta_2$ agonists (LABAs) such as salmeterol and formoterol;

anticholinergics such as pratropium and tiotropium; and theophylline, a bronchodilator and phosphodiesterase inhibitor.

(24) Corticosteroids such as beclomethasone, methylprednisolone, betamethasone, prednisone, prednisolone, triamcinolone, dexamethasone, fluticasone, flunisolide, hydrocortisone, and corticosteroid analogs such as budesonide.

(25) Dietary supplements such as, for example omega-3 oils; folic acid, niacin, zinc, copper, Korean red ginseng root, ginkgo, pine bark, Tribulus *terrestris*, arginine, *Avena sativa*, horny goat weed, maca root, muira puama, saw palmetto, and Swedish flower pollen; vitamin C, Vitamin E, Vitamin K2; testosterone supplements, testosterone transdermal patch; zoraxel, naltrexone, bremelanotide and melanotan II.

(26) PGD2 receptor antagonists.

(27) Immunosuppressants such as cyclosporine (cyclosporine A, Sandimmune®, Neoral®), tacrolimus (FK-506, Prograf®), rapamycin (Sirolimus®, Rapamune®) and other FK-506 type immunosuppressants, mycophenolate, e.g., mycophenolate mofetil (CellCept®).

(28) Non-steroidal anti-asthmatics such as β2-agonists like terbutaline, metaproterenol, fenoterol, isoetharine, albuterol, salmeterol, bitolterol and pirbuterol; β2-agonist-corticosteroid combinations such as salmeterol-fluticasone (Advair®), formoterol-budesonide (Symbicort®), theophylline, cromolyn, cromolyn sodium, nedocromil, atropine, ipratropium, ipratropium bromide and leukotriene biosynthesis inhibitors (zileuton, BAY1005).

(29) Non-steroidal anti-inflammatory agents (NSAIDs) such as propionic acid derivatives like alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen); acetic acid derivatives such as indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac; fenamic acid derivatives such as flufenamic acid, meclofenamic acid, mefenamic acid, niflumic acid and tolfenamic acid; biphenylcarboxylic acid derivatives such as diflunisal and flufenisal; oxicams such as isoxicam, piroxicam, sudoxicam and tenoxican; salicylates such as acetyl salicylic acid and sulfasalazine; and the pyrazolones such as apazone, bezpiperylon, feprazone, mofebutazone, oxyphenbutazone and phenylbutazone.

(30) Cyclooxygenase-2 (COX-2) inhibitors such as celecoxib (Celebrex®), rofecoxib (Vioxx®), valdecoxib, etoricoxib, parecoxib and lumiracoxib; opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine;

(31) Anti-diabetic agents such as insulin and insulin mimetics; sulfonylureas such as glyburide, glybenclamide, glipizide, gliclazide, gliquidone, glimepiride, meglinatide, tolbutamide, chlorpropamide, acetohexamide and olazamide; biguanides such as metformin (Glucophage®); a-glucosidase inhibitors such as acarbose, epalrestat, voglibose, miglitol; thiazolidinone compounds such as rosiglitazone (Avandia®), troglitazone (Rezulin®), ciglitazone, pioglitazone (Actos®) and englitazone; insulin sensitizers such as pioglitazone and rosiglitazone; insulin secretagogues such as repaglinide, nateglinide and mitiglinide; incretin mimetics such as exanatide and liraglutide; amylin analogues such as pramlintide; glucose lowering agents such as chromium picolinate, optionally combined with biotin; dipeptidyl peptidase IV inhibitors such as sitagliptin, vildagliptin, saxagliptin, alogliptin and linagliptin: glucagon-like peptide 1 receptor agonists such as liraglutide (Victoza®, Saxenda®), semaglutide (Ozempic®), exenatide (Byetta®/Bydureon®), lixisenatide (Lyxumia®) albiglutide (Tanzeum®), dulaglutide (Trulicity®), and taspoglutide.

(32) HDL cholesterol-increasing agents such as anacetrapib and dalcetrapib.

(33) Antiobesity drugs such as methamphetamine hydrochloride, amfepramone hydrochloride (Tenuate®), phentermine (Ionamin®), benzfetamine hydrochloride (Didrex®), phendimetrazine tartrate (Bontril®, Prelu-2 ®, Plegine®), mazindol (Sanorex®), orlistat (Xenical®), sibutramine hydrochloride monohydrate (Meridia®, Reductil®), rimonabant (Acomplia®), amfepramone, chromium picolinate; combination such as phentermine/topiramate, bupropion/naltrexone, sibutramine/metformin, bupropion SR/zonisamide SR, salmeterol, xinafoate/fluticasone propionate; lorcaserin hydrochloride, phentermine/topiramate, cetilistat, exenatide, liraglutide, semaglutide, metformin hydrochloride, sibutramine/metformin, bupropion SR/zonisamide SR, CORT-108297, canagliflozin, chromium picolinate, GSK-1521498, LY-377604, metreleptin, obinepitide, P-57AS3, PSN-821, salmeterol xinafoate/fluticasone propionate, sodium tungstate, somatropin (recombinant), tesamorelin, tesofensine, velneperit, zonisamide, beloranib hemioxalate, insulinotropin, resveratrol, sobetirome, tetrahydrocannabivarin and beta-lapachone.

(34) Angiotensin receptor blockers such as losartan, valsartan, candesartan, cilexetil, eprosaran, irbesartan, telmisartan, olmesartan, medoxomil, azilsartan and medoxomil.

(35) Renin inhibitors such as aliskiren hemifumirate.

(36) Centrally acting alpha-2-adrenoceptor agonists such as methyldopa, clonidine and guanfacine.

(37) Adrenergic neuron blockers such as guanethidine and guanadrel.

(38) Imidazoline I-1 receptor agonists such as rimenidine dihydrogen phosphate and moxonidine hydrochloride hydrate.

(39) Aldosterone antagonists such as spironolactone and eplerenone.

(40) Potassium channel activators such as pinacidil.

(41) Dopamine D1 agonists such as fenoldopam mesilate; other dopamine agonists such as ibopamine, dopexamine and docarpamine.

(42) 5-HT2 antagonists such as ketanserin.

(43) Vasopressin antagonists such as tolvaptan.

(44) Calcium channel sensitizers such as levosimendan or activators such as nicorandil.

(45) Adenylate cyclase activators such as colforsin dapropate hydrochloride.

(46) Positive inotropic agents such as digoxin and metildigoxin; metabolic cardiotonic agents such as ubidecarenone; brain natriuretic peptides such as nesiritide.

(47) Drugs used for the treatment of erectile dysfunction such as alprostadil, aviptadil, and phentolamine mesilate.

(48) Drugs used in the treatment of obesity, including but not limited to, methamphetamine hydrochloride (Desoxyn®), amfepramone hydrochloride (Tenuate®), phentermine (Ionamin®), benzfetamine hydrochloride (Didrex®), phendimetrazine hydrochloride (Bontril®, Prelu-2®, Plegine®), mazindol (Sanorex®) and orlistat (Xenical®).

(49) Drugs used for the treatment of Alzheimer's disease and dementias such as the following types: acetyl cholinesterase inhibitors including galantamine (Razadyne®), rivastigmine (Exelon®), donepezil (Aricept®) and tacrine (Cognex®); NMDA receptor antagonists such as memantine (Namenda®); and oxidoreductase inhibitors such as idebenone.

(50) Psychiatric medications such as the following types:
ziprasidone (Geodon™), risperidone (Risperdal™), olanzapine (Zyprexa™) valproate;
dopamine D4 receptor antagonists such as clozapine;
dopamine D2 receptor antagonists such as nemonapride;
mixed dopamine D1/D2 receptor antagonists such as zuclopenthixol; GABA A receptor modulators such as carbamazepine;
sodium channel inhibitors such as lamotrigine;
monoamine oxidase inhibitors such as moclobemide and indeloxazine; and primavanserin, and perospirone.

(51) Drugs used for the treatment of movement disorders or symptoms such as the following types:
catechol-O-methyl transferase inhibitors such as entacapone;
monoamine oxidase B inhibitors such as selegiline;
dopamine receptor modulators such as levodopa;
dopamine D3 receptor agonists such as pramipexole;
decarboxylase inhibitors such as carbidopa;
other dopamine receptor agonists such as pergolide, ropinirole, cabergoline;
ritigonide, istradefylline, talipexole; zonisamide and safinamide; and
synaptic vesicular amine transporter inhibitors such as tetrabenazine.

(52) Drugs used for the treatment of mood or affective disorders or OCD such as the following types:
tricyclic antidepressants such as amitriptyline (Elavil®), desipramine (Norpramin®), imipramine (Tofranil®), amoxapine (Asendin®), nortriptyline and clomipramine;

selective serotonin reuptake inhibitors (SSRIs) such as paroxetine (Paxil®), fluoxetine (Prozac®), sertraline (Zoloft®), and citralopram (Celexa®);
doxepin (Sinequan®), trazodone (Desyrel®) and agomelatine;
selective norepinephrine reuptake inhibitors (SNRIs) such as venlafaxine, reboxetine and atomoxetine; dopaminergic antidepressants such as bupropion and amineptine.
(53) Drugs for the enhancement of synaptic plasticity such as the following types:
nicotinic receptor antagonists such as mecamylamine; and mixed 5-HT, dopamine and norepinephrine receptor agonists such as lurasidone.
(54) Drugs used for the treatment of ADHD such as amphetamine; 5-HT receptor modulators such as vortioxetine and alpha-2 adrenoceptor agonists such as clonidine.
(55) Neutral endopeptidase (NEP) inhibitors such as sacubitril, omapatrilat; and Methylene blue (MB).
(56) Nitric oxide synthase cofactors such as: tetrahydrobiopterin, dihydrobiopterin, and sapropterin (Kuvan®).
(57) Treatments for mitochondrial disorders including, but not limited to, vitamins and supplements, including Coenzyme Q10; B complex vitamins, especially thiamine (B1) and riboflavin (B2); Alpha lipoic acid; L-carnitine (Carnitor); Creatine; Citrulline, and L-Arginine.
(58) Treatments for epilespsy or seizures including, but not limited to, phenytoin (Dilantin®), valproic acid (Depakote®), phenobarbital, lamotrigine (Lamictal®), carbamazepine (Tegretol®), topiramate (Topamax®), oxcarbazepine (Trileptal®), zonisamide (Zonegran®), gabapentin (Neurontin®), levetiracetam (Keppra®), pregabalin (Lyrica®), clonazepam (Klonopin®), lacosamide (Vimpat®), rufinamide (Banzel®), and vigabatrin (Sabril®).

Packaging and Kits

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

Examples

| Compound Number | Compound Structure |
|---|---|
| Compound A | 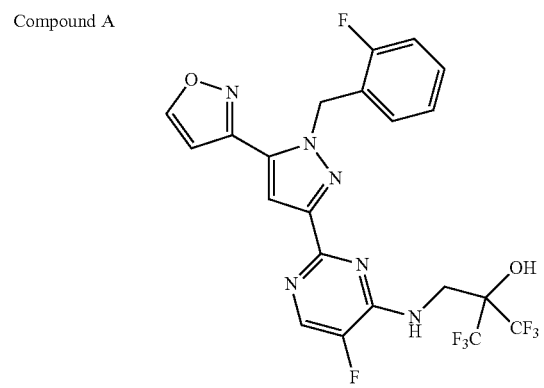 |
| Compound B | 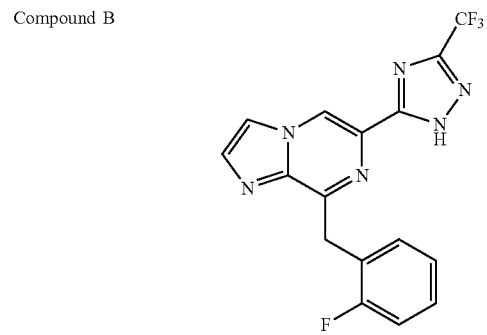 |
| Compound D | 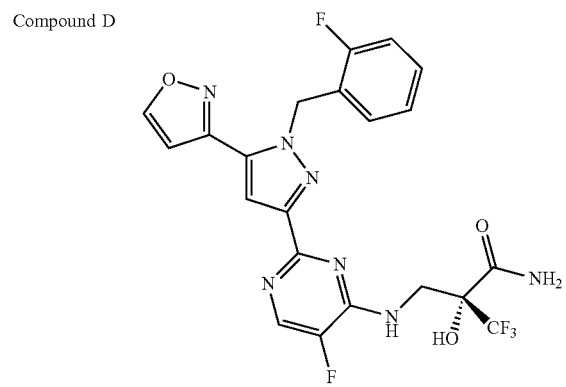 |

| Compound Number | Compound Structure |
|---|---|
| Compound E | (structure: fluorobenzyl-pyrazolopyridine linked to trifluoromethyl-triazole) |
| Vericiguat | (structure: fluorobenzyl-fluoropyrazolopyridine linked to diaminopyrimidine with methyl carbamate) |

Example 1. In Vivo Models

Peroxisome proliferator-activated receptor c coactivator 1α (PGC1α) is the master regulator of mitochondrial biogenesis, and a mediator of metabolic and mitochondrial function (see Journal of Cell Science 125 (21) 4964-4971 and Cardiovascular Research (2008) 79, 208-217, the teachings of which are incorporated herein by reference). Additionally, PGC1α exerts effects on downstream effectors such as PPARα and PPARγ to modify mitochondrial energy metabolism under a variety of physiological conditions (see Journal of Clinical Investigation (2006) 116(3):615-622). Upon changes in the ATP-to-AMP ratio, AMPK is activated and phosphorylates downstream targets to redirect metabolism towards increased catabolism and decreased anabolism. AMPK functions as a central mediator of the cellular response to energetic stress and mitochondrial insults and coordinates multiple features of autophagy and mitochondrial biology (See Nature Reviews Molecular Cell Biology volume 19, pages 121-135 (2018)). Mitochondrial density and/or function are reduced in mitochondrial diseases and diseases associated with mitochondrial dysfunction.

The role of sGC stimulators on biomarkers of mitochondrial biogenesis (PGC1α) and function (AMPK, PPARα and PPARγ) was evaluated in three animal models of mitochondrial dysfunction, the ZSF1 rat (see JASN (2007) 18(11 2945-2952), the diet-induced obese (DIO) mouse (see PLoS ONE (2013) 8(12):e81870), and the carbon tetrachloride ($CCl_4$) rat (see Hepatology (1990) 12(3) 526-532 and Liver International (2017) 37(7)). The ZSF1 and $CCl_4$ animal models exhibit abnormal levels of PGC1α, AMPK, PPARα and PPARγ gene expression and their levels were normalized by treatment with sGC stimulators. For each of these models, PCG1α is increased with treatment of compound B as compared to the disease state.

Methods:

Model 1: Diet-Induced Obesity (DIO) Mouse Model

Animals were fed either chow or high fat diet (Research Diets). The lean mice were maintained on a standard chow diet. The obese mice were given 60% high fat diet (HFD) starting at 6 weeks of age. All animals were allowed free access to drinking water and chow. The study began when the mice were 12 weeks of age and concluded after 4 weeks (16 weeks of age). The obese control group was maintained on HFD. Groups receiving compound treatments were fed with HFD containing 90 mg Compound A/kg diet (an approximate dose of 6 mg/kg) or 45 mg vericiguat/kg diet (an approximate dose of 3 mg/kg). Body weights were determined twice weekly and food intake was measured daily for 28 days. On the terminal day (28 days), the white adipose tissue (WAT) and liver were collected, weighed and snap frozen in liquid nitrogen for further analysis.

In a separate study with DIO mouse model, the obese mice were treated with HFD containing different doses of Compound B in diet (38.8 mg, 128.6 mg or 386.2 mg/kg diet, approximate dose of 0.05 mg/kg, 3 mg/kg and 10 mg/kg). On the terminal day, hypothalamus was collected, snap frozen in liquid nitrogen for further analysis.

Model 2: ZSF1 Rat Model

There are 4 groups of animals in the study design:
1. ZSF1 Lean—Vehicle (n=6)
2. ZSF1 Obese—Vehicle (n=9)
3. ZSF1 Obese—Compound A 10 mg/kg/day (n=9)
4. ZSF1 Obese—Enalapril 3 mg/kg/day+Compound A 10 mg/kg/day (n=9)

Animals in Group 4 was placed on drinking water containing enalapril and kept on Purina 5008 rodent chow (C13000). Animals in Groups 1-3 were kept on Purina 5008 rodent chow and drinking water. Ten days after the initiation of enalapril treatment, Groups 3 and 4 received Compound A at 10 mg/kg/day, respectively for 11 weeks (monotherapy). Beginning on day 10, animals in Groups 3 and 4 received Compound A at 10 mg/kg/day in addition to enalapril for an additional 11 weeks (combination therapy).

In a separate study with ZSF1 rats, the obese rats were treated with Compound D alone (monotherapy) or in combination with enalapril (combination therapy), following the same protocol of the study above with Compound A.

Model 3: Carbon Tetrachloride ($CCl_4$) Rat Model

Male, Sprague-Dawley rat were dosed with 0.25 ml/kg of $CCl_4$ PO three times a week diluted in corn oil for the duration of the study (8 weeks). Control animals received an equivalent volume of corn oil. Two weeks after beginning the administration of $CCl_4$, animals were given a chow admixture containing Compound A calculated to achieve doses of 3 mg/kg/day.

B-DNA Assay

For gene expression analysis, 5-10 mg of tissue samples from ZSF1 rat liver, $CCl_4$ rat liver, or DIO mice brain hypothalamus, or approximately 50 mg of white adipose tissue (WAT) from ZSF1 rat were homogenized and processed using QuantiGene sample processing kit according to manufacturer's instruction (Affymatrix, Fremont, CA). Gene expression in the tissue samples was measured using a QuantiGene 2.0 Plex Assay kit (Affymetrix) and multiplex gene panel specifically designed for each animal model following manufacture instructions. Analytes were measured using Luminex MAGPIX™ (Bio-Rad, Hercules, CA). Median fluorescence intensity (MFI) was generated for each gene target and normalized to the geometric mean expression of selected housekeeping genes, which were chosen to match the target transcript abundance.

Results from In Vivo Animal Models

Figure 1B:
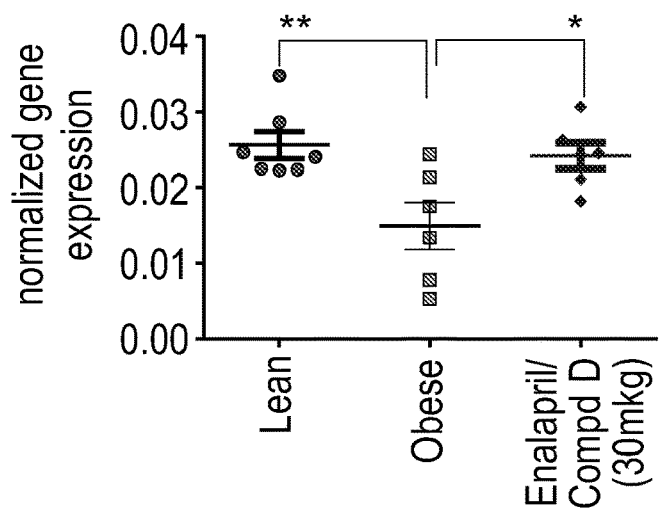
Figure 1C:
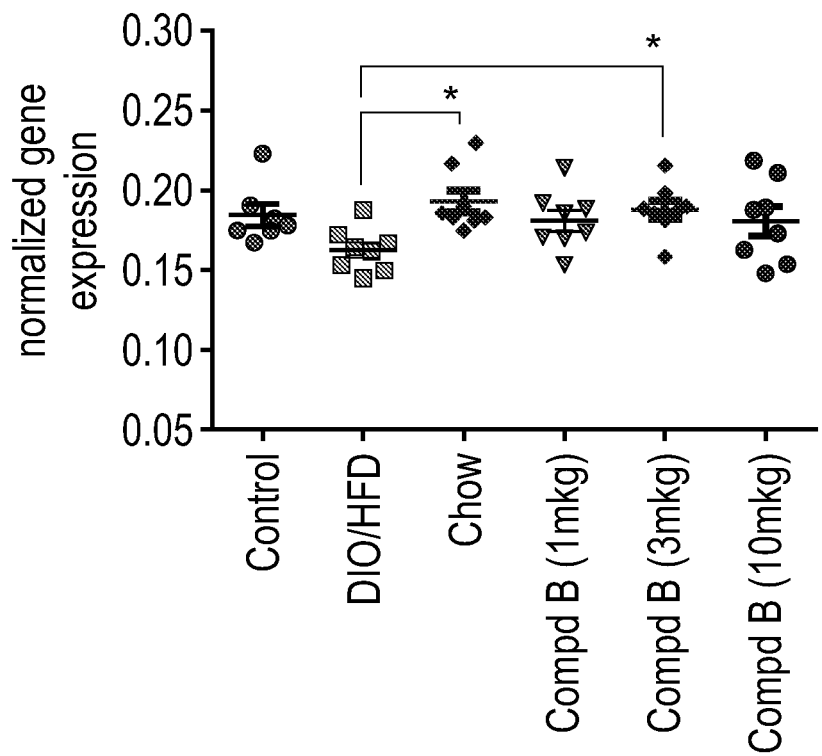

Gene expression profile analysis by B-DNA assay demonstrated that PGC1α, the "master switch" in regulating genes involved in energy metabolism, was significantly decreased in the disease conditions of ZSF1 rats, and DIO mice (FIG. 1). Treatment of ZSF1 obese rats with sGC stimulators, Compound A at 10 mg/kg, or Compound D at 30 mg/kg, in combination with enalapril at 3 mg/kg, increased gene expression levels of PGC1α in white adipose tissue (WAT) and liver, respectively (FIGS. 1A and 1B). In addition, Compound B, increased PGC1α expression significantly in DIO mice hypothalamus (FIG. 1C).

Figure 2A:
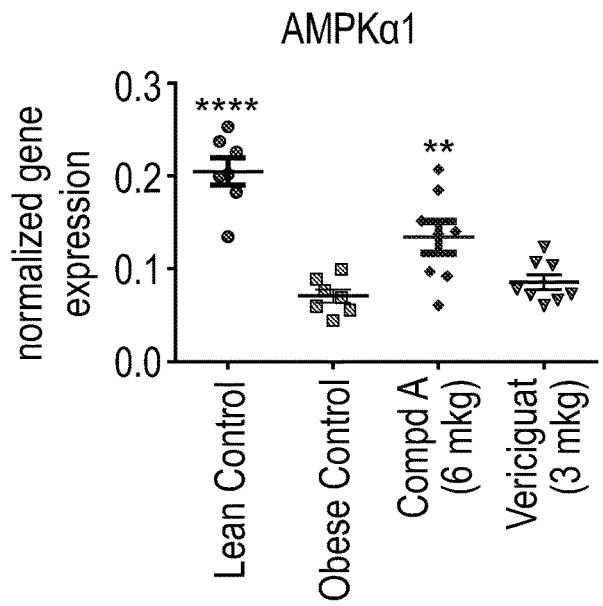
FIGS. 2A, 2B and 2C are plots of the gene expression level of (A) AMPKα1 in the eWAT of DIO mice, (B) Pparα in the eWAT tissue of DIO mice, and (C) Pparα in the liver tissue of carbon tetrachloride ($CCl_4$) rats.
Figure 2B:
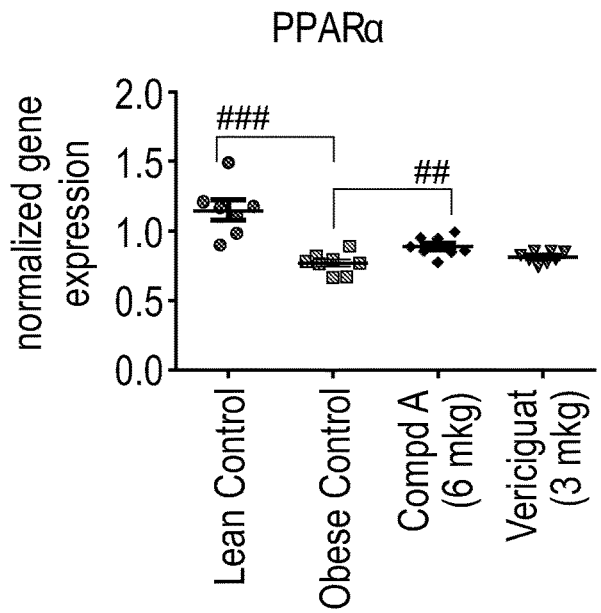
Figure 2C:
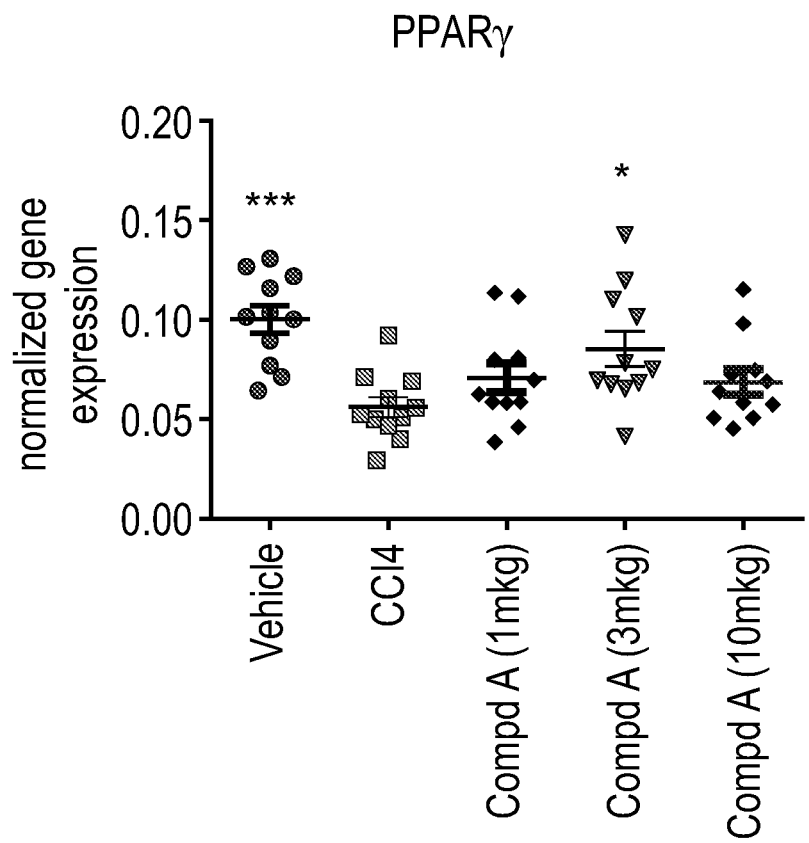

Besides PGC1α, three other genes involved in mitochondrial biogenesis and function, AMPK, PPARα and PPARγ were also down-regulated by disease conditions in DIO mice and CCl4 rats (FIG. 2). Treatment of DIO-induced obese mice or CCl$_4$-treated rats with Compound A at 6 mg/kg increased gene expression levels of AMPK and Pparα in DIO mice WAT (FIGS. 2A and 2B; Compound A at 3 mg/kg increased Pparγ in CCl$_4$ rat liver (FIG. 2C).

Conclusion: Compounds A, B, and D increased gene expression levels of genes required for mitochondrial biogenesis (PGC1α) and function (AMPK, Pparα and Pparγ) in multiple pre-clinical animal models suggesting that administration of an sGC stimulator would improve mitochondrial function.

Example 2—Mitochondrial Patient Cells

Materials
Cell Culture

Lymphoblast cells of LHON patient (GM11605 and GM10742) and Leigh patient (GM13740) were purchased from Coriell institute and cultured according to recommended growth condition from the vendor. The culture medium RPMI-1640 (ATCC, catalog #30-2006) containing 15% fetal bovine serum (Corning catalog #35-015-CV).

Methods
cGMP Measurement

On the day of the assay, Coriell cells were plated on 96-well V-bottom culture plate (Corning Catalog #3894) at density of 200,000 cells per well in 100 ul culture media. Right before the assay, cells were spun down by centrifuging in a benchtop centrifuge (Beckman Model #TJ-25) at 300 g for 5 min, media was removed and cell pellets were carefully washed once with 200 μL of HBSS containing $Ca^{2+}$ and $Mg^{2+}$ (Gibco catalog #14025-075). The cells were spun down, then 90 μL per well of HBSS containing 0.5 mM IBMX was added to the cells and were incubated at 37° C. for 15 min. Then 10 μL per well of 10× compounds (at its final conc.) diluted in HBSS solution containing IBMX plus different concentration of NO donor, DETA (final concentration of 0, 10 μM, 30 μM) was added to the cells and incubated at 37° C. for another 20 min. Cell pellets were spun down and lysed with 0.1 N HCl (100 ul/well). cGMP was measured using a cGMP Biotrak EIA kit (GE cat no. RPN226). cGMP concentrations of the samples were calculated from the standard curve.

ATP Assay

Corielll cells were plated on 96-well V-bottom culture plate (Corning Catalog #3894) at density of 200,000 cells per well in 90 ul RPMI-1640 media containing 2% FBS. Three hours later, 10 μL per well of 10× compounds (at its final conc.) diluted in RPMI-1640 media containing 2% FBS were added to the cells and incubated at 37 C for 24 hrs. The next day, ATP levels in the cells were measure using ATPlite kit (PerkinElmer Cat #6016943)

bDNA Assay

Coriell cells were plated on 96-well V-bottom culture plate (Corning Catalog #3894) at density of 200,000 cells per well in 90 ul RPMI-1640 media containing 2% FBS. Three hours later, 10 μL per well of 10× compounds (at its final conc.) diluted in RPMI-1640 media containing 2% FBS were added to the cells and incubated at 37 C for 24 hrs. The next day, cells were spun down by centrifuging in a benchtop centrifuge (Beckman Model #TJ-25) at 300 g for 5 min, media was removed and cell pellets were lysed in 100 μL/well with lysis mixture provided by QuantiGene sample processing kit (Affymetrix catalog #QS010). Gene expression in the cell lysates was measured using a QuantiGene 2.0 Plex Assay kit (Affymetrix catalog #QP1013) and multiplex gene panel (Thermo/Fisher, plex set #QGP-150-M19022101) according to manufacturer's protocols. Analytes were measured using Luminex MAGPIX™ (Bio-Rad, Hercules, CA). Median fluorescence intensity (MFI) was generated for each gene target and normalized to the geometric mean expression of three housekeeping genes (Hprt1, Ppib and Polr2a), which were chosen to match the target transcript abundance.

Results

Figure 3A:
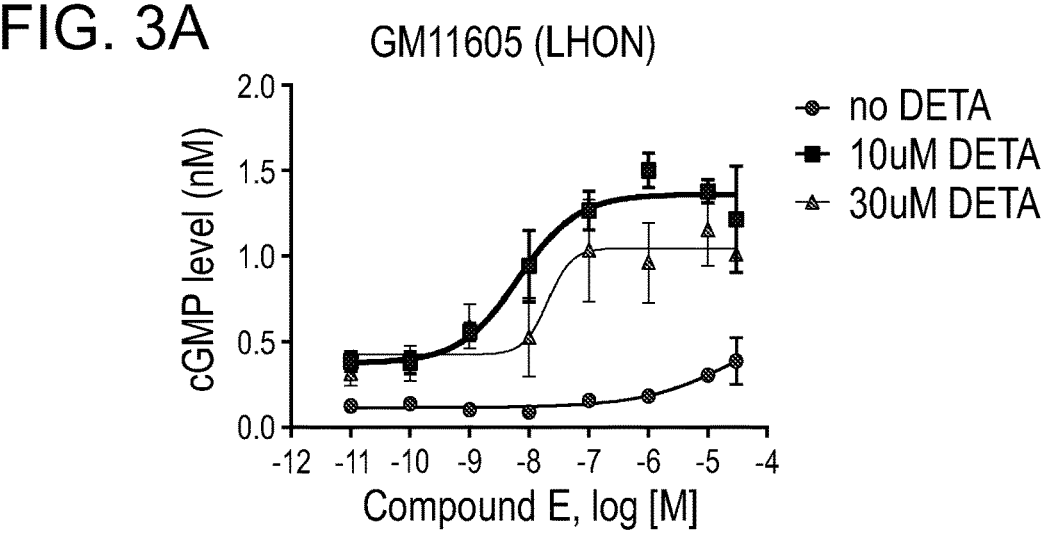
FIGS. 3A, 3B and 3C are graphs showing that Compound E in combination with DETA significantly activated cGMP formation in LHON patient cells GM11605 (A) and GM10742 (B) and Leigh patient cells GM13740 (C), confirming functional expression of sGC in these patient cells.
Figure 3B:
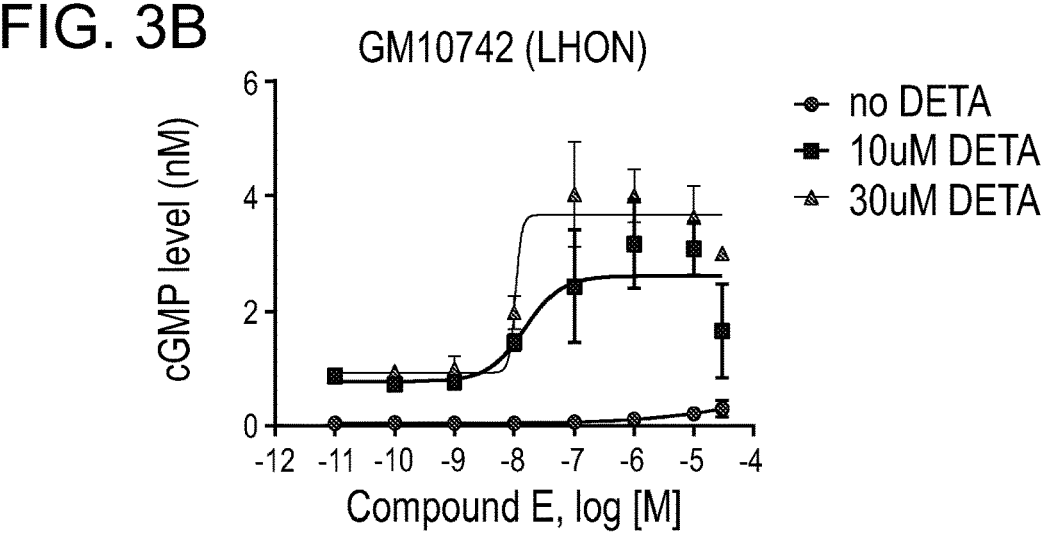
Figure 3C:
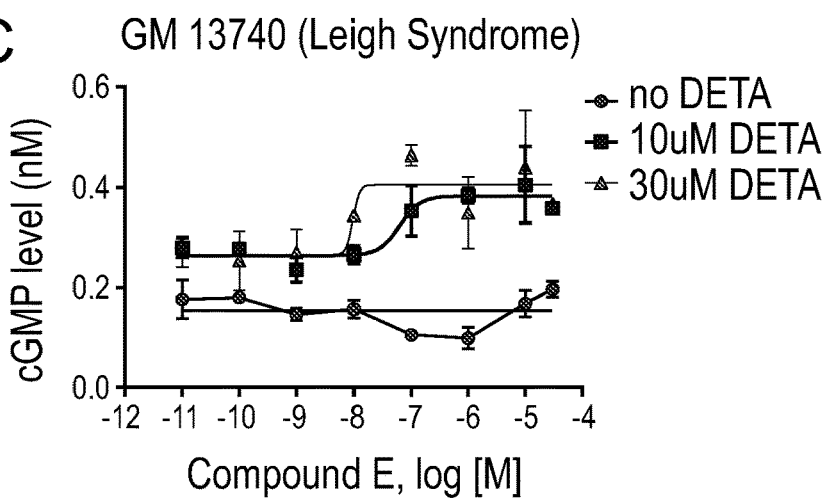

Stimulation of cells from LHON and Leigh patients with Compound E in combination with DETA significantly activated cGMP formation confirming functional expression of sGC in these cells and that Compound E acted as a stimulator for sGC. (FIG. 3A-C)

ATP Assay

Figure 4C:
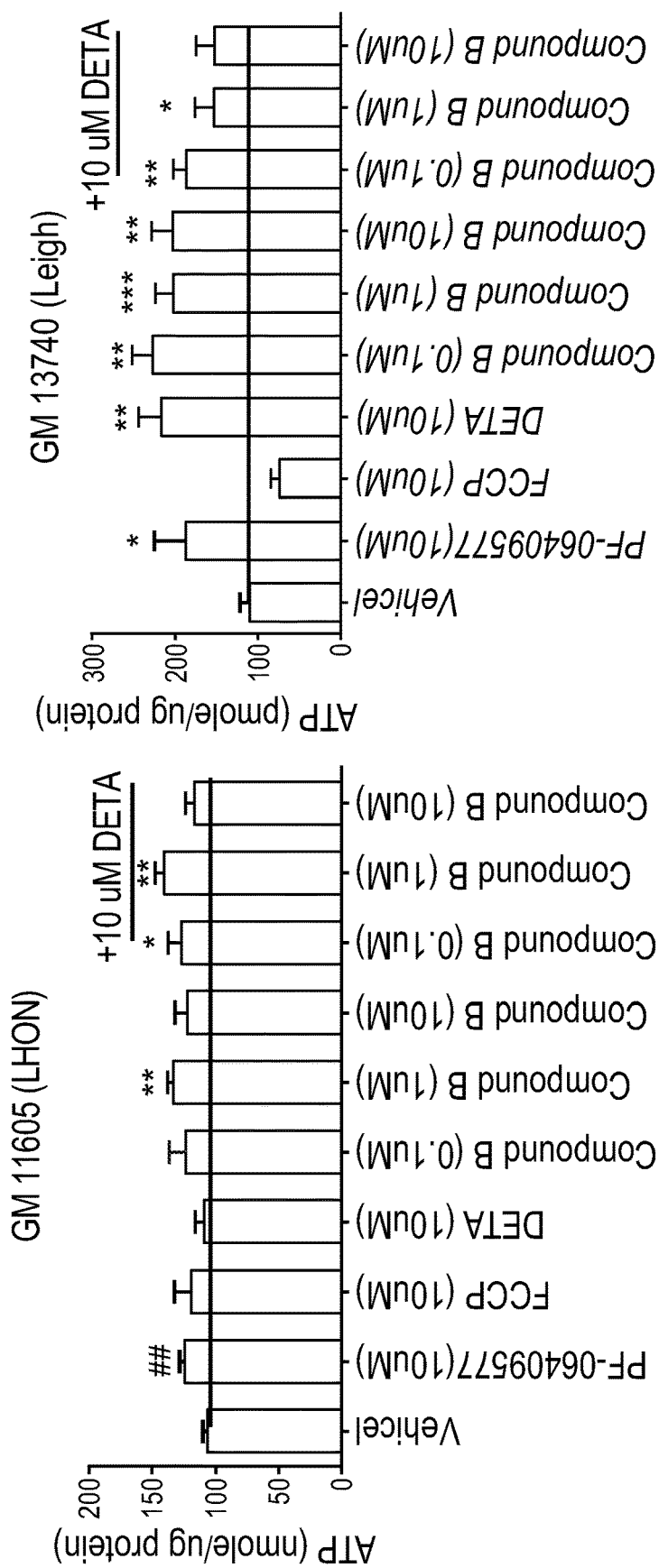
Figure 4D:
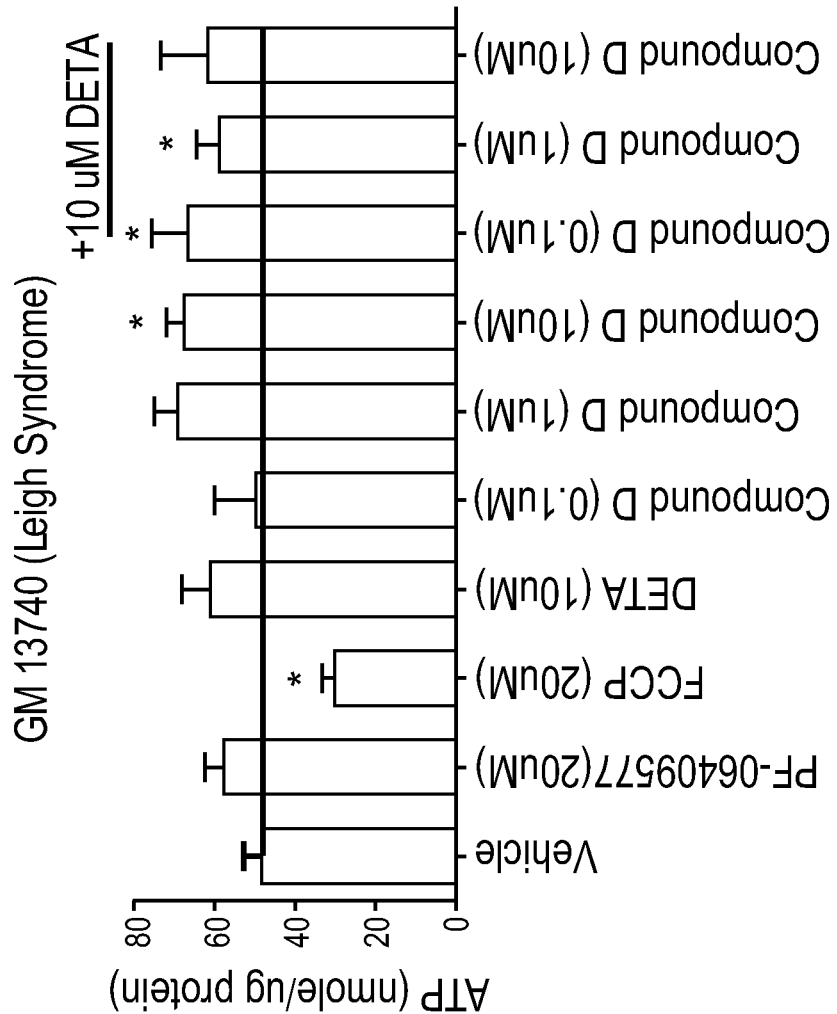

The ATP level in LHON patient cells, GM11605 and GM 10742, and Leigh patient cells GM13740 were significantly lower than in healthy cells, GM 00333 (FIG. 4A). Stimulation of GM11605 and GM13740 with Compound E (alone or in combination with DETA) significantly increase the ATP production (GM10742 was not tested) (FIG. 4B). Stimulation of GM11605, GM10742, and GM13740 with Compound B (alone or in combination with DETA) increase ATP production (FIG. 4C). Compound D was only tested in GM13740 cells and it increased ATP levels significantly (FIG. 4D). These results suggest that sGC stimulators were able to improve ATP crisis in these patient cells. PF-06409577 is an AMPK activator, served as positive control in the assay. FCCP is a chemical uncoupler of the Electronic Transporter Chain (ETC), served as negative control in the assay.

B-DNA Assay

The gene expression profile analysis by B-DNA assay determined the expression levels of multiple mitochondrial genes, including TFAM and DDAH2, in LHON patient cells (GM11605, FIG. 5A-B) and Leigh patient cells (FIG. 6A-B). These genes encode the essential components in the mitochondria that are responsible for ATP production.

TFAM is an abundantly expressed protein present in mitochondria that is necessary for mitochondrial transcription and regulates the mtDNA-copy number, thus being important for maintaining ATP production (Alvarez, V et al 2008 in intro). TFAM also protects the mtDNA from oxidative stress by binding to it in a non-sequence specific manner (Kanki et al., 2004). Previous experiments found that introduction of recombinant TFAM in cybrid cells harboring the Gi 1778A LHON mutation increases basal respiration (Iyer, S et al 2009 Mitochondrion). Additionally, in an in vivo study, Iyer et al injected recombinant TFAM into the tail vein of adult mice and assayed for motor endurance and increase in mitochondrial respiration. Significant increase in mitochondrial complex I respiration in brain and muscle mitochondria was observed in treated mice (Iyer S et al., 2009).

One of the consequences of increased oxidative stress in mitochondrial disease is inhibition of DDAH2 activity (El-Hattab A W et al 2012 review molecular genetics vol 107), an enzyme that degrades Asymmetric dimethylarginine (ADMA). ADMA increase can cause mitochondrial dysfunction (Sud N et al 2008), and increased levels of ADMA were found in mitochondrial disease patients (El-Hattab, A W el al 2012 Mol Genet metabolism Vol 105). Inhibition of DDAH2 further aggravates mitochondrial disease in these patients.

Results

Gene expression profile analysis by B-DNA assay demonstrated that expression levels of two mitochondrial genes, TFAM and DDAH2, were significantly decreased in LHON patient cells (GM11605) (FIG. 5A-B) and Leigh patient cells (GM13740) (FIG. 6A-B).

TFAM was increased by the stimulation of Compound B in the presence of DETA in LHON patient cell lines (FIG. 5A) in Leigh patient cell lines (FIG. 6A).

DDAH2 was increased by the stimulation of Compound B in the presence of DETA in LHON patient cell lines (FIG. 5B) in Leigh patient cell lines (FIG. 6B).

Conclusions.

sGC stimulators increase TFAM mRNA levels inpatient cells. FIGS. 5A and 6A show that TFAM mRNA is decreased in Leigh and LHON patient cells and treatment with sGC stimulators increase the levels of TFAM mRNA in these cells. The increase of TFAM mRNA measured in patient cells treated with sGC stimulator indicate that sGC stimulators can increase TFAM levels in mitochondrial disease patient cells and likely improve mitochondrial respiration. These data indicate that increased TFAM can improve mitochondrial respiration and ameliorate the energy crisis (i.e., the ATP crisis) that characterized mitochondrial disease.

sGC stimulators increase DDAH2 mRNA levels inpatient cells. FIGS. 6B and 6B show that in mitochondrial disease patient cells, sGC stimulator treatment increases the levels of DDAH2 mRNA. Upregulation of the DDAH pathway is expected to reduce ADMA levels in mitochondrial disease patients and decrease the deleterious effects of oxidative stress in these patients. Results from a clinical study of the sGC stimulator praliciguat (Compound A) found that treatment of diabetic patients with praliciguat reduced the levels of circulating ADMA (Hanrahan J P et al, Fourteen-day study of praliciguat, a soluble guanylate cyclase stimulator, in patients with diabetes and hypertension. Diabetes. 2018 July; 67 (Supplement 1). Abstract No. 74-OR).

OTHER EMBODIMENTS

All publications and patents referred to in this disclosure are incorporated herein by reference to the same extent as if each individual publication or patent application were specifically and individually indicated to be incorporated by reference. Should the meaning of the terms in any of the patents or publications incorporated by reference conflict with the meaning of the terms used in this disclosure, the meaning of the terms in this disclosure are intended to be controlling. Furthermore, the foregoing discussion discloses and describes merely exemplary embodiments of the present invention. One skilled in the art will readily recognize from such discussion and from the accompanying drawings and claims, that various changes, modifications and variations can be made therein without departing from the spirit and scope of the invention as defined in the following claims. A number of embodiments have been described. Nevertheless, it will be understood that various modifications may be made without departing from the spirit and scope of the invention.

I claim:

1. A method of treating MELAS (Mitochondrial myopathy, encephalomyopathy, lactic acidosis, stroke-like symptoms) in a patient in need thereof, comprising administering to said patient a therapeutically effective amount of an sGC stimulator or a pharmaceutically acceptable salt thereof, wherein the sGC stimulator or a pharmaceutically acceptable salt thereof, is represented by the following formula:

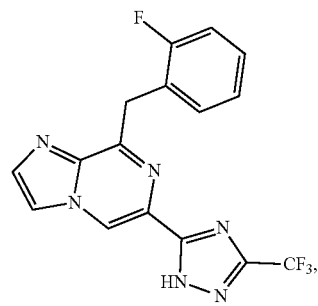 [SMILES: Fc1ccccc1Cc1nc(-c2nc(C(F)(F)F)n[nH]2)cn2ccnc12]

or a pharmaceutically acceptable salt thereof.

2. The method of claim 1, wherein said sGC stimulator, or a pharmaceutically acceptable salt thereof, is administered in combination with arginine or citrulline.

3. A method of treating MELAS (Mitochondrial myopathy, encephalomyopathy, lactic acidosis, stroke-like symptoms) in a patient in need thereof, comprising administering to said patient a therapeutically effective amount of an sGC stimulator, wherein the sGC stimulator is represented by the following formula:

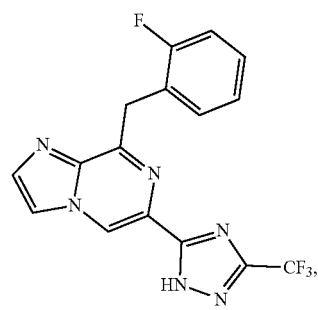 [SMILES: Fc1ccccc1Cc1nc(-c2nc(C(F)(F)F)n[nH]2)cn2ccnc12]

4. The method of claim 3, wherein said sGC stimulator is administered in combination with arginine or citrulline.

* * * * *